(12) United States Patent
Garabedian et al.

(10) Patent No.: US 8,394,102 B2
(45) Date of Patent: Mar. 12, 2013

(54) SURGICAL TOOLS FOR TREATMENT OF SPINAL STENOSIS

(75) Inventors: Robert Garabedian, Mountain View, CA (US); Amie R. Borgstrom, San Francisco, CA (US); Gregory B. Arcenio, Redwood City, CA (US); Ronald Leguidleguid, Fremont, CA (US); Michael P. Wallace, Pleasanton, CA (US); Bryan Knodel, Flagstaff, AZ (US)

(73) Assignee: Baxano, Inc., San Jose, CA (US)

( * ) Notice: Subject to any disclaimer, the term of this patent is extended or adjusted under 35 U.S.C. 154(b) by 219 days.

(21) Appl. No.: 12/824,043

(22) Filed: Jun. 25, 2010

(65) Prior Publication Data
US 2010/0331900 A1   Dec. 30, 2010

Related U.S. Application Data

(60) Provisional application No. 61/220,314, filed on Jun. 25, 2009, provisional application No. 61/253,811, filed on Oct. 21, 2009.

(51) Int. Cl.
*A61B 17/70* (2006.01)
(52) U.S. Cl. ..................... 606/86 A; 606/279
(58) Field of Classification Search ............... 606/86 A, 606/279, 107, 228
See application file for complete search history.

(56) References Cited

U.S. PATENT DOCUMENTS

| 184,804 A | 11/1876 | Stohlmann |
|---|---|---|
| 289,104 A | 11/1883 | How |
| 863,389 A | 8/1907 | Harkin |
| 1,039,487 A | 9/1912 | Casebolt |
| 1,201,467 A | 10/1916 | Hoglund |
| 1,374,638 A | 4/1921 | De Cew et al. |
| 1,543,195 A | 6/1925 | Thygesen |
| 1,690,812 A | 11/1928 | Bertels |
| 1,938,200 A | 12/1933 | Wells |
| 2,243,757 A | 5/1941 | Kohls et al. |
| 2,269,749 A | 1/1942 | Wilkie |

(Continued)

FOREIGN PATENT DOCUMENTS

| DE | 3209403 A1 | 9/1983 |
|---|---|---|
| DE | 4036804 A1 | 5/1992 |

(Continued)

OTHER PUBLICATIONS

Schmitz et al.; U.S. Appl. No. 12/816,729 entitled Access and Tissue Modification Systems and Methods, filed Jun. 16, 2010.

(Continued)

*Primary Examiner* — Eduardo C Robert
*Assistant Examiner* — Christina Negrellirodriguez
(74) *Attorney, Agent, or Firm* — Shay Glenn LLP

(57) ABSTRACT

Described herein are pullwire handle devices for securing to a tissue-penetrating pullwire. In some embodiments, the device includes a handle body, a pullwire lock configured to removably lock the pullwire handle device onto a pullwire within the handle body, and a tip containment element configured to retain the distal tip of the pullwire. In some embodiments, the handle body further comprises a storage chamber configured to store a distal portion of the pullwire. Also described herein are methods for capturing a pullwire using a pullwire handle device. In some embodiments, the method includes the steps of inserting the distal end of a pullwire into the pullwire handle device, advancing the pullwire further into the pullwire handle device while the distal portion of the pullwire is contained within the pullwire handle device, and locking the distal portion of the pullwire within the pullwire handle device.

16 Claims, 32 Drawing Sheets

U.S. PATENT DOCUMENTS

| | | |
|---|---|---|
| 2,372,553 A | 3/1945 | Coddington |
| 2,437,697 A | 3/1948 | Kalom |
| 2,516,882 A | 8/1950 | Kalom |
| 2,704,064 A | 5/1955 | Fizzell |
| 2,820,281 A | 1/1958 | Amsen |
| 2,843,128 A | 7/1958 | Storz |
| 2,982,005 A | 5/1961 | Booth |
| RE25,582 E | 5/1964 | Davies |
| 3,150,470 A | 9/1964 | Barron |
| 3,200,814 A | 8/1965 | Taylor et al. |
| 3,389,447 A | 6/1968 | Theobald et al. |
| 3,491,776 A | 1/1970 | Fleming |
| 3,495,590 A | 2/1970 | Zeiller |
| 3,528,152 A | 9/1970 | Funakubo et al. |
| 3,624,484 A | 11/1971 | Colyer |
| 3,640,280 A | 2/1972 | Slanker et al. |
| 3,651,844 A | 3/1972 | Barnes |
| 3,664,329 A | 5/1972 | Naylor |
| 3,682,162 A | 8/1972 | Colyer |
| 3,699,729 A | 10/1972 | Garvey et al. |
| 3,752,166 A | 8/1973 | Lyon et al. |
| 3,774,355 A | 11/1973 | Dawson et al. |
| 3,830,226 A | 8/1974 | Staub et al. |
| 3,835,859 A | 9/1974 | Roberts et al. |
| 3,956,858 A | 5/1976 | Catlin et al. |
| 3,957,036 A | 5/1976 | Normann |
| 3,978,862 A | 9/1976 | Morrison |
| 3,999,294 A | 12/1976 | Shoben |
| 4,015,931 A | 4/1977 | Thakur |
| 4,099,519 A | 7/1978 | Warren |
| 4,108,182 A | 8/1978 | Hartman et al. |
| 4,160,320 A | 7/1979 | Wikoff |
| 4,172,440 A | 10/1979 | Schneider et al. |
| 4,203,444 A | 5/1980 | Bonnell et al. |
| 4,207,897 A | 6/1980 | Lloyd et al. |
| 4,259,276 A | 3/1981 | Rawlings |
| 4,405,061 A | 9/1983 | Bergandy |
| D273,806 S | 5/1984 | Bolesky et al. |
| 4,464,836 A | 8/1984 | Hissa |
| 4,502,184 A | 3/1985 | Karubian |
| 4,515,168 A | 5/1985 | Chester et al. |
| 4,518,022 A | 5/1985 | Valdes et al. |
| 4,545,374 A | 10/1985 | Jacobson |
| 4,573,448 A | 3/1986 | Kambin |
| 4,580,545 A | 4/1986 | Dorsten |
| 4,590,949 A | 5/1986 | Pohndorf |
| 4,616,660 A | 10/1986 | Johns |
| 4,621,636 A | 11/1986 | Fogarty |
| 4,625,725 A | 12/1986 | Davison et al. |
| 4,660,571 A | 4/1987 | Hess et al. |
| 4,678,459 A | 7/1987 | Onik et al. |
| 4,690,642 A | 9/1987 | Kyotani |
| 4,700,702 A | 10/1987 | Nilsson |
| 4,709,699 A | 12/1987 | Michael et al. |
| 4,741,343 A | 5/1988 | Bowman |
| 4,750,249 A | 6/1988 | Richardson |
| 4,794,931 A | 1/1989 | Yock |
| 4,808,157 A | 2/1989 | Coombs |
| 4,817,628 A | 4/1989 | Zealear et al. |
| 4,856,193 A | 8/1989 | Grachan |
| 4,867,155 A | 9/1989 | Isaacson |
| 4,872,452 A | 10/1989 | Alexson |
| 4,873,978 A | 10/1989 | Ginsburg |
| 4,883,460 A | 11/1989 | Zanetti |
| 4,894,063 A | 1/1990 | Nashe |
| 4,912,799 A | 4/1990 | Coleman, Jr. |
| RE33,258 E | 7/1990 | Onik et al. |
| 4,943,295 A | 7/1990 | Hartlaub et al. |
| 4,946,462 A | 8/1990 | Watanabe |
| 4,957,117 A | 9/1990 | Wysham |
| 4,962,766 A | 10/1990 | Herzon |
| 4,973,329 A | 11/1990 | Park et al. |
| 4,990,148 A | 2/1991 | Worrick, III et al. |
| 4,994,036 A | 2/1991 | Biscoping et al. |
| 4,994,072 A | 2/1991 | Bhate et al. |
| 4,995,200 A | 2/1991 | Eberhart |
| 5,019,082 A | 5/1991 | Frey et al. |
| 5,025,787 A | 6/1991 | Sutherland et al. |
| 5,026,379 A | 6/1991 | Yoon |
| 5,026,386 A | 6/1991 | Michelson |
| 5,078,137 A | 1/1992 | Edell et al. |
| 5,089,003 A | 2/1992 | Fallin et al. |
| 5,100,424 A | 3/1992 | Jang et al. |
| 5,108,403 A | 4/1992 | Stern |
| 5,123,400 A | 6/1992 | Edgerton |
| 5,125,928 A | 6/1992 | Parins et al. |
| 5,147,364 A | 9/1992 | Comparetto |
| 5,152,749 A | 10/1992 | Giesy et al. |
| 5,161,534 A | 11/1992 | Berthiaume |
| 5,163,939 A | 11/1992 | Winston |
| 5,176,649 A | 1/1993 | Wakabayashi |
| 5,178,145 A | 1/1993 | Rea |
| 5,178,161 A | 1/1993 | Kovacs |
| 5,191,888 A | 3/1993 | Palmer et al. |
| 5,195,507 A | 3/1993 | Bilweis |
| 5,201,704 A | 4/1993 | Ray |
| 5,215,105 A | 6/1993 | Kizelshteyn et al. |
| 5,219,358 A | 6/1993 | Bendel et al. |
| 5,234,435 A | 8/1993 | Seagrave, Jr. |
| 5,242,418 A | 9/1993 | Weinstein |
| 5,250,035 A | 10/1993 | Smith et al. |
| 5,255,691 A | 10/1993 | Otten |
| 5,271,415 A | 12/1993 | Foerster et al. |
| 5,281,218 A | 1/1994 | Imran |
| 5,284,153 A | 2/1994 | Raymond et al. |
| 5,284,154 A | 2/1994 | Raymond et al. |
| 5,300,077 A | 4/1994 | Howell |
| 5,325,868 A | 7/1994 | Kimmelstiel |
| 5,341,807 A | 8/1994 | Nardella |
| 5,351,679 A | 10/1994 | Mayzels et al. |
| 5,353,784 A | 10/1994 | Nady-Mohamed |
| 5,353,789 A | 10/1994 | Schlobohm |
| 5,353,802 A | 10/1994 | Ollmar |
| 5,360,441 A | 11/1994 | Otten |
| 5,365,928 A | 11/1994 | Rhinehart et al. |
| 5,374,261 A | 12/1994 | Yoon |
| 5,383,879 A | 1/1995 | Phillips |
| 5,385,146 A | 1/1995 | Goldreyer |
| 5,387,218 A | 2/1995 | Meswania |
| 5,396,880 A | 3/1995 | Kagan et al. |
| 5,421,348 A | 6/1995 | Larnard |
| 5,423,331 A | 6/1995 | Wysham |
| 5,437,661 A | 8/1995 | Rieser |
| 5,439,464 A | 8/1995 | Shapiro |
| 5,441,044 A | 8/1995 | Tovey et al. |
| 5,441,510 A | 8/1995 | Simpson et al. |
| 5,454,815 A | 10/1995 | Geisser et al. |
| 5,456,254 A | 10/1995 | Pietroski et al. |
| 5,496,325 A | 3/1996 | McLees |
| 5,512,037 A | 4/1996 | Russell et al. |
| 5,515,848 A | 5/1996 | Corbett, III et al. |
| 5,531,749 A | 7/1996 | Michelson |
| 5,534,009 A | 7/1996 | Lander |
| 5,546,958 A | 8/1996 | Thorud et al. |
| 5,554,110 A | 9/1996 | Edwards et al. |
| 5,555,892 A | 9/1996 | Tipton |
| 5,560,372 A | 10/1996 | Cory |
| 5,562,695 A | 10/1996 | Obenchain |
| 5,571,181 A | 11/1996 | Li |
| 5,582,618 A | 12/1996 | Chin et al. |
| 5,598,848 A | 2/1997 | Swanson et al. |
| 5,620,447 A | 4/1997 | Smith et al. |
| 5,630,426 A | 5/1997 | Eggers et al. |
| 5,634,475 A | 6/1997 | Wolvek |
| 5,643,304 A | 7/1997 | Schechter et al. |
| 5,651,373 A | 7/1997 | Mah |
| 5,656,012 A | 8/1997 | Sienkiewicz |
| 5,680,860 A | 10/1997 | Imran |
| 5,681,324 A | 10/1997 | Kammerer et al. |
| 5,697,889 A | 12/1997 | Slotman et al. |
| 5,709,697 A | 1/1998 | Ratcliff et al. |
| 5,725,530 A | 3/1998 | Popken |
| 5,735,792 A | 4/1998 | Vanden Hoek et al. |
| 5,755,732 A | 5/1998 | Green et al. |
| 5,759,159 A | 6/1998 | Masreliez |
| 5,762,629 A | 6/1998 | Kambin |
| 5,766,168 A | 6/1998 | Mantell |

| | | | | | |
|---|---|---|---|---|---|
| 5,769,865 A | 6/1998 | Kermode et al. | 6,277,094 B1 | 8/2001 | Schendel |
| 5,775,331 A | 7/1998 | Raymond et al. | 6,280,447 B1 | 8/2001 | Marino et al. |
| 5,779,642 A | 7/1998 | Nightengale | 6,292,702 B1 | 9/2001 | King et al. |
| 5,788,653 A | 8/1998 | Lorenzo | 6,298,256 B1 | 10/2001 | Meyer |
| 5,792,044 A | 8/1998 | Foley et al. | 6,312,392 B1 | 11/2001 | Herzon |
| 5,795,308 A | 8/1998 | Russin | 6,324,418 B1 | 11/2001 | Crowley et al. |
| 5,800,350 A | 9/1998 | Coppleson et al. | 6,324,432 B1 | 11/2001 | Rigaux et al. |
| 5,803,902 A | 9/1998 | Sienkiewicz et al. | 6,325,764 B1 | 12/2001 | Griffith et al. |
| 5,803,904 A | 9/1998 | Mehdizadeh | 6,334,068 B1 | 12/2001 | Hacker |
| 5,807,263 A | 9/1998 | Chance | 6,343,226 B1 | 1/2002 | Sunde et al. |
| 5,810,744 A | 9/1998 | Chu et al. | 6,358,254 B1 | 3/2002 | Anderson |
| 5,813,405 A | 9/1998 | Montano, Jr. et al. | 6,360,750 B1 | 3/2002 | Gerber et al. |
| 5,824,040 A | 10/1998 | Cox et al. | 6,364,886 B1 | 4/2002 | Sklar |
| 5,830,151 A | 11/1998 | Hadzic et al. | 6,368,324 B1 | 4/2002 | Dinger et al. |
| 5,830,157 A | 11/1998 | Foote | 6,370,411 B1 | 4/2002 | Osadchy et al. |
| 5,830,188 A | 11/1998 | Abouleish | 6,370,435 B1 | 4/2002 | Panescu et al. |
| 5,833,692 A | 11/1998 | Cesarini et al. | 6,383,509 B1 | 5/2002 | Donovan et al. |
| 5,836,948 A | 11/1998 | Zucherman et al. | 6,390,906 B1 | 5/2002 | Subramanian |
| 5,843,110 A | 12/1998 | Dross et al. | 6,391,028 B1 | 5/2002 | Fanton et al. |
| 5,846,196 A | 12/1998 | Siekmeyer et al. | 6,416,505 B1 | 7/2002 | Fleischman et al. |
| 5,846,244 A | 12/1998 | Cripe | 6,423,071 B1 | 7/2002 | Lawson |
| 5,851,191 A | 12/1998 | Gozani | 6,423,080 B1 | 7/2002 | Gellman et al. |
| 5,851,209 A | 12/1998 | Kummer et al. | 6,425,859 B1 | 7/2002 | Foley et al. |
| 5,851,214 A | 12/1998 | Larsen et al. | 6,425,887 B1 | 7/2002 | McGuckin et al. |
| 5,853,373 A | 12/1998 | Griffith et al. | 6,428,486 B2 | 8/2002 | Ritchart et al. |
| 5,865,844 A | 2/1999 | Plaia et al. | 6,436,101 B1 | 8/2002 | Hamada |
| 5,868,767 A | 2/1999 | Farley et al. | 6,442,848 B1 | 9/2002 | Dean |
| 5,879,353 A | 3/1999 | Terry | 6,446,621 B1 | 9/2002 | Svensson |
| 5,885,219 A | 3/1999 | Nightengale | 6,451,335 B1 | 9/2002 | Goldenheim et al. |
| 5,895,417 A | 4/1999 | Pomeranz et al. | 6,454,767 B2 | 9/2002 | Alleyne |
| 5,897,583 A | 4/1999 | Meyer et al. | 6,464,682 B1 | 10/2002 | Snoke |
| 5,899,909 A | 5/1999 | Claren et al. | 6,466,817 B1 | 10/2002 | Kaula et al. |
| 5,904,657 A | 5/1999 | Unsworth et al. | 6,468,289 B1 | 10/2002 | Bonutti |
| 5,916,173 A | 6/1999 | Kirsner | 6,470,209 B2 | 10/2002 | Snoke |
| 5,918,604 A | 7/1999 | Whelan | 6,478,805 B1 | 11/2002 | Marino et al. |
| 5,919,190 A | 7/1999 | VanDusseldorp | 6,487,439 B1 | 11/2002 | Skladnev et al. |
| 5,928,158 A | 7/1999 | Aristides | 6,488,636 B2 | 12/2002 | Bryan et al. |
| 5,928,159 A | 7/1999 | Eggers et al. | 6,491,646 B1 | 12/2002 | Blackledge |
| 5,941,822 A | 8/1999 | Skladnev et al. | 6,500,128 B2 | 12/2002 | Marino |
| 5,961,522 A | 10/1999 | Mehdizadeh | 6,500,189 B1 | 12/2002 | Lang et al. |
| 5,972,013 A | 10/1999 | Schmidt | 6,512,958 B1 | 1/2003 | Swoyer et al. |
| 5,976,110 A | 11/1999 | Greengrass et al. | 6,516,223 B2 | 2/2003 | Hofmann |
| 5,976,146 A | 11/1999 | Ogawa et al. | 6,520,907 B1 | 2/2003 | Foley et al. |
| 6,002,964 A | 12/1999 | Feler et al. | 6,527,786 B1 | 3/2003 | Davis et al. |
| 6,004,326 A | 12/1999 | Castro et al. | 6,533,749 B1 | 3/2003 | Mitusina et al. |
| 6,004,330 A | 12/1999 | Middleman et al. | 6,535,759 B1 | 3/2003 | Epstein et al. |
| 6,010,493 A | 1/2000 | Snoke | 6,540,742 B1 | 4/2003 | Thomas et al. |
| 6,015,406 A | 1/2000 | Goble et al. | 6,540,761 B2 | 4/2003 | Houser |
| 6,022,362 A | 2/2000 | Lee et al. | 6,546,270 B1 | 4/2003 | Goldin et al. |
| 6,030,383 A | 2/2000 | Benderev | 6,558,353 B2 | 5/2003 | Zohmann |
| 6,030,401 A | 2/2000 | Marino | 6,558,390 B2 | 5/2003 | Cragg |
| 6,038,480 A | 3/2000 | Hrdlicka et al. | 6,562,033 B2 | 5/2003 | Shah et al. |
| 6,048,345 A | 4/2000 | Berke et al. | 6,564,078 B1 | 5/2003 | Marino et al. |
| 6,068,642 A | 5/2000 | Johnson et al. | 6,564,079 B1 | 5/2003 | Cory et al. |
| 6,073,051 A | 6/2000 | Sharkey et al. | 6,564,088 B1 | 5/2003 | Soller et al. |
| 6,099,514 A | 8/2000 | Sharkey et al. | 6,569,160 B1 | 5/2003 | Goldin et al. |
| 6,102,930 A | 8/2000 | Simmons, Jr. | 6,575,979 B1 | 6/2003 | Cragg |
| 6,106,558 A | 8/2000 | Picha | 6,579,291 B1 | 6/2003 | Keith et al. |
| 6,113,534 A | 9/2000 | Koros et al. | 6,584,345 B2 | 6/2003 | Govari |
| D432,384 S | 10/2000 | Simons | 6,592,559 B1 | 7/2003 | Pakter et al. |
| 6,132,387 A | 10/2000 | Gozani et al. | 6,595,932 B2 | 7/2003 | Ferrera |
| 6,136,014 A | 10/2000 | Sirimanne et al. | 6,597,955 B2 | 7/2003 | Panescu et al. |
| 6,142,993 A | 11/2000 | Whayne et al. | 6,606,523 B1 | 8/2003 | Jenkins |
| 6,142,994 A | 11/2000 | Swanson et al. | 6,607,530 B1 | 8/2003 | Carl et al. |
| 6,146,380 A | 11/2000 | Racz et al. | 6,609,018 B2 | 8/2003 | Cory et al. |
| 6,152,894 A | 11/2000 | Kubler | 6,610,066 B2 | 8/2003 | Dinger et al. |
| 6,169,916 B1 | 1/2001 | West | 6,620,129 B2 | 9/2003 | Stecker et al. |
| 6,205,360 B1 | 3/2001 | Carter et al. | 6,622,731 B2 | 9/2003 | Daniel et al. |
| 6,214,001 B1 | 4/2001 | Casscells et al. | 6,624,510 B1 | 9/2003 | Chan et al. |
| 6,214,016 B1 | 4/2001 | Williams et al. | 6,626,916 B1 | 9/2003 | Yeung et al. |
| 6,236,892 B1 | 5/2001 | Feler | 6,632,184 B1 | 10/2003 | Truwit |
| 6,251,115 B1 | 6/2001 | Williams et al. | 6,638,233 B2 | 10/2003 | Corvi et al. |
| 6,256,540 B1 | 7/2001 | Panescu et al. | RE38,335 E | 11/2003 | Aust et al. |
| 6,259,945 B1 | 7/2001 | Epstein et al. | 6,648,883 B2 | 11/2003 | Francischelli et al. |
| 6,261,582 B1 | 7/2001 | Needham et al. | 6,666,874 B2 | 12/2003 | Heitzmann et al. |
| 6,266,551 B1 | 7/2001 | Osadchy et al. | 6,673,063 B2 | 1/2004 | Brett |
| 6,266,558 B1 | 7/2001 | Gozani et al. | 6,673,068 B1 | 1/2004 | Berube |
| 6,267,760 B1 | 7/2001 | Swanson | 6,678,552 B2 | 1/2004 | Pearlman |
| 6,272,367 B1 | 8/2001 | Chance | 6,682,535 B2 | 1/2004 | Hoogland |

| Patent Number | Date | Inventor |
|---|---|---|
| 6,682,536 B2 | 1/2004 | Vardi et al. |
| 6,685,709 B2 | 2/2004 | Sklar |
| 6,699,246 B2 | 3/2004 | Zucherman et al. |
| 6,723,049 B2 | 4/2004 | Skladnev et al. |
| 6,726,531 B1 | 4/2004 | Harrel |
| 6,726,685 B2 | 4/2004 | To et al. |
| 6,733,496 B2 | 5/2004 | Skladney et al. |
| 6,736,815 B2 | 5/2004 | Ginn |
| 6,736,835 B2 | 5/2004 | Pellegrino et al. |
| 6,746,451 B2 | 6/2004 | Middleton et al. |
| 6,752,814 B2 | 6/2004 | Gellman et al. |
| 6,760,616 B2 | 7/2004 | Hoey et al. |
| 6,764,491 B2 | 7/2004 | Frey et al. |
| 6,772,012 B2 | 8/2004 | Ricart et al. |
| 6,776,765 B2 | 8/2004 | Soukup et al. |
| 6,786,876 B2 | 9/2004 | Cox |
| 6,788,966 B2 | 9/2004 | Kenan et al. |
| 6,790,210 B1 | 9/2004 | Cragg et al. |
| 6,795,737 B2 | 9/2004 | Gielen et al. |
| 6,805,695 B2 | 10/2004 | Keith et al. |
| 6,805,697 B1 | 10/2004 | Helm et al. |
| 6,807,444 B2 | 10/2004 | Tu et al. |
| 6,830,561 B2 | 12/2004 | Jansen et al. |
| 6,830,570 B1 | 12/2004 | Frey et al. |
| 6,832,111 B2 | 12/2004 | Tu et al. |
| 6,845,264 B1 | 1/2005 | Skladnev et al. |
| 6,847,849 B2 | 1/2005 | Mamo et al. |
| 6,851,430 B2 | 2/2005 | Tsou |
| 6,865,409 B2 | 3/2005 | Getsla et al. |
| 6,872,204 B2 | 3/2005 | Houser |
| 6,875,221 B2 | 4/2005 | Cull |
| 6,882,879 B2 | 4/2005 | Rock |
| 6,884,220 B2 | 4/2005 | Aviv et al. |
| 6,890,353 B2 | 5/2005 | Cohn et al. |
| 6,895,283 B2 | 5/2005 | Erickson et al. |
| 6,899,716 B2 | 5/2005 | Cragg |
| 6,907,884 B2 | 6/2005 | Pellegrino et al. |
| 6,911,003 B2 | 6/2005 | Anderson et al. |
| 6,911,016 B2 | 6/2005 | Balzum et al. |
| 6,916,328 B2 | 7/2005 | Brett |
| 6,923,813 B2 | 8/2005 | Phillips et al. |
| 6,929,647 B2 | 8/2005 | Cohen |
| 6,949,104 B2 | 9/2005 | Griffis et al. |
| 6,962,587 B2 | 11/2005 | Johnson et al. |
| 6,969,392 B2 | 11/2005 | Gitis et al. |
| 6,971,986 B2 | 12/2005 | Staskin et al. |
| 6,972,199 B2 | 12/2005 | Lebouitz et al. |
| 6,973,342 B1 | 12/2005 | Swanson |
| 6,976,986 B2 | 12/2005 | Berube |
| 6,991,643 B2 | 1/2006 | Saadat |
| 6,994,693 B2 | 2/2006 | Tal |
| 6,997,934 B2 | 2/2006 | Snow et al. |
| 6,999,820 B2 | 2/2006 | Jordan |
| 7,001,333 B2 | 2/2006 | Hamel et al. |
| 7,008,431 B2 | 3/2006 | Simonson |
| 7,010,352 B2 | 3/2006 | Hogan |
| 7,011,635 B1 | 3/2006 | Delay |
| 7,011,663 B2 | 3/2006 | Michelson |
| 7,014,616 B2 | 3/2006 | Ferrera |
| 7,033,373 B2 | 4/2006 | de la Torre et al. |
| 7,041,099 B2 | 5/2006 | Thomas et al. |
| 7,047,084 B2 | 5/2006 | Erickson et al. |
| 7,048,682 B2 | 5/2006 | Neisz et al. |
| 7,050,848 B2 | 5/2006 | Hoey et al. |
| 7,063,682 B1 | 6/2006 | Whayne et al. |
| 7,069,083 B2 | 6/2006 | Finch et al. |
| 7,070,556 B2 | 7/2006 | Anderson et al. |
| 7,070,596 B1 | 7/2006 | Woloszko et al. |
| 7,079,883 B2 | 7/2006 | Marino et al. |
| 7,081,122 B1 | 7/2006 | Reiley et al. |
| 7,087,053 B2 | 8/2006 | Vanney |
| 7,087,058 B2 | 8/2006 | Cragg |
| 7,107,104 B2 | 9/2006 | Keravel et al. |
| 7,118,576 B2 | 10/2006 | Gitis et al. |
| 7,141,019 B2 | 11/2006 | Pearlman |
| 7,166,073 B2 | 1/2007 | Ritland |
| 7,166,081 B2 | 1/2007 | McKinley |
| 7,166,107 B2 | 1/2007 | Anderson |
| 7,169,107 B2 | 1/2007 | Jersey-Willuhn et al. |
| 7,172,562 B2 | 2/2007 | McKinley |
| 7,177,677 B2 | 2/2007 | Kaula et al. |
| 7,181,289 B2 | 2/2007 | Pflueger et al. |
| 7,189,240 B1 | 3/2007 | Dekel |
| 7,192,430 B2 | 3/2007 | Truckai et al. |
| 7,198,598 B2 | 4/2007 | Smith et al. |
| 7,198,626 B2 | 4/2007 | Lee et al. |
| 7,207,949 B2 | 4/2007 | Miles et al. |
| 7,211,082 B2 | 5/2007 | Hall et al |
| 7,214,186 B2 | 5/2007 | Ritland |
| 7,214,197 B2 | 5/2007 | Prass |
| 7,216,001 B2 | 5/2007 | Hacker et al. |
| 7,223,278 B2 | 5/2007 | Davison et al. |
| 7,236,832 B2 | 6/2007 | Hemmerling et al. |
| 7,238,189 B2 | 7/2007 | Schmieding et al. |
| 7,239,911 B2 | 7/2007 | Scholz |
| 7,245,789 B2 | 7/2007 | Bates et al. |
| 7,270,658 B2 | 9/2007 | Woloszko et al. |
| 7,270,659 B2 | 9/2007 | Ricart et al. |
| 7,282,033 B2 | 10/2007 | Urmey |
| 7,282,061 B2 | 10/2007 | Sharkey et al. |
| 7,295,881 B2 | 11/2007 | Cohen et al. |
| 7,318,823 B2 | 1/2008 | Sharps et al. |
| 7,337,005 B2 | 2/2008 | Kim et al. |
| 7,337,006 B2 | 2/2008 | Kim et al. |
| 7,367,972 B2 | 5/2008 | Francischelli et al. |
| 7,383,639 B2 | 6/2008 | Malandain |
| 7,390,330 B2 | 6/2008 | Harp |
| 7,419,487 B2 | 9/2008 | Johnson et al. |
| 7,449,019 B2 | 11/2008 | Uchida et al. |
| 7,452,351 B2 | 11/2008 | Miller et al. |
| 7,470,236 B1 | 12/2008 | Kelleher et al. |
| 7,476,226 B2 | 1/2009 | Weikel et al. |
| 7,494,473 B2 | 2/2009 | Eggers et al. |
| 7,500,977 B2 | 3/2009 | Assell et al. |
| 7,503,920 B2 | 3/2009 | Siegal |
| 7,507,218 B2 | 3/2009 | Aliski et al. |
| 7,522,953 B2 | 4/2009 | Gharib et al. |
| 7,553,307 B2 | 6/2009 | Bleich et al. |
| 7,555,343 B2 | 6/2009 | Bleich |
| 7,578,819 B2 | 8/2009 | Bleich et al. |
| 7,617,006 B2 | 11/2009 | Metzler et al. |
| 7,641,658 B2 | 1/2010 | Shaolian et al. |
| 7,648,521 B2 | 1/2010 | Hestad |
| 7,655,026 B2 | 2/2010 | Justis et al. |
| 7,666,186 B2 | 2/2010 | Harp |
| 7,666,209 B2 | 2/2010 | Zucherman et al. |
| 7,738,968 B2 | 6/2010 | Bleich |
| 7,738,969 B2 | 6/2010 | Bleich |
| 7,740,631 B2 | 6/2010 | Bleich et al. |
| 7,857,813 B2 | 12/2010 | Schmitz et al. |
| 7,887,538 B2 | 2/2011 | Bleich et al. |
| 7,918,849 B2 | 4/2011 | Bleich et al. |
| 7,938,830 B2 | 5/2011 | Saadat et al. |
| 8,192,435 B2 | 6/2012 | Bleich et al. |
| 8,192,436 B2 | 6/2012 | Schmitz et al. |
| 8,221,397 B2 | 7/2012 | Bleich et al. |
| 2001/0014806 A1 | 8/2001 | Ellman et al. |
| 2001/0025192 A1 | 9/2001 | Gerber et al. |
| 2001/0039419 A1 | 11/2001 | Francischelli et al. |
| 2002/0022788 A1 | 2/2002 | Corvi et al. |
| 2002/0029060 A1 | 3/2002 | Hogendijk |
| 2002/0106681 A1 | 8/2002 | Wexler et al. |
| 2002/0138091 A1 | 9/2002 | Pflueger |
| 2002/0165590 A1 | 11/2002 | Crowe et al. |
| 2002/0183647 A1 | 12/2002 | Gozani et al. |
| 2003/0015203 A1 | 1/2003 | Makower et al. |
| 2003/0074037 A1 | 4/2003 | Moore et al. |
| 2003/0105503 A1 | 6/2003 | Marino |
| 2003/0113906 A1 | 6/2003 | Sangha et al. |
| 2003/0130655 A1 | 7/2003 | Woloszko et al. |
| 2003/0130738 A1 | 7/2003 | Hovda et al. |
| 2003/0167021 A1 | 9/2003 | Shimm |
| 2003/0187368 A1 | 10/2003 | Sata et al. |
| 2003/0188749 A1 | 10/2003 | Nichols et al. |
| 2003/0212400 A1 | 11/2003 | Bloemer et al. |
| 2003/0225412 A1 | 12/2003 | Shiraishi |
| 2003/0225415 A1 | 12/2003 | Richard |
| 2004/0006379 A1 | 1/2004 | Brett |

| | | | | | | |
|---|---|---|---|---|---|---|
| 2004/0006391 A1 | 1/2004 | Reiley | | 2006/0206117 A1 | 9/2006 | Harp |
| 2004/0019359 A1 | 1/2004 | Worley et al. | | 2006/0206118 A1 | 9/2006 | Kim et al. |
| 2004/0030330 A1 | 2/2004 | Brassell et al. | | 2006/0206178 A1 | 9/2006 | Kim |
| 2004/0049208 A1 | 3/2004 | Hill et al. | | 2006/0224060 A1 | 10/2006 | Garell et al. |
| 2004/0059260 A1 | 3/2004 | Truwit | | 2006/0224078 A1 | 10/2006 | Hoey et al. |
| 2004/0064058 A1 | 4/2004 | McKay | | 2006/0235451 A1 | 10/2006 | Schomer et al. |
| 2004/0097927 A1 | 5/2004 | Yeung et al. | | 2006/0235452 A1 | 10/2006 | Schomer et al. |
| 2004/0098074 A1 | 5/2004 | Erickson et al. | | 2006/0241648 A1 | 10/2006 | Bleich et al. |
| 2004/0106940 A1 | 6/2004 | Shaolian et al. | | 2006/0264952 A1 | 11/2006 | Nelson et al. |
| 2004/0111084 A1 | 6/2004 | Brett | | 2006/0264994 A1 | 11/2006 | Schomer et al. |
| 2004/0122433 A1 | 6/2004 | Loubens et al. | | 2006/0271080 A1 | 11/2006 | Suddaby |
| 2004/0122482 A1 | 6/2004 | Tung et al. | | 2006/0276720 A1 | 12/2006 | McGinnis et al. |
| 2004/0127893 A1 | 7/2004 | Hovda | | 2006/0276802 A1 | 12/2006 | Vresilovic et al. |
| 2004/0143165 A1 | 7/2004 | Alleyne | | 2006/0276836 A1 | 12/2006 | Bergin et al. |
| 2004/0143280 A1 | 7/2004 | Suddaby | | 2007/0010717 A1 | 1/2007 | Cragg |
| 2004/0162609 A1 | 8/2004 | Hossainy et al. | | 2007/0016097 A1 | 1/2007 | Farquhar et al. |
| 2004/0167444 A1 | 8/2004 | Laroya et al. | | 2007/0016185 A1 | 1/2007 | Tullis et al. |
| 2004/0167553 A1 | 8/2004 | Simpson et al. | | 2007/0027464 A1 | 2/2007 | Way et al. |
| 2004/0181150 A1 | 9/2004 | Evans et al. | | 2007/0027514 A1 | 2/2007 | Gerber |
| 2004/0199084 A1 | 10/2004 | Kelleher et al. | | 2007/0049962 A1 | 3/2007 | Marino et al. |
| 2004/0199159 A1 | 10/2004 | Lee et al. | | 2007/0055215 A1 | 3/2007 | Tran et al. |
| 2004/0220576 A1 | 11/2004 | Sklar | | 2007/0055262 A1 | 3/2007 | Tomita et al. |
| 2004/0225233 A1 | 11/2004 | Frankowski et al. | | 2007/0055263 A1 | 3/2007 | Way et al. |
| 2004/0260358 A1 | 12/2004 | Vaughan et al. | | 2007/0073356 A1 | 3/2007 | Rooney et al. |
| 2005/0027199 A1 | 2/2005 | Clarke | | 2007/0106219 A1 | 5/2007 | Grabinsky |
| 2005/0033393 A1 | 2/2005 | Daglow | | 2007/0123766 A1 | 5/2007 | Whalen, III et al. |
| 2005/0049592 A1 | 3/2005 | Keith et al. | | 2007/0123888 A1 | 5/2007 | Bleich et al. |
| 2005/0149035 A1 | 7/2005 | Pimenta et al. | | 2007/0123890 A1 | 5/2007 | Way et al. |
| 2005/0171587 A1 | 8/2005 | Daglow et al. | | 2007/0162044 A1 | 7/2007 | Marino |
| 2005/0182454 A1 | 8/2005 | Gharib et al. | | 2007/0162061 A1 | 7/2007 | Way et al. |
| 2005/0187537 A1 | 8/2005 | Loeb et al. | | 2007/0162062 A1 | 7/2007 | Norton et al. |
| 2005/0197661 A1 | 9/2005 | Carrison et al. | | 2007/0166345 A1 | 7/2007 | Pavcnik et al. |
| 2005/0203599 A1 | 9/2005 | Garabedian et al. | | 2007/0198019 A1 | 8/2007 | Schomer et al. |
| 2005/0209610 A1 | 9/2005 | Carrison | | 2007/0213583 A1 | 9/2007 | Kim et al. |
| 2005/0209617 A1 | 9/2005 | Koven et al. | | 2007/0213584 A1 | 9/2007 | Kim et al. |
| 2005/0209622 A1 | 9/2005 | Carrison | | 2007/0213733 A1 | 9/2007 | Bleich et al. |
| 2005/0216023 A1 | 9/2005 | Aram et al. | | 2007/0213734 A1 | 9/2007 | Bleich et al. |
| 2005/0222598 A1 | 10/2005 | Ho et al. | | 2007/0213735 A1 | 9/2007 | Saadat et al. |
| 2005/0222647 A1 | 10/2005 | Wahlstrand et al. | | 2007/0213795 A1 | 9/2007 | Bradley et al. |
| 2005/0256423 A1 | 11/2005 | Kirsner | | 2007/0225703 A1 | 9/2007 | Schmitz et al. |
| 2005/0261692 A1 | 11/2005 | Carrison et al. | | 2007/0255162 A1 | 11/2007 | Abboud et al. |
| 2005/0277942 A1 | 12/2005 | Kullas et al. | | 2007/0255369 A1 | 11/2007 | Bonde et al. |
| 2005/0283148 A1 | 12/2005 | Janssen et al. | | 2007/0260252 A1 | 11/2007 | Schmitz et al. |
| 2005/0283204 A1 | 12/2005 | Buhlmann et al. | | 2007/0270795 A1 | 11/2007 | Francischelli et al. |
| 2006/0004369 A1 | 1/2006 | Patel et al. | | 2007/0270865 A1 | 11/2007 | Arnin et al. |
| 2006/0015035 A1 | 1/2006 | Rock | | 2007/0276286 A1 | 11/2007 | Miller |
| 2006/0025702 A1 | 2/2006 | Sterratino et al. | | 2007/0276390 A1 | 11/2007 | Solsberg et al. |
| 2006/0025703 A1 | 2/2006 | Miles et al. | | 2007/0282217 A1 | 12/2007 | McGinnis et al. |
| 2006/0025797 A1 | 2/2006 | Lock et al. | | 2007/0293782 A1 | 12/2007 | Marino |
| 2006/0030854 A1 | 2/2006 | Haines | | 2007/0299403 A1 | 12/2007 | Crowe et al. |
| 2006/0036211 A1 | 2/2006 | Solsberg et al. | | 2007/0299459 A1 | 12/2007 | Way et al. |
| 2006/0036271 A1 | 2/2006 | Schomer et al. | | 2008/0033465 A1 | 2/2008 | Schmitz et al. |
| 2006/0036272 A1 | 2/2006 | Solsberg et al. | | 2008/0051812 A1 | 2/2008 | Schmitz et al. |
| 2006/0058732 A1 | 3/2006 | Harp | | 2008/0058820 A1 | 3/2008 | Harp |
| 2006/0064101 A1 | 3/2006 | Arramon | | 2008/0058874 A1 | 3/2008 | Westlund et al. |
| 2006/0079919 A1 | 4/2006 | Harp | | 2008/0064945 A1 | 3/2008 | Marino et al. |
| 2006/0085048 A1 | 4/2006 | Cory et al. | | 2008/0064976 A1 | 3/2008 | Kelleher et al. |
| 2006/0085049 A1 | 4/2006 | Cory et al. | | 2008/0064977 A1 | 3/2008 | Kelleher et al. |
| 2006/0089633 A1 | 4/2006 | Bleich et al. | | 2008/0065178 A1 | 3/2008 | Kelleher et al. |
| 2006/0089650 A1 | 4/2006 | Nolde | | 2008/0071191 A1 | 3/2008 | Kelleher et al. |
| 2006/0089688 A1 | 4/2006 | Panescu | | 2008/0086034 A1 | 4/2008 | Schmitz et al. |
| 2006/0095028 A1 | 5/2006 | Bleich | | 2008/0086114 A1 | 4/2008 | Schmitz et al. |
| 2006/0095059 A1 | 5/2006 | Bleich et al. | | 2008/0091227 A1 | 4/2008 | Schmitz et al. |
| 2006/0100651 A1 | 5/2006 | Bleich | | 2008/0097465 A1 | 4/2008 | Rollins et al. |
| 2006/0122458 A1 | 6/2006 | Bleich | | 2008/0103504 A1 | 5/2008 | Schmitz et al. |
| 2006/0122620 A1 | 6/2006 | Kim | | 2008/0119711 A1 | 5/2008 | Nikumb et al. |
| 2006/0122653 A1 | 6/2006 | Bradley et al. | | 2008/0125621 A1 | 5/2008 | Gellman et al. |
| 2006/0122654 A1 | 6/2006 | Bradley et al. | | 2008/0125709 A1 | 5/2008 | Chang et al. |
| 2006/0142753 A1 | 6/2006 | Francischelli et al. | | 2008/0140153 A1 | 6/2008 | Burdulis |
| 2006/0149278 A1 | 7/2006 | Abdou | | 2008/0140169 A1 | 6/2008 | Imran |
| 2006/0161189 A1 | 7/2006 | Harp | | 2008/0146867 A1 | 6/2008 | Gellman et al. |
| 2006/0173374 A1 | 8/2006 | Neubardt et al. | | 2008/0147084 A1 | 6/2008 | Bleich et al. |
| 2006/0184175 A1 | 8/2006 | Schomer et al. | | 2008/0161809 A1 | 7/2008 | Schmitz et al. |
| 2006/0195107 A1 | 8/2006 | Jones et al. | | 2008/0161810 A1 | 7/2008 | Melkent |
| 2006/0200153 A1 | 9/2006 | Harp | | 2008/0197024 A1 | 8/2008 | Simpson et al. |
| 2006/0200154 A1 | 9/2006 | Harp | | 2008/0200912 A1 | 8/2008 | Long |
| 2006/0200155 A1 | 9/2006 | Harp | | 2008/0221383 A1 | 9/2008 | Way et al. |
| 2006/0200219 A1 | 9/2006 | Thrope et al. | | 2008/0221586 A1 | 9/2008 | Garcia-Bengochea et al. |
| 2006/0206115 A1 | 9/2006 | Schomer et al. | | 2008/0255439 A1 | 10/2008 | Tang et al. |

| | | | |
|---|---|---|---|
| 2008/0275458 A1 | 11/2008 | Bleich et al. | |
| 2008/0288005 A1 | 11/2008 | Jackson | |
| 2008/0312660 A1 | 12/2008 | Bleich et al. | |
| 2008/0319459 A1 | 12/2008 | Al-najjar | |
| 2009/0018507 A1 | 1/2009 | Schmitz et al. | |
| 2009/0018610 A1 | 1/2009 | Gharib et al. | |
| 2009/0036936 A1 | 2/2009 | Solsberg et al. | |
| 2009/0054804 A1 | 2/2009 | Gharib et al. | |
| 2009/0054936 A1 | 2/2009 | Eggen et al. | |
| 2009/0054941 A1 | 2/2009 | Eggen et al. | |
| 2009/0062871 A1 | 3/2009 | Chin et al. | |
| 2009/0062872 A1 | 3/2009 | Chin et al. | |
| 2009/0069709 A1 | 3/2009 | Schmitz et al. | |
| 2009/0082763 A1* | 3/2009 | Quick et al. | 606/33 |
| 2009/0105604 A1 | 4/2009 | Bertagnoli et al. | |
| 2009/0105788 A1 | 4/2009 | Bartol et al. | |
| 2009/0118709 A1 | 5/2009 | Sand et al. | |
| 2009/0124934 A1 | 5/2009 | Rabbitte et al. | |
| 2009/0138056 A1 | 5/2009 | Anderson et al. | |
| 2009/0143807 A1 | 6/2009 | Sand | |
| 2009/0143829 A1 | 6/2009 | Shluzas | |
| 2009/0149865 A1 | 6/2009 | Schmitz et al. | |
| 2009/0171381 A1 | 7/2009 | Schmitz et al. | |
| 2009/0177112 A1 | 7/2009 | Gharib et al. | |
| 2009/0177144 A1 | 7/2009 | Masmanidis et al. | |
| 2009/0177241 A1 | 7/2009 | Bleich et al. | |
| 2009/0182382 A1 | 7/2009 | Justis et al. | |
| 2009/0192403 A1 | 7/2009 | Gharib et al. | |
| 2009/0204016 A1 | 8/2009 | Gharib et al. | |
| 2009/0204119 A1 | 8/2009 | Bleich et al. | |
| 2009/0209879 A1 | 8/2009 | Kaula et al. | |
| 2009/0216284 A1 | 8/2009 | Chin et al. | |
| 2009/0299166 A1 | 12/2009 | Nishida | |
| 2010/0004654 A1 | 1/2010 | Schmitz et al. | |
| 2010/0010334 A1 | 1/2010 | Bleich et al. | |
| 2010/0057087 A1 | 3/2010 | Cha | |
| 2010/0094231 A1 | 4/2010 | Bleich et al. | |
| 2010/0274250 A1 | 10/2010 | Wallace et al. | |
| 2010/0331883 A1 | 12/2010 | Schmitz et al. | |
| 2011/0004207 A1 | 1/2011 | Wallace et al. | |
| 2011/0046613 A1 | 2/2011 | Schmitz et al. | |
| 2011/0060314 A1 | 3/2011 | Wallace et al. | |
| 2011/0112539 A1 | 5/2011 | Wallace et al. | |
| 2011/0160731 A1 | 6/2011 | Bleich et al. | |
| 2011/0160772 A1 | 6/2011 | Arcenio et al. | |
| 2011/0190772 A1 | 8/2011 | Saadat et al. | |
| 2011/0196257 A1 | 8/2011 | Schmitz et al. | |
| 2011/0224709 A1 | 9/2011 | Bleich | |
| 2011/0224710 A1 | 9/2011 | Bleich | |
| 2012/0016368 A1 | 1/2012 | Bleich et al. | |
| 2012/0022538 A1 | 1/2012 | Schmitz et al. | |
| 2012/0065639 A1 | 3/2012 | Schmitz et al. | |
| 2012/0078255 A1 | 3/2012 | Bleich et al. | |
| 2012/0095468 A1 | 4/2012 | Wallace et al. | |
| 2012/0123294 A1 | 5/2012 | Sun et al. | |
| 2012/0143206 A1 | 6/2012 | Wallace et al. | |

FOREIGN PATENT DOCUMENTS

| | | |
|---|---|---|
| EP | 359883 A1 | 3/1990 |
| EP | 1304080 A2 | 4/2003 |
| EP | 1340467 A2 | 9/2003 |
| EP | 1207794 B1 | 5/2004 |
| EP | 1315463 B1 | 5/2005 |
| EP | 1611851 A1 | 1/2006 |
| EP | 1006885 B1 | 9/2006 |
| FR | 2706309 | 12/1994 |
| JP | 2960140 B2 | 10/1999 |
| JP | 23116868 | 4/2003 |
| JP | 24065380 A2 | 3/2004 |
| RU | 2107459 | 3/1998 |
| WO | WO92/22259 A2 | 12/1992 |
| WO | WO-96/22057 | 7/1996 |
| WO | WO97/14362 A1 | 4/1997 |
| WO | WO-97/34536 A2 | 9/1997 |
| WO | WO-99/18866 A1 | 4/1999 |
| WO | WO-99/21500 A1 | 5/1999 |
| WO | WO-00/67651 A1 | 11/2000 |
| WO | WO-01/08571 A1 | 2/2001 |
| WO | WO-01/62168 A2 | 8/2001 |
| WO | WO-02/07901 A1 | 1/2002 |
| WO | WO-02/34120 A2 | 5/2002 |
| WO | WO-02/076311 A2 | 10/2002 |
| WO | WO-03/026482 A2 | 4/2003 |
| WO | WO-03/066147 A1 | 8/2003 |
| WO | WO-2004/002331 A1 | 1/2004 |
| WO | WO-2004/028351 A2 | 4/2004 |
| WO | WO-2004/043272 A1 | 5/2004 |
| WO | WO-2004/056267 A1 | 7/2004 |
| WO | WO-2004/078066 A2 | 9/2004 |
| WO | WO-2004/080316 A1 | 9/2004 |
| WO | WO-2004/096080 A2 | 11/2004 |
| WO | WO-2005/009300 A1 | 2/2005 |
| WO | WO-2005/057467 A2 | 6/2005 |
| WO | WO-2005/077282 A1 | 8/2005 |
| WO | WO-2005/089433 A2 | 9/2005 |
| WO | WO-2006/009705 A2 | 1/2006 |
| WO | WO-2006/015302 A1 | 2/2006 |
| WO | WO-2006/017507 A2 | 2/2006 |
| WO | WO-2006/039279 A2 | 4/2006 |
| WO | WO-2006/042206 A2 | 4/2006 |
| WO | WO-2006/044727 A2 | 4/2006 |
| WO | WO-2006/047598 A1 | 5/2006 |
| WO | WO-2006/058079 A3 | 6/2006 |
| WO | WO-2006/058195 A2 | 6/2006 |
| WO | WO-2006/062555 A2 | 6/2006 |
| WO | WO-2006/086241 A2 | 8/2006 |
| WO | WO-2006/099285 A2 | 9/2006 |
| WO | WO-2006/102085 A2 | 9/2006 |
| WO | WO-2007/008709 A2 | 1/2007 |
| WO | WO-2007/021588 A1 | 2/2007 |
| WO | WO-2007/022194 A2 | 2/2007 |
| WO | WO-2007/059343 A2 | 2/2007 |
| WO | WO-2007/067632 A2 | 6/2007 |
| WO | WO-2008/008898 A2 | 1/2008 |
| WO | WO-2008/157513 A1 | 12/2008 |
| WO | WO-2009/012265 A2 | 1/2009 |
| WO | WO-2009/018220 A1 | 2/2009 |
| WO | WO-2009/021116 A2 | 2/2009 |
| WO | WO-2009/036156 A1 | 3/2009 |
| WO | WO-2009/046046 A1 | 4/2009 |
| WO | WO-2009/058566 A1 | 5/2009 |
| WO | WO-2009/151926 A2 | 12/2009 |
| WO | WO-2010/014538 | 4/2010 |

OTHER PUBLICATIONS

Wallace et al.; U.S. Appl. No. 12/724,315 entitled "Flexible Neural Localization Devices and Methods," filed Mar. 15, 2010.

Wallace et al.; U.S. Appl. No. 12/773,595 entitled "Tissue Modification Devices and Methods," filed May 4, 2010.

Edwards et al; "T-Saw Laminoplasty for the Management of Cervical Spondylotic Myelopathy," SPINE, Lippincott Williams & Wilkins, Inc., 2000, vol. 25 (14): 1788-1794. Jan. 1, 2000.

Honl et al; "The Use of Water-Jetting Technology in Prostheses Revision Surgery—First Results of Parameter Studies on Bone and Bone Cement," J. Biomed Mater Res (Applied Biomaterials), John Wiley & Sons, Inc, 2000, 53, 6: 781-790. Jan. 1, 2000.

Jun, Byung-Yoon, "Posterior Lumbar Interbody Fusion With Restoration of Lamina and Facet Fusion," SPINE, Lippincott Williams & Wilkins, Inc., 2000, vol. 25 No. 8, 917-922. Jan. 1, 2000.

Abdel-Wanis et al., "Tumor growth potential after tumoral and instrumental contamination: an in-vivo comparative study of T-saw, Gigli saw, and scalpel," Journal of orthopaedic science, 2001, vol. 6, 424-429. Jan. 1, 2001.

Codman Laminectomy Shaver (a Johnson & Johnson company www.codman.com) catalogue, pp. 416-431, [online] Retrieved from the internet: <URL: http://www.codman.com/PDFs/Catalog_04_R.pdf>. Jan. 1, 2001.

Ellman Int. Disc-FX System Accessories K052241 [online] Retrieved from the Internet: <URL: http://www.ellman.com/ medical/>. Jan. 1, 2001.

Hara et al., "En Bloc Laminoplasty Performed with Threadwire Saw: Technical Note," Neurosurgery, Jan. 2001, vol. 48, No. 1, pp. 235-239. Jan. 1, 2001.

Hata et al; "A less invasive surgery for rotator cuff tear: Mini-open repair," Journal of Shoulder and Elbow Surgery, 2001, vol. 10 No. 1, 11-16. Jan. 1, 2001.

Integra Ruggles TM Kerrison Rongeurs [online] Retrieved from the internet: <URL: http://www.integra-ls.com/products!?product=22>. Jan. 1, 2001.

Mopec Bone-Cutting tool, Product brochure, Total pp. 4. Jan. 1, 2001.

US Surgical Kerrison Spinal Rongeur K943116 [online] Retrieved from the internet: <URL: http://www.ussurg.com/uss/index.html>. Jan. 1, 2001.

Zeppelin Laminectomy Rongeur K901372, [online] Retrieved from the internet: <URL: http://www.zeppelin-medical.com/download/instruments.pdf>. Jan. 1, 2001.

Sen, Cengiz, Tibia proksimalinde Gigli testeresi ile yapilanperkütan osteotominin güvenilirligi: Kadavra calismasi, Acta orthopaedica et traumatologica turcica, 2002, vol. 36, 136-140; (In Russian w/ Eng Summary). Jan. 1, 2002.

Shiraishi T., "A new technique for exposure of the cervical spine laminae," Journal of neurosurgery. Spine, 2002, vol. 96(1), 122-126. Jan. 1, 2002.

Shiraishi T., Skip laminectomy—a new treatment for cervical spondylotic myelopathy, preserving bilateral muscular attachments to the spinous processes: a preliminary report, Spine, 2002, vol. 2(2), 108-115. Jan. 1, 2002.

Tomita et al., "The Use of the T-Saw for Expansive Midline laminoplasty in the Treatment of Cervical Myelopathy," Orthopedics and Traumatology, No. 3, pp. 169-178, Jan. 1, 2002.

Martin-Benlloch et al., "Expansive Laminoplasty as a Method for Managing Cervical Multilevel Spondylotic Myelopathy," Spine, Lippincott Williams & Wilkins, Inc., 2003, vol. 28 No. 7, 680-684. Jan. 1, 2003.

Miyamoto et al., "Kyphectomy Using a Surgical Threadwire (T-saw) for Kyphotic Deformity in a Child With Myelomeningocele," SPINE, Lippincott Williams & Wilkins, Inc., 2003, vol. 28 No. 10, E187—E190. Jan. 1, 2003.

Shiraishi et al., "Results of Skip Laminectomy—Minimum 2-Year Follow-up Study Compared With Open-Door Laminoplasty," Spine, Lippincott Williams & Wilkins, Inc., 2003, vol. 28 No. 24, 2667-2672. Jan. 1, 2003.

Takada et al., "Unusual Metastasis to the Cauda Equina From Renal Cell Carcinoma," SPINE, Lippincott Williams & Wilkins, Inc., 2003, vol. 28 No. 6, E114-E117. Jan. 1, 2003.

Eralp et al., "A comparison of two osteotomy techniques for tibial lengthening," Archives of orthopaedic and trauma surgery, 2004, vol. 124:298-300. Jan. 1, 2004.

Skippen et al., "The Chain Saw—A Scottish Invention," Scottish Medical Journal, 2004, vol. 49(2), 72-75. Jan. 1, 2004.

Bohinski et al., "Novel use of a threadwire saw for high sacral amputation," Journal of neurosurgery: Spine, 2005, vol. 3, 71-78. Jan. 1, 2005.

Nakagiri et al., "Thoracoscopic Rib Resection Using a Gigli Saw," The Annals of Thoracic Surgery, 2005, vol. 80, 755-756. Jan. 1, 2005.

Osaka et al., "Clinical significance of a wide excision policy for sacrococcygeal chordoma," J Cancer Res Clin Oncol, 2005, Total pp. 6. Jan. 1, 2005.

Fessler Richard G, "Minimally Invasive Microendoscopic Decompressive Laminotomy for Lumbar Stenosis," American Association of Neurological Surgeons, 2006, Online CME course, [Retrieved on Jun. 29, 2006 from the internet http://www.aans.emedtrain.com/lumbar_ste Jan. 1, 2006.

Park et al; "Cases of the Excision of Carious Joints," John Scrymgeour, Glasgow, 1806, Total pp. 6. Jan. 1, 1806.

Pancoast, Joseph, "A Treatise on Operative Surgery," Carey and Hart, Philadelphia,1844, Total pp. 11. Jan. 1, 1844.

Truax, Charles, "The Mechanics of Surgery," Chicago, IL; 1899, Total pp. 3. Jan. 1, 1899.

Burrows, Harold, "Surgical instruments and appliances used in operations," Faber and Faber, London, 1937, total pp. 4. Jan. 1, 1937.

Wilkins, Robert H, "Neurosurgical Classics," Johnson Reprint Corporation, New York, 1965, 377-382. Jan. 1, 1965.

Dammann, Gordon, Pictorial Encyclopedia of Civil War Medical Instruments and Equipment, Pictorial Histories Publishing Company, Missoula, Montana, 1983, Total pp. 2. Jan. 1, 1983.

Barer Malvin, "Instrument to Enhance Passage of the Gigli Saw," Journal of Pediatric Orthopedics, Raven Press, New York, 1984, 4:762-763. Jan. 1, 1984.

Paley et al., "Percutaneous Osteotomies," Orthopedic Clinics of North America, 1991, vol. 22 No. 4, 613-624. Jan. 1, 1991.

Paktiss et al., "Afghan Percutaneous Osteotomy," Journal of Pediatric Orthopaedics, Raven Press Ltd, New York, 1993, vol. 13 No. 4, 531-533. Jan. 1, 1993.

Peltier, Leonard Orthopedics: A History and Iconography, Norman Publishing, San Francisco, 1993, Total pp. 3. Jan. 1, 1993.

Rutkow, Ira, "Surgery An Illustrated History," Mosby—Year Book, Inc., St. Louis, 1993, Total pp. 4. Jan. 1, 1993.

Goel, Atul, "Neurosurgical forum, Supraorbital Craniotomy," Journal of Neurosurgery, 1994, vol. 81, 642-643. Jan. 1, 1994.

Tomita et al., "Total en bloc spondylectomy and circumspinal decompression for solitary spinal metastasis," Paraplegia, 1994, 32:36-46. Jan. 1, 1994.

Tomita K. et al., "Total en bloc spondylectomy for solitary spinal metastases," International Orthopaedics (SICOT), 1994, 18: 291-298. Jan. 1, 1994.

Brunori et al., "Celebrating the centennial (1894-1994): Leonardo Gigli and his wire saw," J. Neurosurg, 1995, 82:1086-1090. Jan. 1, 1995.

Tomita et al., "The Threadwire Saw: a New Device for Cutting Bone," The Journal of Bone and Joint Surgery, 1996, vol. 78, 1915-1917. Jan. 1, 1996.

Baumgart et al., "Indikation and Technik der Knochendurchtrennung," Der Chirurg, 1998, vol. 69:1188-1196. (in German with Eng Summary). Jan. 1, 1998.

Stevens et al., "Calvarial Bone Graft Harvest Using the Gigli Saw," Journal of Oral and Maxillofacial Surgery, 1998, vol. 56, 798-799. Jan. 1, 1998.

Tomita et al., "Expansive Midline T-Saw Laminoplasty (Modified Spinour Process-Splitting) for the Management of Cervical Myelopathy," SPINE, Lippincott Williams & Wilkins, Inc, 1998, 23(1), 32-37. Jan. 1, 1998.

Fujita et al., "Chordoma in the Cervical Spine Managed with En Bloc Excision," SPINE, Lippincott Williams & Wilkins, Inc., 1999, 24 (17), 1848-1851. Jan. 1, 1999.

Gore Smoother User Manual, W. L. Gore & Associates, Inc. Flagstaff, AZ, Dec. 1999, Total pp. 3. Jan. 1, 1999.

Kawahara et al., "Recapping T-Saw Laminoplasty for Spinal Cord Tumors," SPINE, 1999, vol. 24 No. 13, pp. 1363-1370. Jan. 1, 1999.

Peavy et al., "Comparison of Cortical Bone Ablations by Using Infrared Laser Wavelengths 2.9 to 9.2 µm, Lasers in Surgery and Medicine," 1999, vol. 26, 421-434. Jan. 1, 1999.

Reckling Frederick, "Modified Stethoscope Earpiece Makes Excellent Gigli Saw Guide," J Bone and Joint Surgery Am, Dec. 1972, 54-A(8), 1787-1788. Dec. 1, 1972.

Arcenio et al.; U.S. Appl. No. 12/980,165 entitled "Systems and Methods for Performing Spinal Fusion", filed Dec. 28, 2010.

Bleich et al.; U.S. Appl. No. 12/984,162 entitled "Devices and Methods for Tissue Access", filed Jan. 4, 2011.

Schmitz et al.; U.S. Appl. No. 12/917,253; entitled "Tissue Access Guidewire System and Method"; filed Nov. 1, 2010.

Wallace et al.; U.S. Appl. No. 12/911,537 entitled "Devices and Methods for Treating Tissue", filed Oct. 25, 2010.

Wallace et al.; U.S. Appl. No. 13/007,381 entitled "Tissue Modification Devices", filed Jan. 14, 2011.

Bleich et al.; U.S. Appl. No. 13/484,744 entitled "Devices and Methods for Tissue Modification," filed May 31, 2012.

Bleich et al.; U.S. Appl. No. 13/430,500 entitled "Devices and Methods for Tissue Modification," filed Mar. 26, 2012.

Garabedian et al.; U.S. Appl. No. 13/437,214 entitled "Flexible Tissue Rasp," filed Apr. 2, 2012.

US Surgical Kerrison Spinal Rongeur K943116 [online] Retrieved from the Internet: <URL: http://www.ussurg.com/uss/index.html>. Jul. 27, 1994.

Zeppelin Laminectomy Rongeur K901372, [online] Retrieved from the Internet: <URL: http://www.zeppelin-medical.com/download/instruments.pdf>. Oct. 24, 2006.

Ellman Int. Disc-FX System Accessories K052241 [online] Retrieved from the Internet: <URL: http://www.ellman.com/ medical/ >. Feb. 27, 2006.

Ohta et al., "Superimposed Mechanomygraphic Response at Different Contraction Intensity in Medial Gastrocnemius and Soleus Muscles," International Journal of Sport and Health Science: vol. 5, 63-70, 2007.

Schwieger et al., "Abrasive Water Jet Cutting as a New Procedure for Cutting Cancellous Bone—In Vitro Testing in Comparison with the Oscillating Saw," Wiley Interscience, www.interscience,wiley.com, Sep. 20, 2004, 223-228.

Mopec Bone-Cutting tool, Product brochure, Total pp. 4. First accessed Dec. 15, 2005.

Codman Laminectomy Shaver (a Johnson & Johnson company www.codman.com) catalogue, pp. 416-431, [online] Retrieved from the Internet: <URL: http:IIwww.codman.com/PDFs/Catalog_04_R.pdf >. First accessedOct. 24, 2006.

Integra Ruggles TM Kerrison Rongeurs [online] Retrieved from the internet: <URL: http://www.integra-ls.com/products!?product=22>. First accessedOct. 24, 2006.

Herkowitz, "The Cervical Spine Surgery Atlas", *Herkowitz, "The Cervical Spine Surgery Atlas"*, 2004, 2nd Edition Jan. 1, 2004 , 203-206, 208.

\* cited by examiner

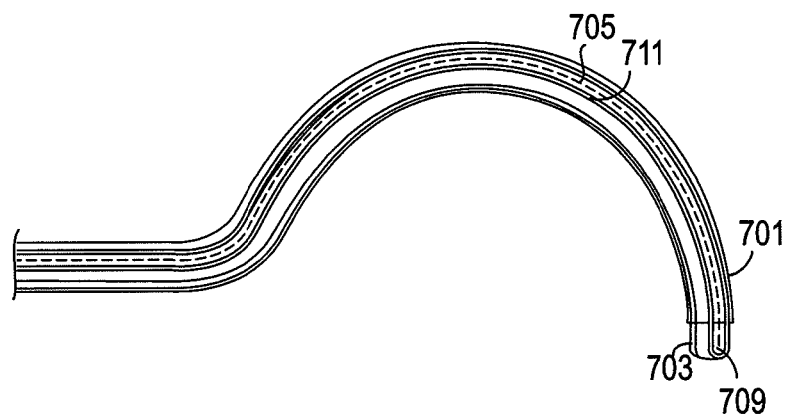
FIG. 7A
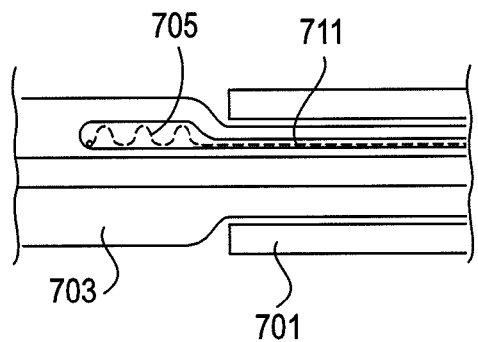
FIG. 7B
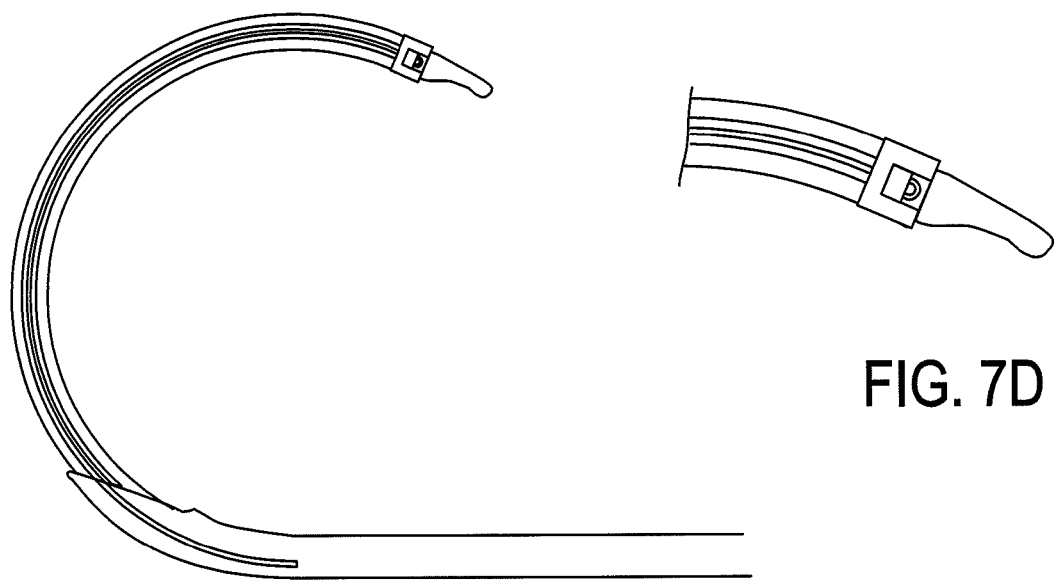
FIG. 7D
FIG. 7C

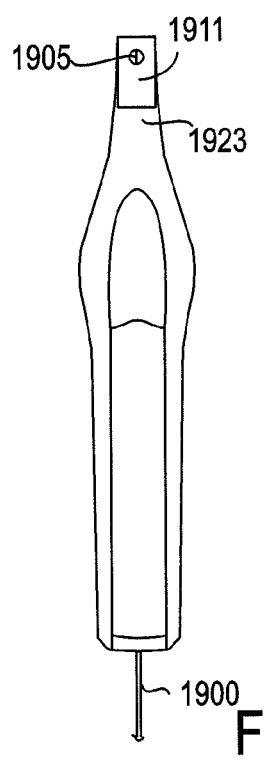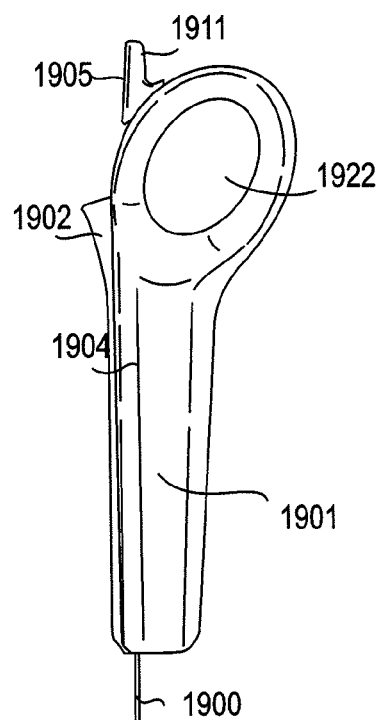
FIG. 16A    FIG. 16B
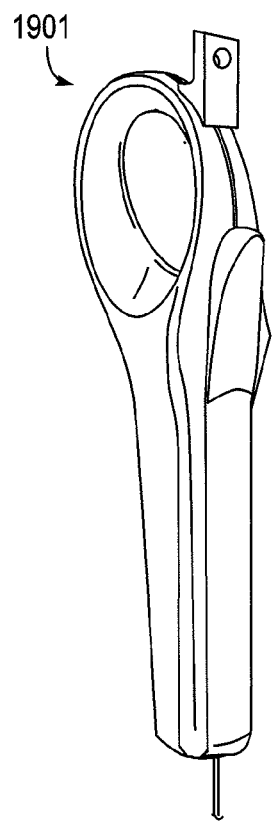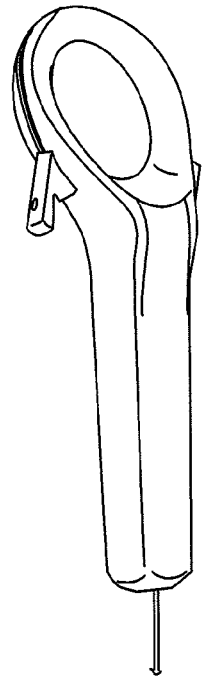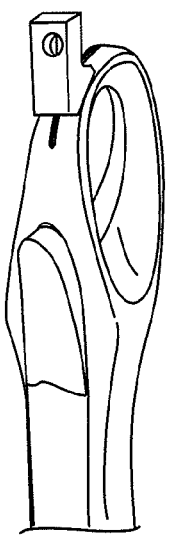
FIG. 17A    FIG. 17B    FIG. 17C

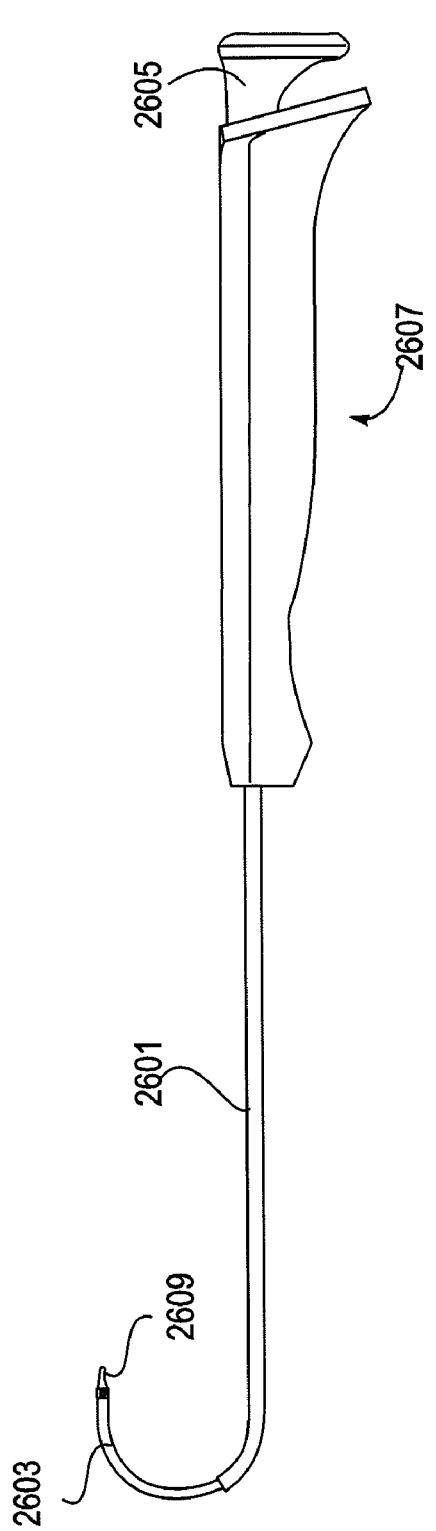
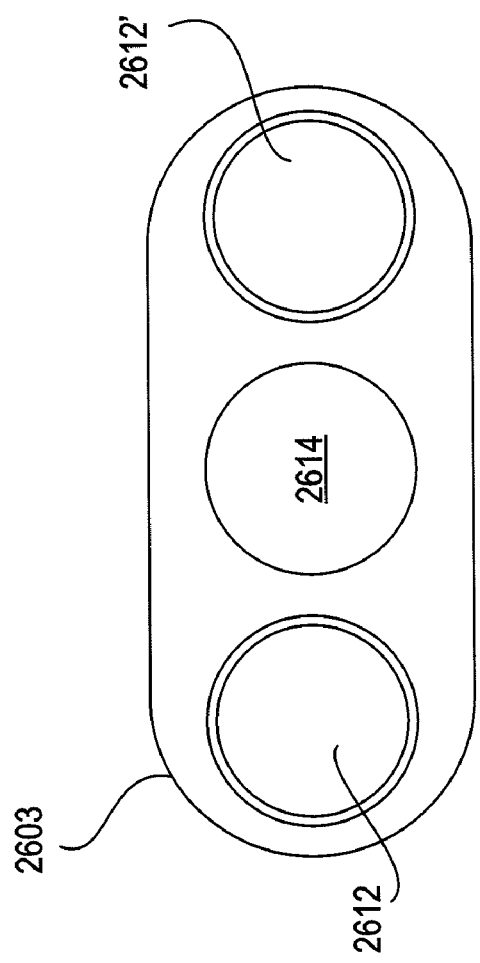
FIG. 29A
FIG. 29B

SURGICAL TOOLS FOR TREATMENT OF SPINAL STENOSIS

CROSS REFERENCE TO RELATED APPLICATIONS

This patent application claims priority to U.S. Provisional Application No. 61/220,314, titled "SURGICAL TOOLS FOR TREATMENT OF SPINAL STENOSIS", filed on Jun. 25, 2009 and U.S. Provisional Application No. 61/253,811, titled "SURGICAL TOOLS FOR TREATMENT OF SPINAL STENOSIS", filed on Oct. 21, 2009. These patent applications are each incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD OF THE INVENTION

Described herein are systems, devices, and methods for performing surgical procedures. In particular, described herein are systems, devices and methods for spinal decompression procedures.

BACKGROUND OF THE INVENTION

In recent years, less invasive (or "minimally invasive") surgical techniques have become increasingly more popular, as physicians, patients and medical device innovators have sought to achieve similar or improved outcomes, relative to conventional surgery, while reducing the trauma, recovery time and side effects typically associated with conventional surgery. Developing less invasive surgical methods and devices, however, can pose many challenges. For example, some challenges of less invasive techniques include working in a smaller operating field, working with smaller devices, and trying to operate with reduced or even no direct visualization of the structure (or structures) being treated. These challenges are compounded by the fact that target tissues to be modified often reside very close to one or more vital, non-target tissues, which the surgeon hopes not to damage. One of the initial obstacles in any given minimally invasive procedure, therefore, is positioning a minimally invasive surgical device in a desired location within the patient to perform the procedure on one or more target tissues, while avoiding damage to nearby non-target tissues.

Examples of less invasive surgical procedures include laparoscopic procedures, arthroscopic procedures, and minimally invasive approaches to spinal surgery, such as a number of less invasive intervertebral disc removal, repair and replacement techniques. One area of spinal surgery in which a number of less invasive techniques have been developed is the treatment of spinal stenosis. Spinal stenosis occurs when neural and/or neurovascular tissue in the spine becomes impinged by one or more structures pressing against them, causing one or more symptoms. This impingement of tissue may occur in one or more of several different areas in the spine, such as in the central spinal canal, or more commonly in the lateral recesses of the spinal canal and/or one or more intervertebral foramina.

One common cause of spinal stenosis is buckling and thickening of the ligamentum flavum (one of the ligaments attached to and connecting the vertebrae). Buckling or thickening of the ligamentum flavum may impinge on one or more neurovascular structures, dorsal root ganglia, nerve roots and/or the spinal cord itself. Another common cause of neural and neurovascular impingement in the spine is hypertrophy of one or more facet joints (or "zygopophaseal joints"), which provide articulation between adjacent vertebrae. Vertebral facet superior articular processes articulate with inferior articular processes of adjacent vertebra to form zygopophaseal joints. Other causes of spinal stenosis include formation of osteophytes (or "bone spurs") on vertebrae, spondylolisthesis (sliding of one vertebra relative to an adjacent vertebra), facet joint synovial cysts, and collapse, bulging or herniation of an intervertebral disc into the central spinal canal. Disc, bone, ligament or other tissue may impinge on the spinal cord, the cauda equina, branching spinal nerve roots and/or blood vessels in the spine to cause loss of function, ischemia and even permanent damage of neural or neurovascular tissue. In a patient, this may manifest as pain, impaired sensation and/or loss of strength or mobility.

In the United States, spinal stenosis occurs with an incidence of between 4% and 6% of adults aged 50 and older and is the most frequent reason cited for back surgery in patients aged 60 and older. Conservative approaches to the treatment of symptoms of spinal stenosis include systemic medications and physical therapy. Epidural steroid injections may also be utilized, but they do not provide long lasting benefits. When these approaches are inadequate, current treatment for spinal stenosis is generally limited to invasive surgical procedures to remove ligament, cartilage, bone spurs, synovial cysts, cartilage, and bone to provide increased room for neural and neurovascular tissue. The standard surgical procedure for spinal stenosis treatment includes laminectomy (complete removal of the lamina of one or more vertebrae) or laminotomy (partial removal of the lamina), followed by removal (or "resection") of the ligamentum flavum. In addition, the surgery often includes partial or occasionally complete facetectomy (removal of all or part of one or more facet joints). In cases where a bulging intervertebral disc contributes to neural impingement, disc material may be removed surgically in a discectomy procedure.

Removal of vertebral bone, as occurs in laminectomy and facetectomy, often leaves the effected area of the spine very unstable, leading to a need for an additional highly invasive fusion procedure that puts extra demands on the patient's vertebrae and limits the patient's ability to move. In a spinal fusion procedure, the vertebrae are attached together with some kind of support mechanism to prevent them from moving relative to one another and to allow adjacent vertebral bones to fuse together. Unfortunately, a surgical spine fusion results in a loss of ability to move the fused section of the back, diminishing the patient's range of motion and causing stress on the discs and facet joints of adjacent vertebral segments. Such stress on adjacent vertebrae often leads to further dysfunction of the spine, back pain, lower leg weakness or pain, and/or other symptoms. Furthermore, using current surgical techniques, gaining sufficient access to the spine to perform a laminectomy, facetectomy and spinal fusion requires dissecting through a wide incision on the back and typically causes extensive muscle damage, leading to significant post-operative pain and lengthy rehabilitation. Discectomy procedures require entering through an incision in the patient's abdomen and navigating through the abdominal anatomy to arrive at the spine. Thus, while laminectomy, facetectomy, discectomy, and spinal fusion frequently improve symptoms of neural and neurovascular impingement in the short term, these procedures are highly invasive, diminish spinal function, drastically disrupt normal anatomy, and increase long-term morbidity above levels seen in untreated patients. Although a number of less invasive techniques and devices for spinal stenosis surgery have been developed, these techniques still typically require removal of significant amounts of vertebral bone and, thus, typically require spinal fusion.

Recently, less invasive surgical methods and systems for treating spinal stenosis have been developed, including. For example, devices or systems for positioning less invasive devices in a patient for performing a less invasive procedure using pullwires have been developed. In particular, sharp-tipped (e.g., with tissue-penetrating distal ends) may be inserted from a first location, pass through the tissue (e.g., through or adjacent to a compressed spinal neural foramen), and extend back out of the tissue. The pull wire may then be used to pull one devices (e.g., tissue modification devices, neural localization devices, etc.) into position and also to activate them—e.g., articulating them by pulling them back and forth. In some instances, the forces required to pull the pullwire for positioning or articulating a device coupled to the end of the pullwire may exceed be quite large (e.g., exceeding 10 pounds of force), making the pullwire difficult to grip. In addition, the distal end of the pullwire, which may be sharp, may present a hazard to the surgeon or others performing the procedure. Thus, it would be particularly useful to provide systems for performing the procedures described above that include components such as distal handles that address some of these concerns. At least some of these objectives will be met by the present invention.

Described herein are surgical systems, device and methods that may be particularly useful for treating spinal stenosis.

SUMMARY OF THE INVENTION

In general, the systems for treating spinal stenosis, include a pullwire, a removable distal handle for a pullwire, a probe for inserting a pullwire around a target tissue, a tissue modification device for coupling to the proximal end of a pullwire, and a neural localization device for coupling to the proximal end of a pullwire. The tissue modification device, neural localization device, and probe devices may be similarly adapted for use as a system, and in particular may be adapted to indicate the orientation of the devices and to prevent rotation of the devices during operation. For example, these devices may include a handle having a front and back that is marked.

A pullwire may also be referred to as a guidewire (and thus a pullwire handle may be referred to as a guidewire handle).

For example, described herein are systems for treating spinal stenosis that include: a pullwire having a tissue-penetrating distal end; a cannulated probe comprising a curveable inner cannula that is slideably disposed within a curved outer cannula, the cannulated probe configured for positioning the pullwire around a target tissue; a removable handle configured to secure the distal end of the pullwire; and a tissue modification device configured to couple to the proximal end of the pullwire; wherein the tissue modification device and the cannulated probe both include a proximal handle having a flat front and further wherein the front is marked to indicate the front orientation.

The system may also include a neural localization device that is elongate and flexible and is configured to couple to the proximal end of the pullwire.

In some variations, the flat front of the proximal handles of the cannulated probe and the tissue modification device are marked by one or more of a color or texture.

Also described herein are probes for positioning a pullwire around a target tissue, the probe comprising: an outer cannula having a curved distal region; an inner cannula slideably disposed within the outer cannula, wherein the inner cannula is configured to assume a curved shape when extended distally from the outer cannula; and a proximal handle comprising a hand grip region coupled to the outer cannula and a plunger region coupled to the inner cannula; wherein the proximal end of the plunger region comprises a funneled port for insertion of a pullwire through the probe.

The hand grip region of the proximal handle may comprise a flat front face configured to allow sighting down the length of the probe. The front face of the hand grip region may be marked to indicate the front. For example, the marking may comprise a texture and/or a color.

In some variations, the hand grip region of the proximal handle may comprise a concave region configured to allow the hand grip region to be held like a pencil.

The hand grip region may include a flared distal end configured to facilitate the application of force. The device may also include depth markings on the plunger region of the proximal handle. The hand grip region of the proximal handle may also be keyed to prevent rotation of the probe during use.

Also described herein are neural localization devices including: a flexible, elongate, ribbon-shaped body extending distally, wherein the body comprises a front side and a back side; a distal pullwire coupling member configured to couple to the proximal end of a pullwire; a first electrode coupled to the front side of the elongate, ribbon-shaped body and configured to stimulate adjacent nerve tissue; a second electrode coupled to the back side of the elongate, ribbon-shaped body and configured to stimulate adjacent nerve tissue; and a proximal handle coupled to the body, the handle having a front and a back and comprising a control for activating either the first or second electrode; the handle further comprising an indicator on both the front and back of the handle to indicate activation of either the first or second electrodes.

In some variations, the proximal handle may include a marking indicating the front of the handle. The marking may be a texture and/or a color. In some variations, the proximal handle is keyed to prevent rotation of the device during use.

Also described are tissue modification devices for removing tissue that include: an elongate body having a flexible tissue modification region, wherein the tissue modification region comprises a plurality of blades; a distal pullwire coupling member configured to couple to the proximal end of a pullwire; and a proximal handle coupled to the elongate body, the handle having a front and back side, and comprising one or more markings to distinguish the front and back sides; wherein the proximal handle is keyed to prevent rotation of the device during use.

The proximal handle may be marked to indicate the orientation of the blades at the distal end of the device. The proximal handle may include a flared proximal end to enhance grip and provide leverage.

In some variations, the tissue modification region may be substantially ribbon-shaped, having a front and a back corresponding to the front and the back of the proximal handle. The markings may comprise a texture and/or a color. The proximal handle may be further marked to indicate the size or caliber of the tissue modification device.

Also described herein are pullwire handle devices for securing to the distal end of a tissue-penetrating pullwire that include: a handle body; a pullwire tip capture region (e.g., lever, chamber, etc.) configured to secure to a pullwire and to slideably move relative to the handle body for choking up on the pullwire within the handle body; a pullwire lock configured to lock the pullwire within the handle; and a wire capture indicator configured to indicate when a wire has been secured in the handle. In some variations, the devices further include a funnel-shaped pullwire feed region configured for inserting the distal end of a pullwire within the handle body.

The pullwire lock may comprise a button or lever configured to active and/or inactivate the lock. In some variations, the device includes an internal track for guiding the movement of the pullwire within the handle body.

The wire capture indicator may comprise a window showing a portion of a captured pullwire.

Also described herein are methods of capturing a pullwire using a pullwire handle device configured to secure to the distal end of a pullwire including the steps of inserting the distal end of a pullwire into the pullwire handle device; engaging the distal end of the pullwire with a pullwire tip capture region on the pullwire handle device; locking the pullwire within the handle; and indicating that a pullwire has been secured within the pullwire handle device. The pullwire handle may be moved along (or relative to) the pullwire after the distal tip region of the pullwire has been secured in the tip capture region (e.g., to "choke up" on the pullwire). The handle may then be locked down to secure the two together to prevent further relative movement between the two, although in some variations, the handle may be locked down onto the pullwire by activating a control (e.g., button, lever, etc.) but activated to secure together more tightly by pulling the pullwire slightly relative to the handle to further lock them together. An additional slight movement of the pullwire relative to the handle thus tightens the lock between the two (e.g., by a camming mechanism).

Securing the distal end of the pullwire, which may be sharp, in the handle may allow the handle and pullwire to be manipulated more safely, preventing injury to the surgeon or others from the distal tip.

In some variations, the method also includes the step of sliding the pullwire handle distally to choke up on the pullwire within the body of the pullwire handle device.

The method may also include the step of pushing a button to lock the pullwire within the handle.

In some variations, the step of inserting the distal end of the pullwire into the pullwire handle device may include inserting the distal end of the pullwire into the funnel-shaped proximal end of the pullwire handle device. The step of indicating that the pullwire has been secured within the pullwire handle device may include displaying a portion of the pullwire through a window on the pullwire handle device.

Described herein are pullwire handle devices for securing to the distal end of a tissue-penetrating pullwire that include a handle body, a pullwire lock configured to removably lock onto a portion of a pullwire within the handle, and a storage region configured to store a portion of the pullwire within the handle. In some embodiments, the device may further include a funnel-shaped pullwire feed region configured for inserting the distal end of a pullwire within the handle body. In some embodiments, the device may further include an internal track for guiding the movement of the pullwire within the handle body.

In some embodiments, the pullwire lock may comprise a cam surface coupled to a clamp configured to lock the pullwire within the handle. In some embodiments, the pullwire lock may comprise a button, coupled to a lever arm configured to inactivate the lock and the lever arm may include a cam surface configured to activate and inactivate the lock.

In some embodiments, the pullwire lock is configured to lock the pullwire such that the pullwire handle can be locked to the pullwire, and the handle can be pulled to pull the pullwire so that it transmits between 10 and 60 pounds without the handle slipping, while in some embodiments, the pullwire lock is configured to lock the pullwire such that the pullwire can transmit over 50 pounds without slipping relative to the handle.

In some embodiments, the storage region includes a cone surface that functions to guide the pullwire into the storage region such that the pullwire buckles and is wound within the storage region.

Also described herein are methods of capturing a pullwire using a pullwire handle device configured to secure to the distal region of a pullwire. In some embodiments the method includes the steps of inserting the distal end of a pullwire into the pullwire handle device, storing a portion of the pullwire within the pullwire handle device, and activating the pullwire lock to lock the pullwire within the handle.

In some embodiments, the step of inserting the distal end of the pullwire into the pullwire handle device comprises inserting the distal end of the pullwire into the funnel-shaped proximal end of the pullwire handle device. The method of securing the pullwire and the handle together may include a step of inactivating a pullwire lock configured to lock the pullwire within the handle, prior to the inserting step. In some embodiments, the activating step includes rotating a cam surface against a pullwire, wherein the cam is configured to lock the pullwire within the handle.

As mentioned, the activating step may further include activating the pullwire lock such that the locked pullwire can transmit between 10 and 60 pounds without slipping, while in some embodiments, the activating step further includes activating the pullwire lock such that the locked pullwire can transmit over 50 pounds without slipping.

Also described herein are methods of treating a patient using the handle devices for securing to the distal end of a tissue-penetrating pullwire.

Also described herein are pullwire handle devices for securing to a tissue-penetrating pullwire. In some embodiments, the device includes a handle body, a pullwire lock configured to removably lock the pullwire handle device onto a pullwire within the handle body, and a tip containment element configured to retain the distal tip of the pullwire. In some embodiments, the handle body further comprises a storage chamber configured to store a distal portion of the pullwire.

In some embodiments, a pullwire handle device for securing to a tissue-penetrating pullwire includes a pullwire storage chamber configured to store a distal portion of the pullwire, and an internal track for guiding the pullwire into the pullwire storage chamber. The pullwire handle device may be configured to removably lock the pullwire handle device onto a pullwire. In some embodiments, the handle body further includes a pullwire feed region configured to receive the distal portion of the pullwire.

In some embodiments, a pullwire handle device for securing to a tissue-penetrating pullwire includes a handle body, and a pullwire lock configured to removably lock the pullwire handle device to a pullwire. In some embodiments, the pullwire lock includes a clamp plate and a cam surface configured to apply a force to push the clamp plate to lock the pullwire within the pullwire handle device. In some embodiments, the handle body further comprises a storage chamber configured to store a distal portion of the pullwire.

In some embodiments, the storage chamber includes a cone surface that functions to guide the pullwire into the storage chamber such that the region of the pullwire within the handle buckles (or bends) and is stored within the storage chamber. In some embodiments, the storage chamber includes a slot that may be configured to allow a portion of the pullwire to pass through the slot and out of the storage chamber. In some embodiments, the device further includes a pullwire guide configured to store a portion of the pullwire. The pullwire guide may be configured to break-away from the handle body.

In some embodiments, the pullwire lock includes a lever arm and a button coupled to the lever arm, wherein the button and lever arm are configured to activate and inactivate the lock. The lever arm may include a cam surface configured to removably lock the pullwire handle device onto a pullwire. In some embodiments, the pullwire lock further includes a clamp plate. The cam surface may be configured to apply a force to push the clamp plate to lock the pullwire within the pullwire handle device. In some embodiments, as a portion of a pullwire moves out of the pullwire handle device, the cam surface is configured to apply an increased force to further push the clamp plate and lock the pullwire within the pullwire handle device. In some embodiments, the pullwire lock further includes a second clamp plate. In some embodiments, the second clamp plate may be fixed with respect to the pullwire lock. In some embodiments, the first and second clamp plates are configured to receive a pullwire between them such that an interior portion of the clamp plates couples to a pullwire. The cam surface may be coupled to an exterior portion of a clamp plate.

In some embodiments, the tip containment element includes a storage chamber configured to store a distal portion of the pullwire. The tip containment element may be configured to retain the distal tip of the pullwire within the handle body.

Also described herein are methods for capturing a pullwire using a pullwire handle device configured to secure to the distal end of a pullwire. In some embodiments, the method includes the steps of inserting the distal end of a pullwire into the pullwire handle device, advancing the pullwire further into the pullwire handle device while the distal portion of the pullwire is contained within the pullwire handle device, and locking the distal portion of the pullwire within the pullwire handle device. In some embodiments, the method further includes the step of storing a distal portion of the pullwire within the pullwire handle device. The inserting step may include inserting the distal end of the pullwire into a funnel-shaped proximal end of the pullwire handle device.

In some embodiments, the advancing step includes advancing the pullwire into a storage chamber of the pullwire handle device. The advancing step may further include advancing the pullwire against a surface within the storage chamber such that the pullwire buckles and is stored within the storage chamber.

In some embodiments, the locking step includes pressing a button coupled to a locking mechanism to lock the locking mechanism and lock the distal portion of the pullwire within the pullwire handle device. While in some embodiments, the locking step includes releasing a button coupled to a locking mechanism to lock the locking mechanism and lock the distal portion of the pullwire within the pullwire handle device. In some embodiments, the locking step includes moving the pullwire and pullwire handle device with respect to one another to lock the distal portion of the pullwire within the pullwire handle device. Moving the pullwire and pullwire handle device with respect (e.g., in opposite directions) to one another may include moving the pullwire and pullwire handle device with respect to one another such that a portion of the pullwire moves out of the pullwire handle, for example, pulling the handle distally or holding it still while pulling the pullwire proximally. Proximally and distally may refer to the axial directions of the pullwire.

In some embodiments, the method includes the steps of inserting the distal end of a pullwire into the pullwire handle device, moving a cam surface of a locking mechanism of the pullwire handle device such that the cam surface applies a force to a clamp plate and the clamp plate applies a force to the pullwire, and moving the clamp plate within the pullwire handle device such that the cam surface applies an increased force to the clamp plate and the clamp plate secures the pullwire. In some embodiments, the inserting step includes inserting the distal end of the pullwire into a funnel-shaped proximal end of the pullwire handle device.

In some embodiments, the moving a cam surface step includes rotating the cam surface against a clamp plate and moves the clamp plate toward the pullwire. In some embodiments, the moving the clamp plate step includes moving the clamp plate within the pullwire handle device such that the cam surface further rotates against a clamp plate and further moves the clamp plate toward the pullwire.

In some embodiments, the moving a cam surface step includes pressing a button coupled to a first end of a lever arm, wherein the second end of the lever arm comprises the cam surface. While in some embodiments, the moving a cam surface step includes releasing a pressed button coupled to a first end of a lever arm, wherein the second end of the lever arm comprises the cam surface. For example, as the button is released, the lever arm rotates, thereby rotating the cam surface against the clamp plate.

In some embodiments, the moving the clamp plate step comprises moving the pullwire and pullwire handle device with respect to one another such that the clamp plate moves within the pullwire handle device. Moving the pullwire and pullwire handle device with respect to one another may include moving the pullwire and pullwire handle device with respect to one another such that a portion of the pullwire moves out of the pullwire handle and the clamp plate moves toward the proximal end of the pullwire handle device.

In some embodiments, the method further includes the step of advancing the pullwire further into the pullwire handle device while the distal (tip or end) portion of the pullwire is contained within the pullwire handle device. The advancing step may include advancing the pullwire into a storage chamber of the pullwire handle device. In some embodiments, the advancing step further includes advancing the pullwire against a surface within the storage chamber such that the pullwire buckles and is stored within the storage chamber.

In some embodiments, the methods further include the step of pulling on the pullwire handle device to advance the pullwire in a distal direction. Pulling on the pullwire handle device may advance a proximal portion of the pullwire in a distal direction through a spinal foramen. In some embodiments, the pulling step includes pulling on the pullwire handle device to transmit a force to a proximal portion of the pullwire, wherein the force is greater than 10 pounds. In some embodiments, the pulling step includes pulling on the pullwire handle device to transmit a force to a proximal portion of the pullwire, wherein the force is greater than 35 pounds. In some embodiments, the method further includes the step of coupling a device to a proximal region of the pullwire. Pulling on the pullwire handle device may advance the device in a distal direction through a spinal foramen.

Any of the methods described herein may also include the step of coupling the proximal end region of the pullwire to an elongate device (e.g., a tissue modification device, neural localization device, etc.) either before or after attaching the pullwire handle. The elongate device may be attached end-to-end with the pullwire.

BRIEF DESCRIPTION OF THE DRAWINGS

FIG. 7A shows a partial cross-section through the distal region of one variation of a probe, and FIG. 7B shows a partial cross-section through a more proximal region of the probe.

FIGS. 7C and 7D show another variation of the distal region of a probe including a tip capture mechanism.

FIGS. 15A-15D illustrate different variations of a handle that may be removably attached to a pullwire.

FIGS. 16A and 16B show front and side views, respectively of a handle such as the one shown in FIG. 15D.

FIGS. 17A, 17B and 17C show alternative side views of the proximal end of a handle for use with a pullwire such as the handle shown in FIGS. 16A-16B.

FIGS. 18A and 18B show side and front perspective views, respectively, of this variation, while FIGS. 18C and 18D show partially transparent side and perspective views, respectively. FIG. 18E shows a cross-section through the handle shown in FIGS. 18A and 18B.

FIG. 19A shows an exploded view of this variation. FIG. 19B shows a cross sectional view, and FIG. 19C shows a partially exploded view of this variation. FIG. 19D shows an exploded view of the lock mechanism of the pullwire handle. FIG. 19E shows a partial cross-section through the handle and FIG. 19F shows a detail view of the section of FIG. 19E. FIGS. 19G and 19H show a side and cross sectional view respectively, of a pullwire guide. FIGS. 19I-19K show a storage region of the pullwire handle.

FIG. 29A is another variation of a probe as described herein. FIG. 29B shows a cross-section through the distal end region of the probe of FIG. 29A.

DETAILED DESCRIPTION OF THE INVENTION

Figure 1A:
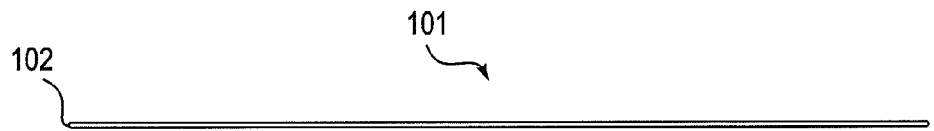
FIGS. 1A-1E illustrates a system including tools for treating spinal stenosis, including a pullwire, a removable pullwire handle, a tissue modification tool, a flexible neural localization tool, and a pullwire positioning probe tool.
Figure 1B:
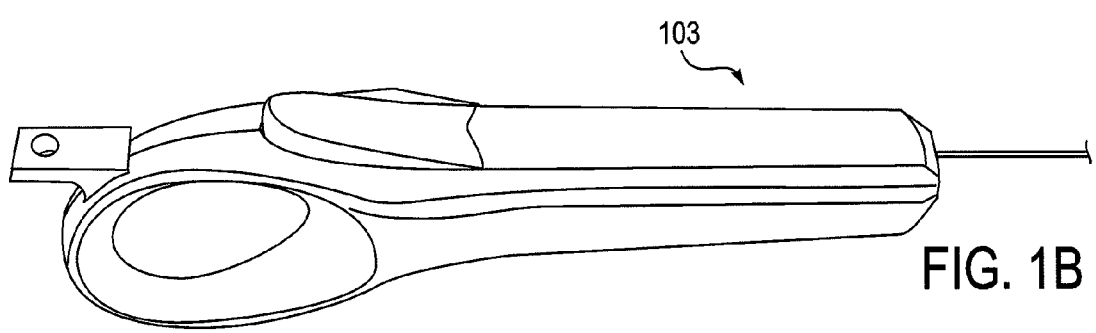
Figure 1C:
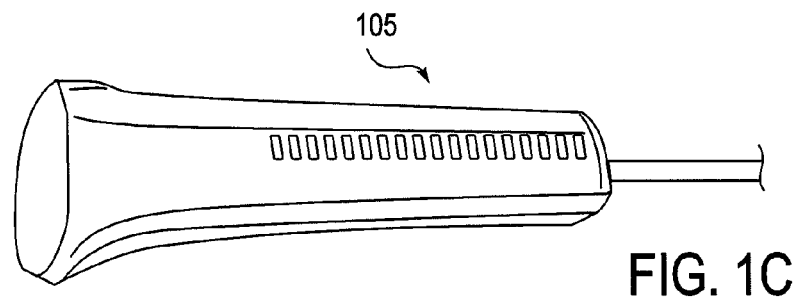
Figure 1D:
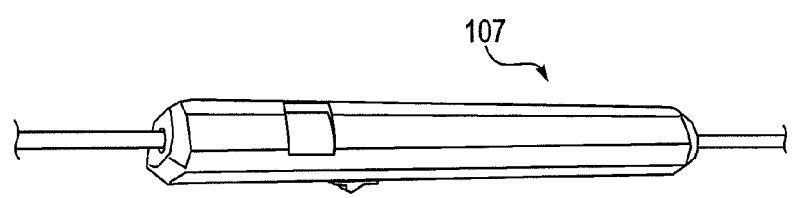
Figure 1E:
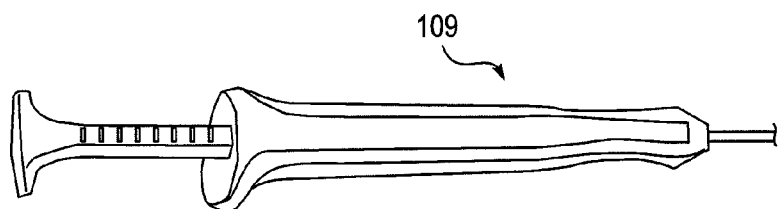

The devices, systems and methods described herein may be use in any appropriate surgical procedure, particularly for the surgical treatment of spinal stenosis. For example, described herein are systems including one or more of the following devices: a pullwire, a handle for the distal end of a pullwire, a probe for positioning a pullwire, a neural localization device for use with a pullwire and a tissue modification device for use with the pullwire.

In particular, described herein are devices and systems including these devices that are configured for use together as a system. For example, the devices described herein may all be coordinated so that they may function together, and may include markings, orienting structures and other features that are common between the different devices within the system. In some variations the devices all include front/back, top/bottom, or other orientation structures on the handles of the devices. The handles may be structured in common.

The devices described herein may include handles that allow the devices to be hand operated using one hand or two hands (or both). In some variations, the devices include handles that guide or regulate the hand position when the device is in use. For example, the devices may regulate hand position. Coordinating or regulating hand position may be particularly important during surgical procedures using these devices to access difficult to reach and/or otherwise sensitive regions of a patient's body.

Many of the devices described herein may be used with a pullwire for either or both positioning of the device and operation of the device. Thus, many of the devices include pullwire management features to help position, orient, grasp, and regulate the pullwire. If the pullwire is not properly managed, it may prevent correct operation of the device, may increase risk of misuse of the device (potentially harming the patient), and may risk harming the operator (e.g., surgeon or other medical professional).

FIG. 1 shows one variation of a system for treating spinal stenosis. In FIG. 1, the proximal ends of a pullwire 101, a pullwire handle 103, a tissue modification device 105 (that may be used with a pullwire), a neural localization device 107 (that may be used with a pullwire) and a probe 109 that may be used to place a pullwire are all shown. In this example, as shown, the proximal regions of these devices are coordinated so that they share common features which facilitate their operation as a system. For example, the handles of these devices are all oriented with a flat 'front' region and a curved or projecting 'back' region. The flat front region is indicated by a different color, and may be textured so that it is apparent by the feel of the device that it is the front region. The flat front region may allow the devices to be used more effectively in an open, partially open, or minimally invasive procedure. As described below, when the devices are used to operate on spinal tissue, or other tissue that is otherwise difficult to access, the flat front may allow the visualization of the region of the target tissue even when the device is being held or manipulated.

The pullwire shown in FIG. 1 is typically long (e.g., elongated) and flexible, and may have a sharp (tissue penetrating) distal end, not shown, and a proximal end 102 that allows it to be coupled to a pullwire coupling member securely. For example, the pullwire may include a ball or other shaped end (which may be conical, tubular, ring, etc.) for coupling to a pullwire coupling member of a device (such as a tissue modification device or a neural localization probe). The proximal end 102 may be configured to lock into a pullwire coupling member at the distal end of a tissue modification device (such as the one 105 indicated in FIG. 1), and/or a neural localization device 107. Similarly, the proximal end of the pullwire may be configured to pass through the probe 109 so that the probe may be removed from over the proximal end of the pullwire during operation.

Each of these devices (the probe 109, the neural localization device 107, the tissue modification device 105 and the pullwire handle 103) are described in greater detail below.

Figure 2A:
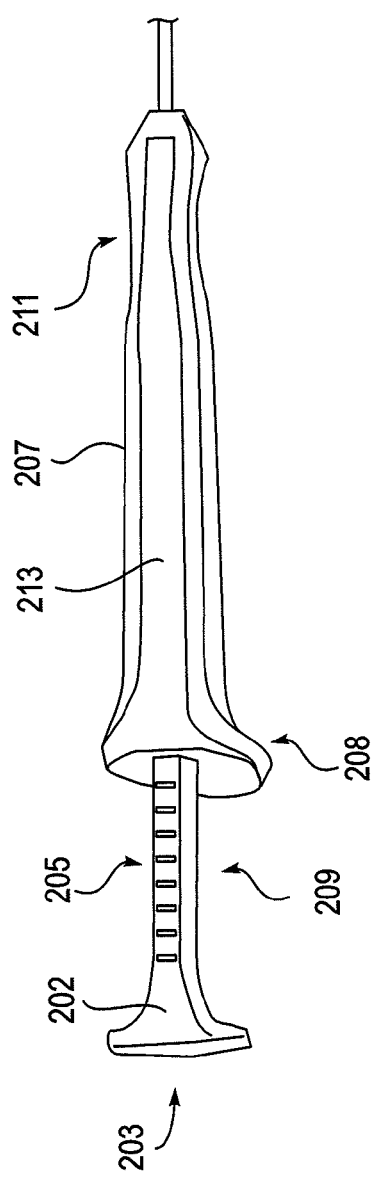
FIG. 2A shows a side perspective view of an alternative view of the proximal end of another variation of a probe.

FIGS. 2A-7L describe and illustrate different variations of probes that may be used to position a pullwire. For example, FIG. 2A illustrates one variation of an improved probe having additional features including a calibrated, keyed, and flanged pusher 202.

Figure 2B:
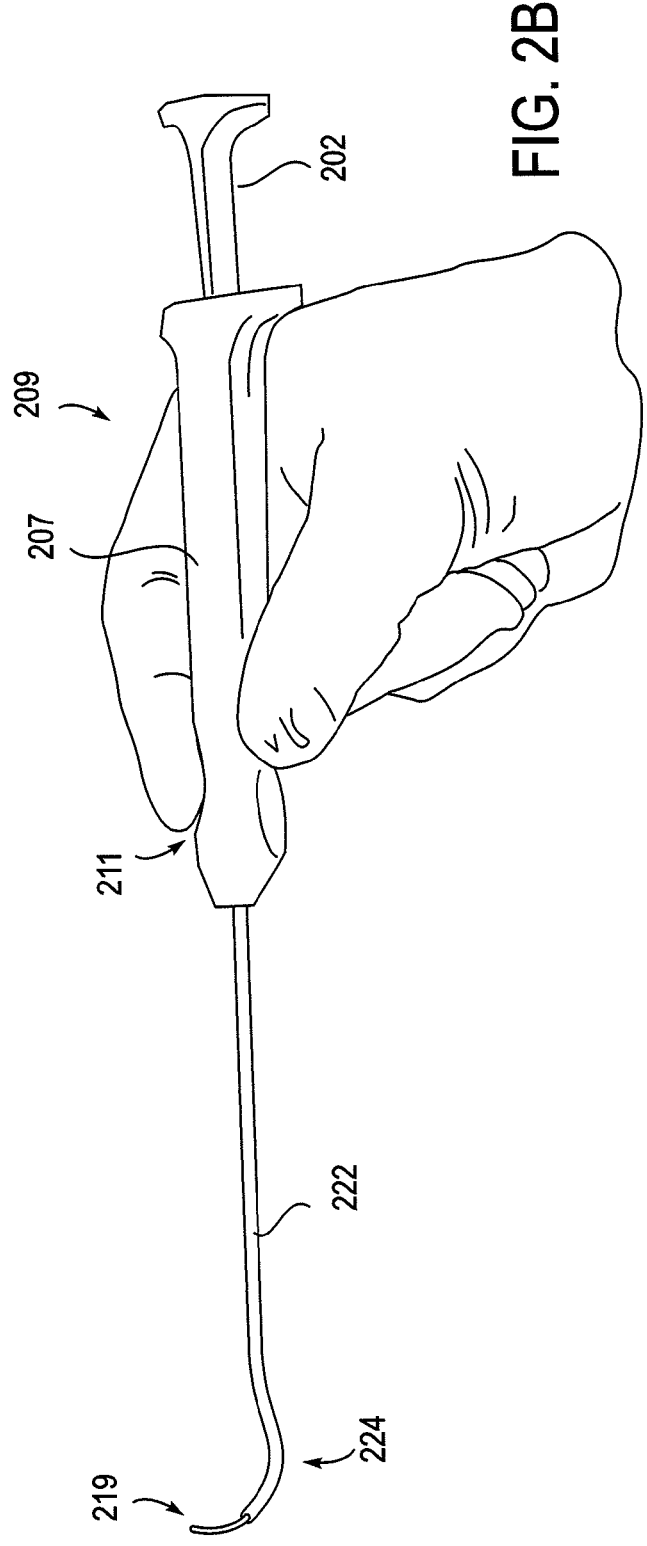
FIG. 2B illustrates a perspective view of a probe as in FIG. 2A when handheld.

For example, in the variation illustrated in FIGS. 2A-2B, the probe 209 includes a handle portion having a pusher 202 that communicates with an internal cannula slideably disposed within the external cannula so that the internal cannula may be extended from the distal end of the probe for placement around a target tissue, as illustrated in FIG. 2B. The pusher includes a flanged 203 proximal end having a finger (e.g., thumb) pushing surface that is perpendicular to the long axis of the device (including the long axis of the handle). As described in greater detail, this proximal end may be formed to more readily allow insertion of a pullwire by guiding the pullwire into the lumen of the inner cannula. The pusher is calibrated 205 along the side in a top-facing surface. The calibration shown in this example includes markings to indicate depth (e.g., how far down the pusher has been extended), which corresponds to how far out of the distal end the inner cannula is extended. The calibrations may include alphanumeric symbols, colors, textures, or any combination of the like. The calibrations may be referenced to distance (e.g., depth, length, etc.), or they may be un-referenced (as shown in FIG. 2A).

The handle portion of the probe 207 is configured to be readily gripped by a person's hand. The handle portion includes a front surface 213 that is substantially flat, and has a different feel (by the flat cross-section or texture, for example) than the other circumferential regions of the handle, which may be curved or rounded. In this variation, the flat surface not only provides tactile feedback to the user that this is the front of the probe (for orientation), but may also allow the user to visualize down the front length of the device for ease in viewing during operation. Thus, a user may be able to look down the front of the device, which typically corresponds to the direction of extension of the distal end of the inner cannula of the probe, as the probe is inserted into the tissue. This feature may be specifically useful when the probe is inserted into tissue via a minimally invasive and/or "mini-open" technique, such as through a tube. In this instance, the flat surface of the handle and the inner diameter of the tube may not contact one another, and may define a space through which a user may visualize into and/or through the tube and/or visualize tissue.

The handle portion 207 of the probe 209 may also include functional shapes for aiding in operation of the probe. For example, the proximal end of the handle region 207 may include a flange, lip, or rim 208 extending away from the front of the device, which does not extend towards the front (and otherwise block the view down the long front of the probe). This proximal rim may help provide leverage for operation of the probe, particularly when the pusher 202 is being driven to extend the inner cannula out of the distal end of the probe. In addition, the probe handle 207 may also include a waist region 211, that may also be referred to as a penciled region. This waist region 211 may be located distally along the handle, and may allow the device to be held pencil-like at the more distal end of the handle. For example, this region may be used to hold the probe using just the finger tips of the hand, improving the control and precision of operation, particularly during placement. This is illustrated in FIG. 2B.

In FIG. 2B, the probe 209 is held, pencil-like, with the fingertips grasping the waist region. The pusher 202 is shown partially pushed in, showing the distal end of the probe 219 extending partially from the distal end of the outer cannula 222. The outer cannula of the probe is fixed relative to the handle region 207, and had a curved distal end 224. In this example, the curve is crescent-shaped, so that it initially curves away from the centerline of the probe (e.g., towards the 'back' of the probe), and then curves back towards the front of probe, as shown. The inner cannula 219 of the probe is pre-biased so that it assumes a curved shape upon leaving the outer cannula 222. For example, the inner cannula may be a Nitinol cannula having a pre-set curved shape. The cannula may be solid, woven, mesh, etc., but includes a passageway for the pullwire. The distal tip of the inner cannula may be configured so that is substantially atraumatic. It may also be configured so that it cannot be withdrawn into the cannula (e.g., it may have a slightly larger OD than the ID of the outer cannula, etc.). In some variations, the distal tip may be blunted or rounded. Alternatively, the distal tip may be configured to cut tissue.

Figure 3A:
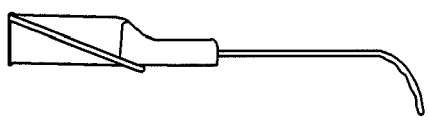
FIGS. 3A-3N illustrate alternative variations of probes that may be used to position a pullwire, as described herein.
Figure 3H:
Figure 3B:
Figure 3I:
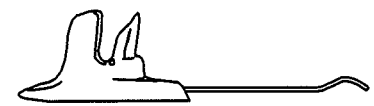
Figure 3C:
Figure 3J:
Figure 3D:
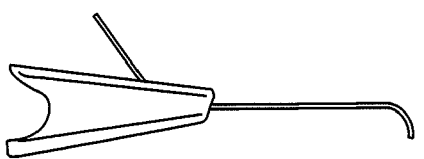
Figure 3K:
Figure 3E:
Figure 3L:
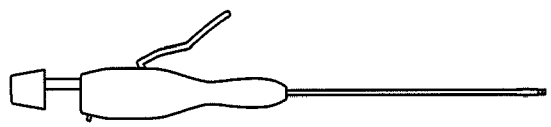
Figure 3F:
Figure 3M:
Figure 3G:
Figure 3N:
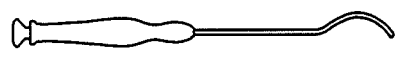
Figure 6A:
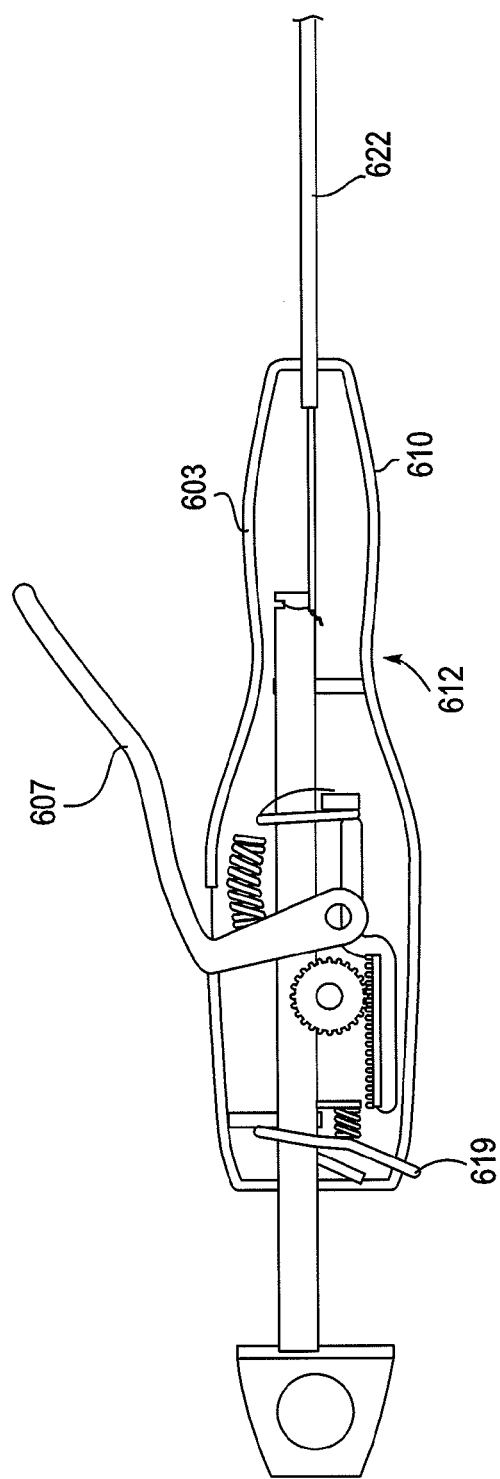
FIGS. 6A and 6B show an exposed view of the internal workings of another variation of a probe device.
Figure 6B:
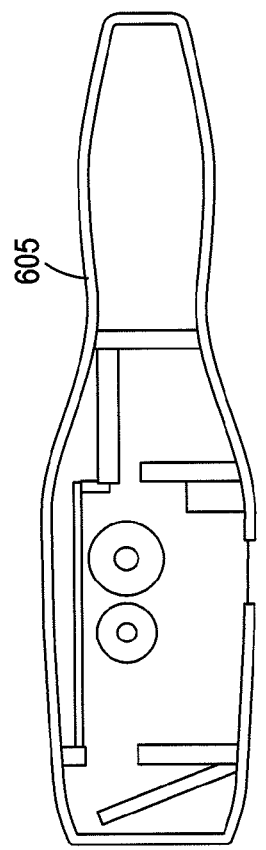

FIGS. 3A-3N illustrate alternative variations of the probe, including alternative variations of the handle. In some of these variations, for example, 3D, 3E, and 3G-3K, the handle portion of the probe includes a lever or switch portion that may be used to extend, lock, unlock, and/or retract the inner cannula of the probe. For example, the probe may include a switch or control for releasing the inner cannula so that it can be moved to extend or retract from the distal end. Thus, the probe may be locked, preventing motion of the inter cannula. FIGS. 6A and 6B illustrate another variation of a probe having a handle or control for regulating the motion of the inner cannula.

Figure 4A:
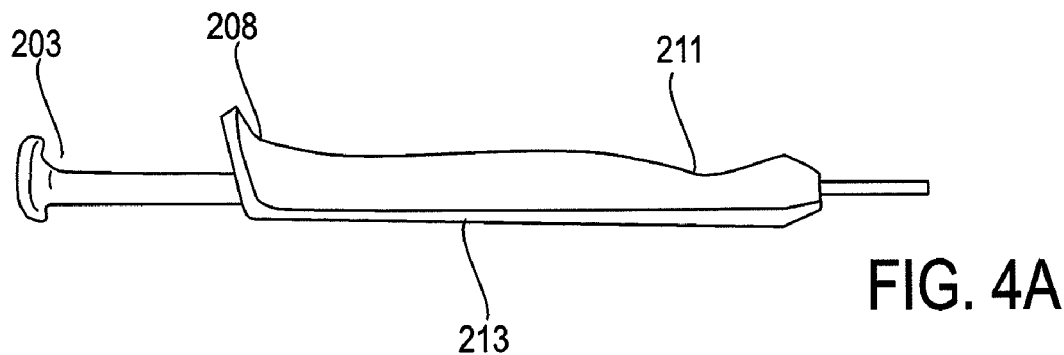
FIGS. 4A and 4B show a front and two side perspective views, respectively, of a handle of a probe such as the one shown in FIGS. 2A and 2B.
Figure 4B:
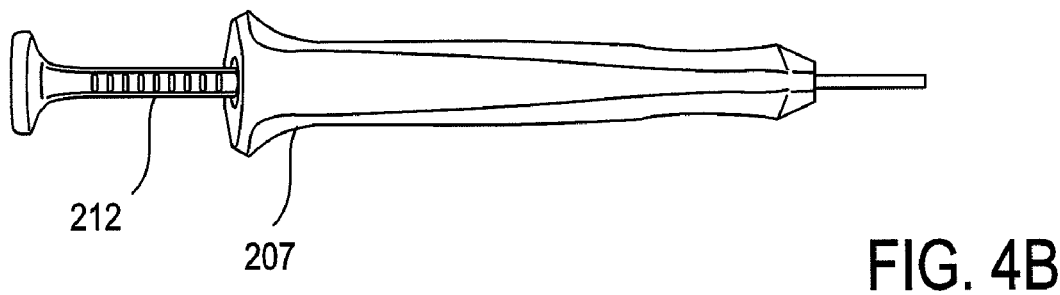
Figure 4C:
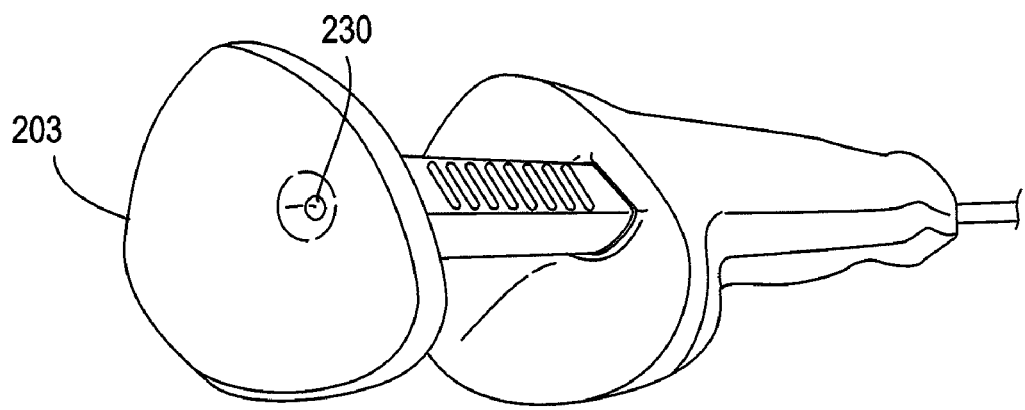
FIG. 4C shows a top perspective view of the proximal end of the same guide.

FIGS. 4A and 4B show front and side views, respectively, of the variation shown in FIG. 2A. FIG. 4C shows a top perspective view of the same variation. As mentioned above, the proximal end of the pusher 202 may be flanged. In some variations, as shown in FIG. 4C, the proximal end of the pusher (and thus the proximal end of the probe) may include a funnel-like structure 230 that is continuous with the inner channel through the cannula of the probe, to make insertion of the distal end of the (often sharp) pullwire into the probe both safer and simpler. Thus, the top end may for a convex or conical (e.g., funnel) shape for guiding the distal end of the pullwire through the inner cannula of the probe.

Figure 5A:
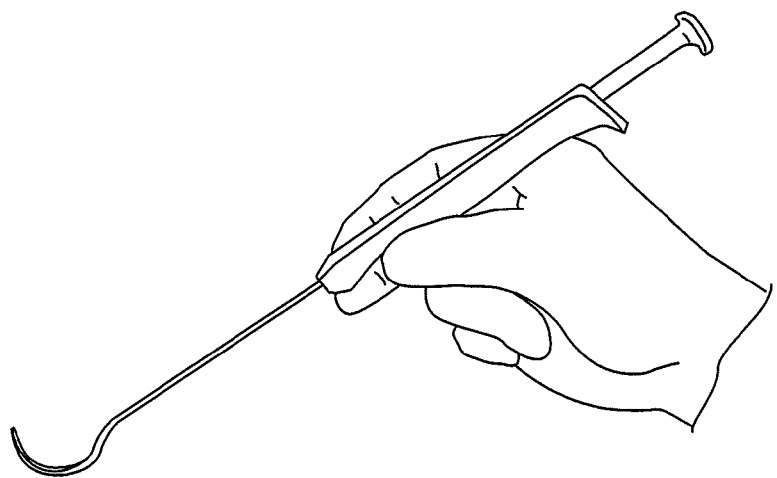
FIGS. 5A-5C illustrate methods of manipulating the probe shown in FIGS. 4A-4C.
Figure 5B:
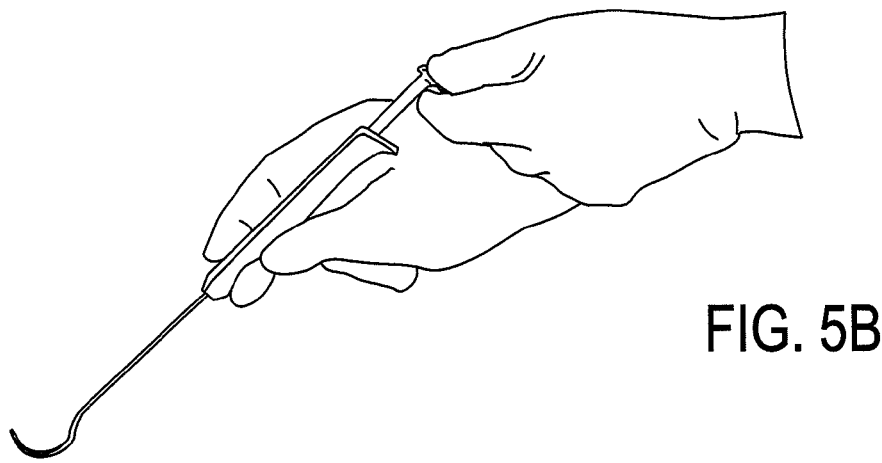
Figure 5C:
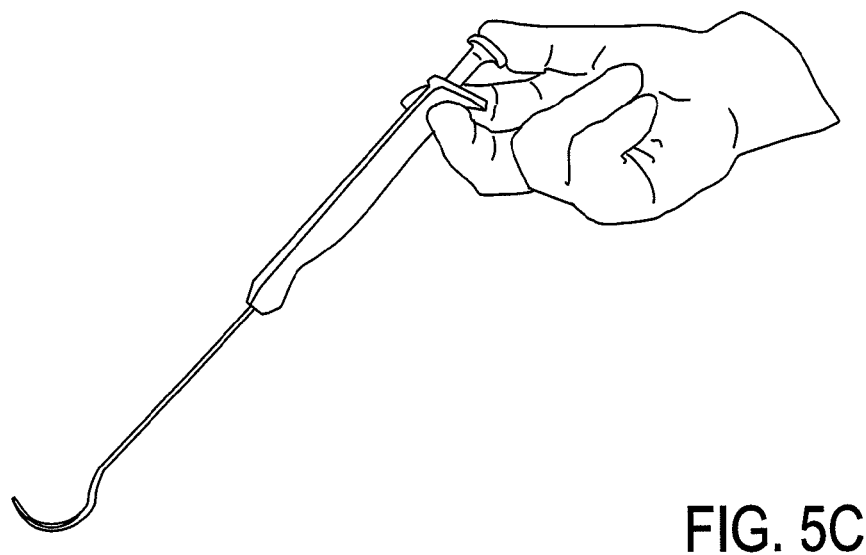

The variations of the probe shown above may be configured to operate in a two-handed or one-handed manner. FIGS. 5A-5C illustrate different methods of operating the probes described above, similar to FIG. 2B. FIG. 5A shows another example of holding the probe by the waist region near the distal end of the handle in a pencil-like grip. This may be referred to as penciling the probe. Thus, the waist region may be relatively narrow, and may include a concavity around the perimeter of the handle region into which the fingertips may fit. This narrowed region may allow the distal end of the probe to be manipulated with precision, allowing tilting, rotation and angling of the distal end. In this variation, the inner cannula may be operated by moving the pusher with the thumb, while penciling the probe with the fingers (for example, with the index and middle fingers). In FIG. 5B, the probe may be used in a two-handed arrangement. In this example, the probe is gripped in the right hand in a penciling grip, while the left hand is used to operate the inner cannula by moving the pusher. The flanged regions at the proximal end of the handle 208 and the pusher 203 provide leverage for both pushing and pulling. FIG. 5C illustrates one-handed deployment of the distal end of the probe (the inner cannula) using only one hand. In this operation, the proximal flange regions may be used as grips for the fingers, as shown.

FIGS. 6A and 6B illustrate another variation of a probe in which the handle portion is opened showing two housing portions 603, 605, and exposing the operation of the control (lever 607). In this variation, the control 607 may be any handle, lever, button, or the like. The control is geared to advance the inner cannula 610, as shown. As illustrated here, in some variations the pullwire may be fed through a side of the probe 612, rather than the proximal end of the probe, as shown in FIGS. 5A-5C. The variation shown in FIGS. 6A and 6B may also include a lock 619, which to prevent advancing and/or withdrawal of the inner cannula relative to the fixed outer cannula 622.

As mentioned, the probe inner cannula may be a shape-memory material or other material that assumes a straight or curved shape upon exiting the distal end of the fixed outer cannula. In some variations, the probe may include a safety retainer to retain the distal end of the inner cannula in the event of failure of the inner cannula during operation. In some variations, the safety retainer may prevent failure of the inner cannula. In this context, failure refers to the breaking off or bending of the inner cannula. For example, an inner cannula may break off during operation of a probe. This breakage may occur because of material fatigue, or because the probe must operate within bony or ligamentous regions that place stresses upon the distal tip regions of the probe, and particularly the inner cannula.

A safety retainer may include a tether, leash or the like that operates when the inner or outer cannula fail. For example, FIGS. 7A and 7B illustrates one variation of a safety retainer comprising a tether 705 that is secured 709 to the distal end of the inner cannula 703. In this variation, the tether is freely movable within an inner lumen or passage 711 within the inner cannula 703. Thus, as the inner cannula extends and bends, the tether (safety retainer 705) does not constrict the movement. FIG. 7A shows the distal end of one variation of a probe in cross-section. The inner cannula 703 is slideably movable within the outer (fixed) cannula 701, shown as transparent in this example. The inner cannula has a thickness that includes an inner, central, lumen that is configured for passage of a pullwire, and a peripheral side lumen 711 in which the safety retainer (tether 705) is located. As illustrated in FIG. 7B, the tether 705 is slack within the tether passage 711; in FIG. 7B, the proximal end of the tether includes additional material present in slightly expanded proximal end of the passage 711. In some variations the tether may be an elastomeric or other extendable material. In general the tether may be made of any appropriate material, and may be solid, woven, or the like.

In use, the safety retainer may act to prevent the distal end of the probe (and particularly the distal end of the inner cannula) from being left behind within the patient if it should break. The safety retainers described herein may also help retain the outer cannula in the event that it fails.

FIGS. 7C and 7D illustrate another variation of the distal end of a probe including a safety retainer, similar to the variation shown in FIGS. 7A and 7B. In this variation, the safety retainer is a loop of material that passes down the length of the inner cannula (within two lumen formed in the wall of the inner cannula. The material (e.g., a cable or wire of Nitinol, stainless steel, etc.) extends distally within a first lumen, then curves around at the distal end then extends proximally within a second lumen. The distal end (the loop) may be secured to the tip. For example, in FIG. 7C, the outer cannula is a shaped stainless steel cannula, and the inner cannula ("catheter") is formed from multi-lumen PEBAX that is extruded over a shaped Nitinol hypotube. The safety retainer includes a Nitinol wire or cable that extends within the lumen formed in the wall of the PEBAX extrusion (the "multi-lumen" extrusion). For example, a 0.006" Nitinol wire with an outer polyimide cover (e.g., extruded on it) may run through the lumen in the PEBAX sheath. The distal tip region of this example is shown in greater detail in FIG. 7D.

In FIG. 7D, the loop formed by the cable of the safety retainer passes through side flanges at the tip. The (atraumatic) tip is staked to the Nitinol hypotube. The cable can be secured to the tip by extruding material (e.g. PEBAX) over it, or by crimping, welding, or the like. For example, FIGS. 7F and 7G illustrate capture of the distal end of the safety retainer (e.g., cable) at the tip. In FIG. 7F (cross-sectional view), the cable 713 is captured by welding 712 the cable to the tip 714. In this illustration, the cable of the safety retainer is stainless steel. In FIG. 7G the safety retainer is welded to the tip which includes a skirt region 715. In some variations, this skirt may protect the tip and support the safety retainer. In some variations, the skirt may be crimped.

Figure 7E:
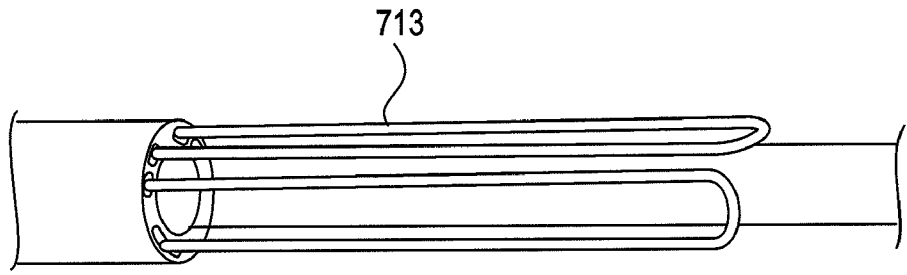
FIG. 7E shows a more proximal region of the probe shown in FIGS. 7C and 7D.
Figure 7F:
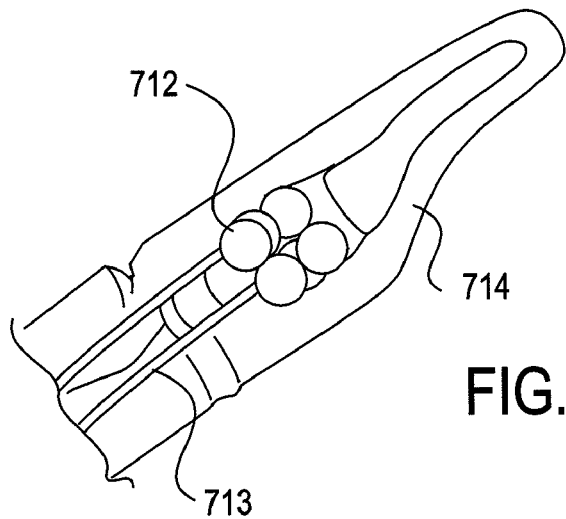
FIGS. 7F and 7G show alternative configurations for probes including tip capture mechanisms such as those of FIGS. 7A-7C.
Figure 7G:
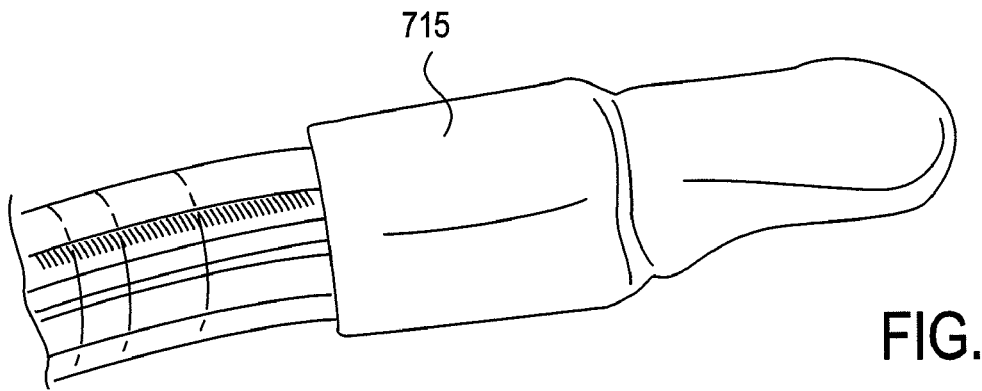

FIG. 7E illustrates the proximal end of the safety retainer within the inner cannula (shown in partial cut-away). In this example, the cables or wires 713 of the safety retainer are secured at the distal end. For example, the safety retainer material (e.g., wire or cable) may be fused to the inner cannula or catheter by fusing PEBAX over them after they exit the lumen in the wall of the inner cannula, and after removing any cover on the wire or cable (e.g., a polyimide extrusion). In other variations the proximal end may be free and/or may exit the probe, as illustrated in FIG. 7H.

Figure 7H:
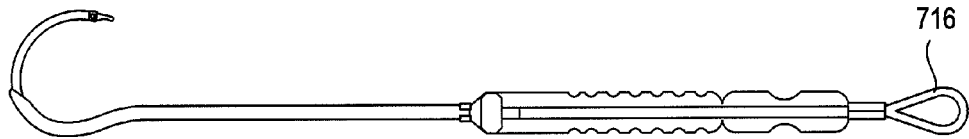
FIG. 7H illustrates one variation of a probe including a stylet such as those shown in FIGS. 7A-7C.
Figure 7I:
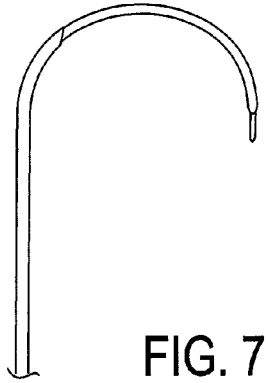
FIGS. 7I and 7J illustrate another two variations of the distal end regions of probes that may be used to position a pullwire around a target tissue.
Figure 7J:
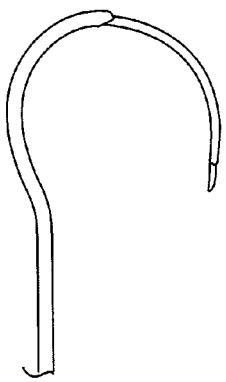

In FIG. 7H, the safety retainer comprises a cable running the length of inner cannula within one or more (in the case of looped or multiple strands of safety retainers) lumen in the wall of the inner cannula. The safety retainer may be secured to the proximal end, or it may exit (e.g., as a loop 716) the proximal end of the probe, as shown. As mentioned, in the event of a fracture of the inner cannula of the probe, the safety retainer keeps it connected. In some variations, the safety retainer may prevent the cannula from folding and/or flattening which may precede a complete detachment or fracture of the hypotube forming the cannula.

In general, the distal end of the probes described herein may be curved or bent, and/or may be curveable or bendable. As illustrated in the two variations shown in FIGS. 7I and 7J, the outer distal end may be more or less curved. The inner cannula may be configured to bend as it exits the distal end of the outer cannula, as shown, thereby increasing the ability of the probe to guide a pullwire around a target tissue.

Figure 7K:
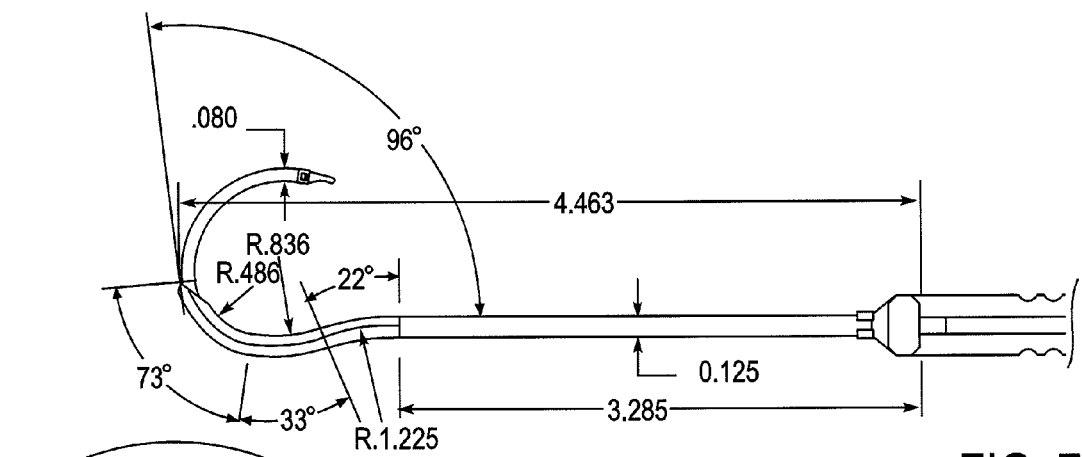
FIGS. 7K and 7L illustrate two variations of the distal end regions of probes similar to those shown in FIGS. 7C and 7D, indicating exemplary dimensions.
Figure 7L:
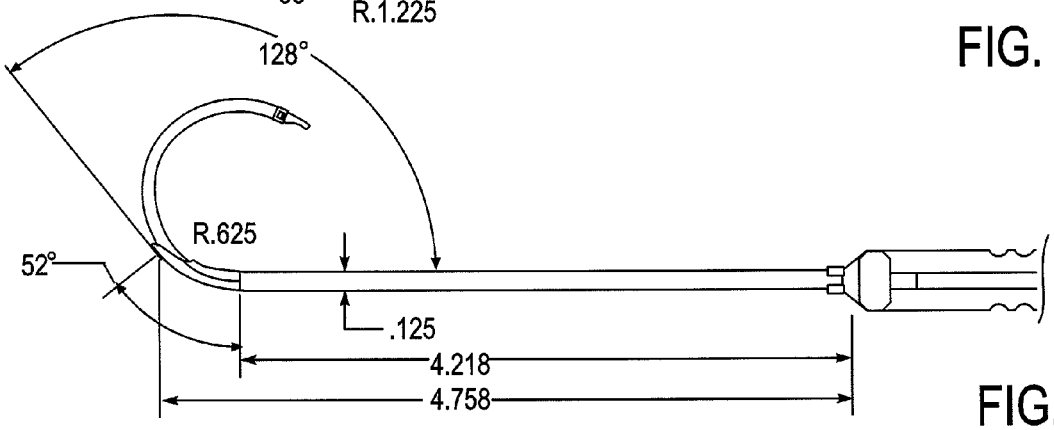

FIGS. 7K and 7L illustrate two particularly useful variations of the probe ends that may be used. For example, FIG. 7K indicates angles and dimensions for one variation of an ipsilateral probe, and FIG. 7L indicates angles and dimensions for one variation of a contralateral probe. An ipsilateral probe may be used to treat spinal decompressions using an ipsilateral approach, as described in more detail in co-pending U.S. patent application Ser. No. 12/352,978, titled "MULTIPLE PATHWAYS FOR SPINAL NERVE ROOT DECOMPRESSION FROM A SINGLE ACCESS POINT" (filed Jan. 13, 2009), and fully incorporated by reference herein. Similarly, a contralateral probe may be used to treat spinal decompression using a contralateral approach. The dimensions and measurements provide have been shown to be beneficial. The dimensions (length, width, height, thickness, diameters, etc.) and angles (arc, arc length, curvature, etc.) maybe varied in individual cases +/−1%, +/−2%, or +/−about 5%). Other dimensions have not proven effective in treating spinal stenosis, particularly when operating through a stenotic opening in the spinal nerve channel.

Two of the bends in the ipsilateral probe shown in FIG. 7K are of particular interest: the Sheppard's hook angle (labeled 22°) and the final distal curve of the outer cannula (indicated as 96° off of the long axis of the device). The Sheppard's hook angle allows the probe to move and be positioned while avoiding the spinous process. If this curve is not sufficiently large, the hooked end will be unable to orient the opening in the outer cannula so that the inner cannula can be positioned dorsally. Similarly, the distal curve of the outer cannula should position the outer cannula opening so that the inner cannula exits at approximately 90° (e.g., between about 80° and about 100°) relative to the long axis of the device, as shown in FIG. 7K.

The distal bend in the contralateral probe is typically shallow (having an angle with the long axis of the device of about 128°, as shown. This orientation allows the probe, when inserted contralaterally, to avoid interference by the cauda equina, and other structures, while allowing the probe to be inserted as necessary.

Other probe variations are illustrated and described in greater detail below, for example, in FIGS. 29A-32I. Any of the features described above may be incorporated in these probe configurations, including (but not limited to) the handle features.

Figure 8A:
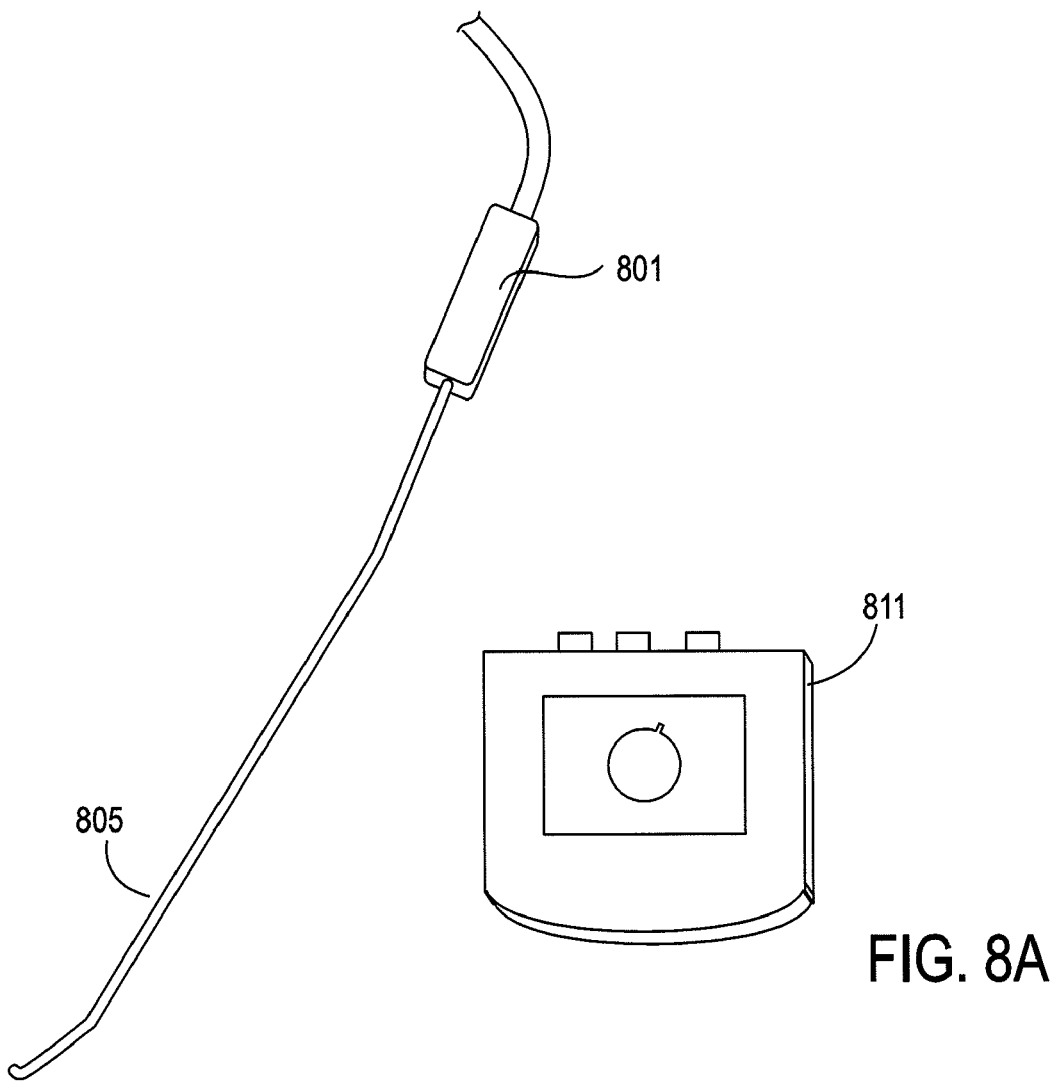
FIGS. 8A and 8B shows side perspective views of two variation of neural localization devices ("NLR devices") as described herein.
Figure 8B:
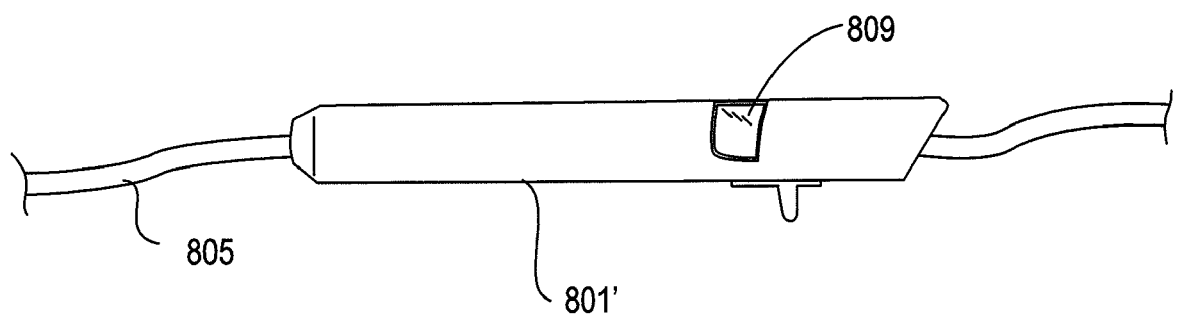

The systems described herein may also include one or more neural localization devices configured to determine the proximity and relative location of a pullwire pathway to a nerve or nerves. For example, FIGS. 8A and 8B illustrate one variation of a neural localization device. In FIG. 8A, the neural localization device includes a proximal handle 801 that is connected to a flexible distal region 805. The device may also include a controller 811 that may be integrated with or separate from the handle 801. The flexible distal end may be configured to couple with a pullwire so that it can be pulled into position. The flexible distal end may include one or more electrodes or arrays of electrodes that may be used to create a limited stimulation field. Stimulation from the distal end of the neural localization device may indicate the presence of a nerve relative to one side or portion of the neural localization device.

In some variations the handle portion 801 of the device may be configured for improved operation, including an indication of what portion (e.g., what side) of the neural localization device is being activated, the orientation of the distal end of the neural localization device, and/or a control for controlling stimulation provided by the neural localization device.

For example, FIG. 8B illustrates one variation of a handle 801' of a neural localization device. In this example, the handle includes a window 809 on one or more sides of the device that indicates visually where and when stimulation is being applied.

Figure 9A:
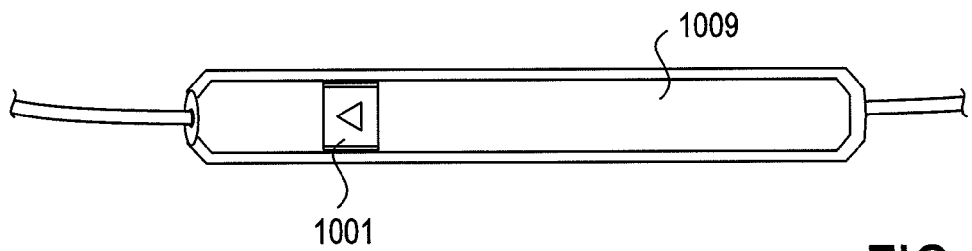
FIGS. 9A and 9B show front and side views, respectively, of the proximal (handle) portion of a neural localization device.
Figure 9B:
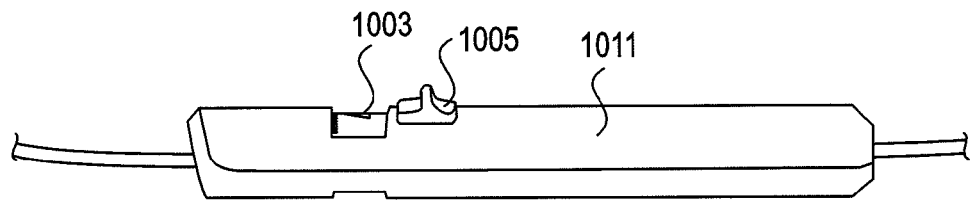

FIGS. 9A and 9B show front and side perspective views of a variation of a neural localization device similar to the device shown in FIG. 8C. For example, the front 1009 of the neural localization device is shown in FIG. 9A. This embodiment includes a window 1001 that indicates when the front or top of the neural localization device is being stimulated. The back 1011 of the handle also includes a window 1003 that indicates when the back or bottom of the neural localization device is being stimulated. The front window 1001 may also indicate when the back of the neural localization device is being stimulated and the back window 1003 may also indicate when the front of the neural localization device is being stimulated. For example, a window may indicate "top", "bottom", and/or "off". The handle also includes a control 1005 (shown here as a slider) for toggling stimulation between the back and front; the control may also be used to turn the stimulation "on" or "off" and in some variations can also be used to determine the level of stimulation.

Figure 10A:
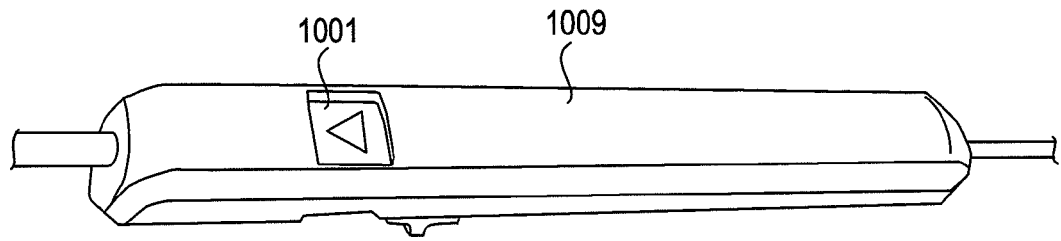
FIGS. 10A, 10B and 10C show alternative views of the proximal (e.g., handle) portion of the neural localization device shown in FIGS. 9A and 9B.
Figure 10B:
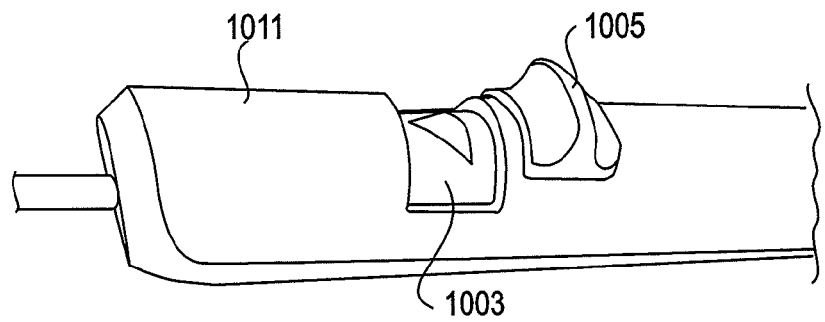
Figure 10C:
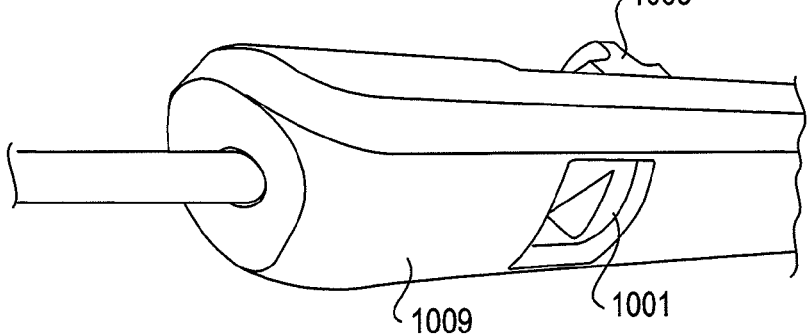

FIG. 10A shows a side perspective view of the neural localization handle shown in FIGS. 9A and 9B, and FIG. 10B shows an enlarged view of the window on the back side of the handle. FIG. 10C shows an enlarged view of the front window. The window may show an indicator such as a graphic, including a color, an alphanumeric message, a symbol, or the like.

As mentioned above, some variations of the systems described herein also include a tissue modification device such as those mentioned and incorporated by reference above. FIGS. 11A-13D illustrate variations of tissue modification devices, and particularly handles for tissue modification devices. Any of these tissue modification devices may be configured to couple at their distal ends with the proximal end of a pullwire. The handle may include a grip region, and may also include a distinct and flat front face, as mentioned above. The front face may be marked to indicate the orientation of the tissue modification device. Any of the devices described herein, including the tissue modification devices (and neural localization devices, etc.) may be configured so that the orientation of the distal ends of the device are relatively fixed with respect to the handle, and therefore the front face of the handle.

Figure 11A:
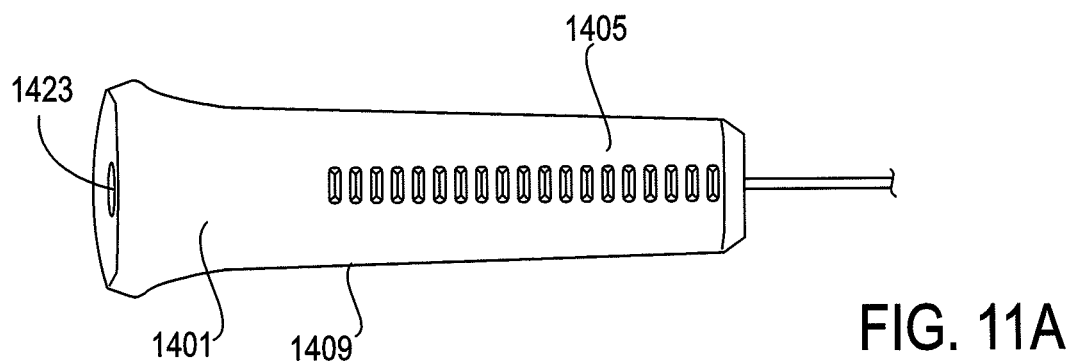
FIGS. 11A and 11B show front and side perspective views, respectively, of the proximal end region (e.g., the handle) of a tissue modification device.
Figure 11B:
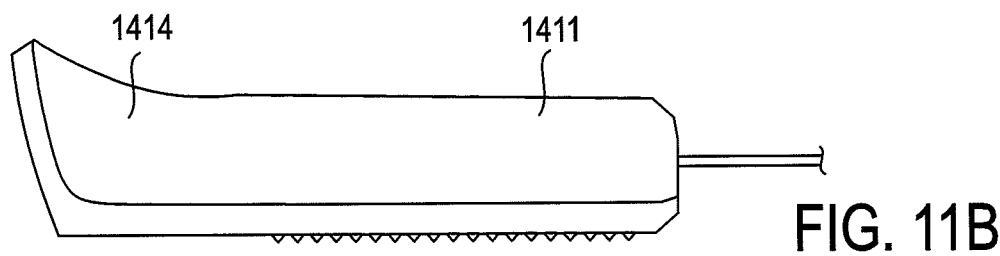
Figure 12A:
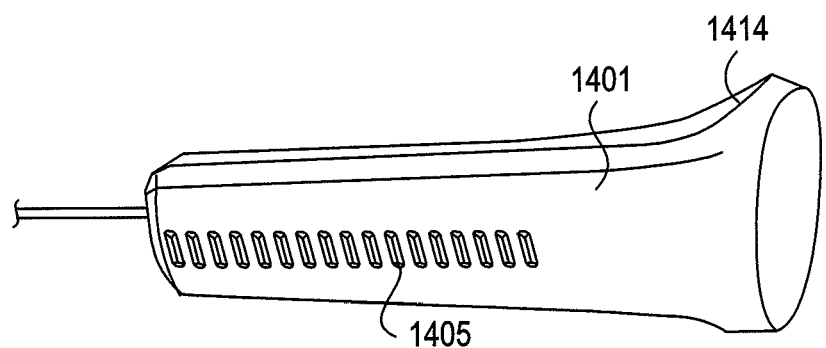
FIGS. 12A, 12B and 12C show alternative side and end views of the proximal end of the tissue modification device shown in FIGS. 11A and 11B.
Figure 12B:
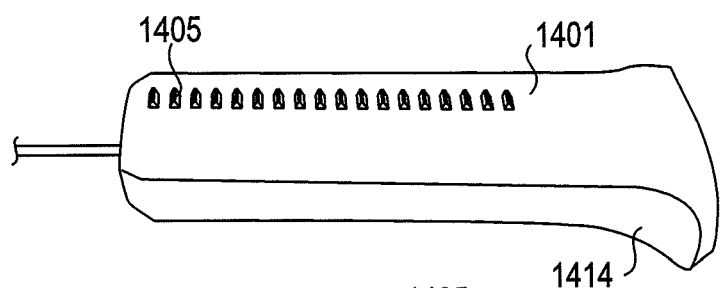
Figure 12C:
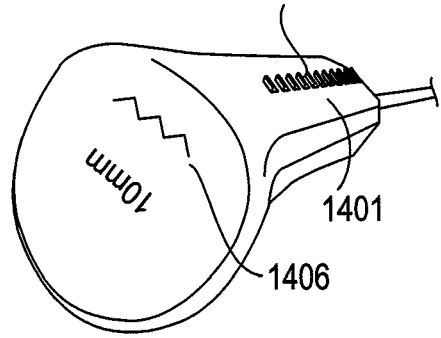

FIG. 11A shows one variation of a handle for a tissue modification device. The handle include the flat front face 1401 that is textured 1405 or otherwise marked to indicate that it corresponds to the front of the device. In this variation, the front of the device predicts the orientation of the distal end of the device including the flexible cutting surface(s), as illustrated in FIGS. 13A-13D. The handle includes a gripping region 1409, and may have smooth or rounded sides 1411. The proximal end of the handle may be shaped to prevent the handle from slipping, including a lip, flange or rim 1414 against which the hand or fingers may rest. The proximal flange 1414 may also be configured so that it does not extend around the front portion of the device, as mentioned above. FIGS. 12A to 12C illustrate alternative views of the handle shown in FIGS. 11A-11B. In some variations the handle may be marked to indicate the size or variation of the tissue modification device, as illustrated in FIG. 12C, in which the proximal end of the handle includes an alphanumeric graphic marking the size (10 mm for an example) of the tissue modification device. Furthermore, as shown in FIG. 12C, the handle may be marked to indicate on which side of the device the tissue modification elements are located (e.g. the abrasive or sharp side of the device). As shown, marking 1406 may indicate that the blades or other tissue modification elements are location on the front side 1401 of the device.

Figure 13A:
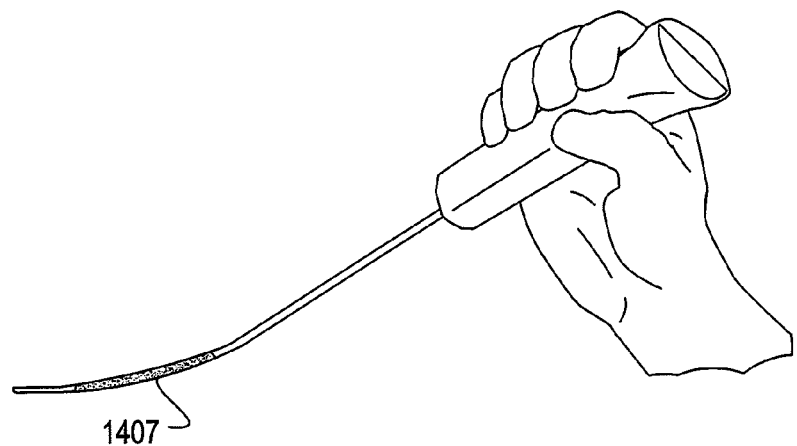
FIGS. 13A and 13B illustrate method of holding or manipulating the tissue modification devices similar to those shown in FIGS. 11A-12C.
Figure 13B:
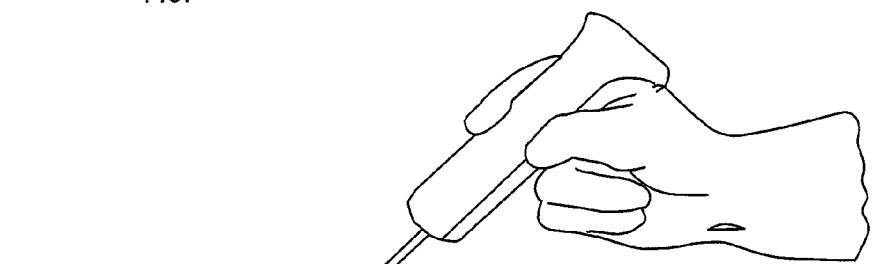

FIGS. 13A and 13B illustrate different methods of holding and operating a variation of the handle of the tissue modification device similar to that shown above. For example, in FIG. 13A, the device is configured to be gripped so that the tissue modification device may be driven against the tissue to remove or otherwise modify tissue. In FIG. 13B the device may be held in a penciling configuration. For example, in some variations the handle includes a narrowed or tapered waist configuration. The distal end of the device 1407 is typically flexible, and includes one or more blades or cutters for modifying tissue. For example, FIGS. 13C and 13D illustrate two variations of tissue modification devices that may be used.

Figure 13C:
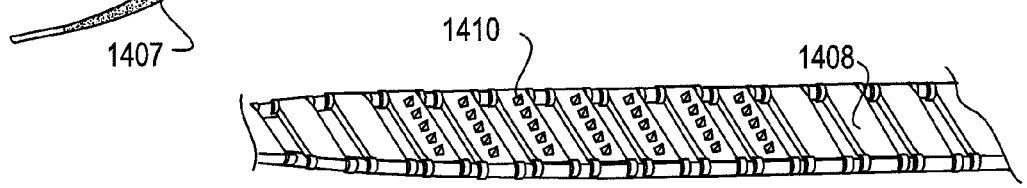
FIGS. 13C and 13D illustrate alternative views of a portion of a tissue modification device that may be used with the handles shown in FIGS. 11A-13B.
Figure 13D:
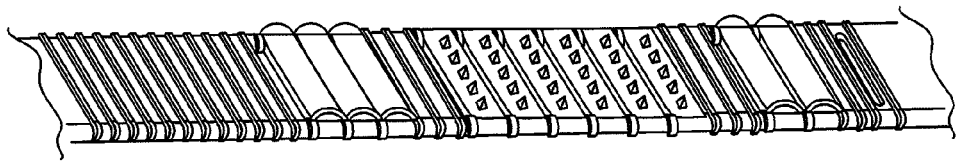

FIG. 13C shows a portion of the distal end of a flexible tissue modification device comprising a plurality of flexibly connected rungs 1408 (having a top and a bottom side), that include a plurality of tissue-cutting blades 1410 on some of the rungs. There are gaps between the rungs shown in FIG. 13C, however these gaps are not necessary, as illustrated in the variation shown in FIG. 13D. In FIG. 13D, the device includes a plurality of rungs that are flexible connected without substantial gaps. In this variation some of the rungs include side-cutting blades, configured as side-cutters along the side (widths) of some of the flexibly connected rungs.

FIGS. 14A to 17C illustrate a distal handle that may be attached to the distal end of a pullwire, and may be included as part of the systems described herein. In general, the handle is configured to removably lock onto a pullwire and allow a substantial amount of pulling (and/or pushing) force to be transmitted from the user through the handle to the pullwire. The handles described herein may be configured so that they may "choke up" on a pullwire, so that the handle can be allowed to freely slide on the pullwire (either forward, moving the handle proximally, or backwards, moving the handle distally). The handles described herein may further be configured so that they may be "choked up" on a pullwire and used to pull a pullwire, all with a single hand. The handle may also control the distal (sharp) end of the pullwire, by storing it within the handle. In some embodiments, as a user chokes up on a pullwire the distal end of the pullwire will be stored within the handle. For example, the further down the handle is moved onto the pullwire, the more of the distal end of the pullwire that is stored within the distal handle. Once the locking mechanism is released, a length of the pullwire can be released from the handle (i.e. "choke-down").

The devices described herein may be configured to secure/lock the pullwire to the handle so that pulling the handle will result in pulling the pullwire when the pullwire is locked into the handle. The handle may also be configured to prevent kinking of the pullwire within the handle. In general, the pullwire handle (i.e. distal handle) coupled to the pullwire will be used to pull (in a distal direction), not push, the pullwire. Alternatively, a proximal handle (for example, the handle of a tissue modification device or a handle of a neural localization device) may be used to pull the pullwire in the opposite (proximal) direction.

Figure 14A:
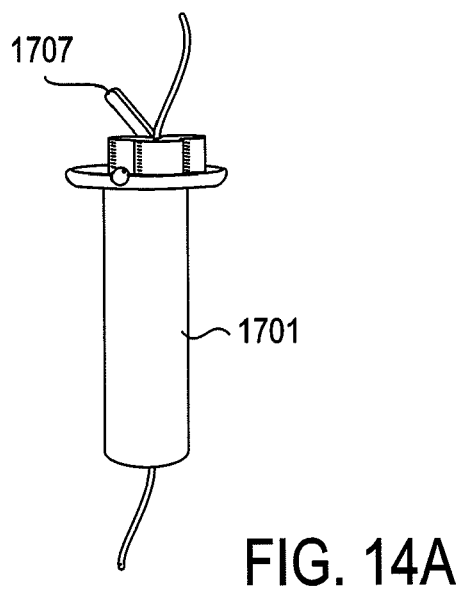
FIGS. 14A and 14B illustrate side and top views, respectively, of one variation of a handle that may be removably attached to a pullwire, as described herein.
Figure 14B:
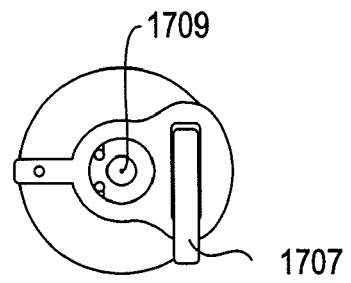

For example, FIG. 14A shows one variation of a distal handle 1701, including a central passageway 1709 through which the pullwire may be passed, and including a lock 1707 for locking the pullwire within the passageway. The lock 1707 is shown in FIG. 14B as well. FIG. 14B is a top view of the handle shown in FIG. 14A. The handle may also include a pullwire capture chamber 1922, as shown in FIG. 16B, for securing the (typically sharp) distal end of the pullwire which may otherwise pose a danger to the user. In this variation the pullwire handle may slide over the distal end of the pullwire, and then the pullwire may be looped through the pullwire capture chamber and be locked in position so that the handle may then be used to apply force to pull the pullwire distally (and thereby manipulate any of the devices described above, that may be coupled distally to the proximal end of the pullwire.

Figure 15A:
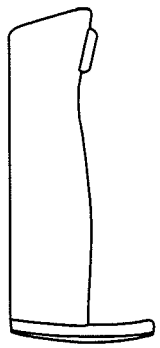
Figure 15B:
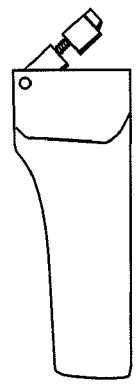
Figure 15C:
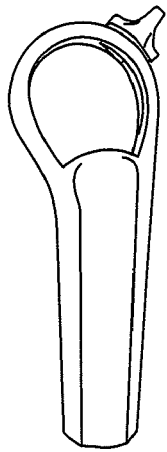
Figure 15D:
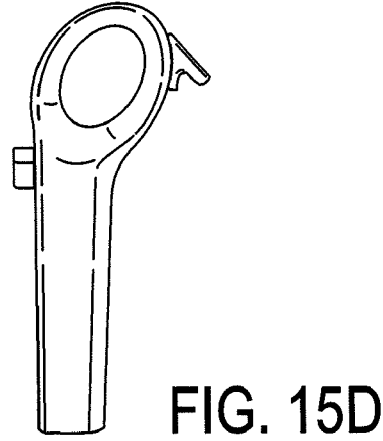
FIG. 15D is a side perspective view of another variation of a handle that may be used with a pullwire.

FIG. 15D illustrates another variation of a pullwire handle. In this variation, the pullwire handle includes a central lumen into which the distal end of the pullwire may be fed. The end of the handle may be open, and may be tapered, convex, concave, or otherwise funnel-shaped (as shown in FIG. 18D) so that the pullwire can readily be captured. In this variation, the handle including a tip capturing element that allows the distal end of the handle to be held in the handle while it is advanced (e.g. proximally). The handle may also include a latch or lock for securing the pullwire within the handle at a certain position. In some variations the handle (as shown in FIG. 15D) includes a pathway that loops the pullwire around the handle, and out of the way automatically. In some variations the handle includes a spool or path into which the pullwire may be threaded to keep it from interfering with the operation of the handle and/or pullwire.

FIGS. 15A-15D illustrate alternative variations of the pullwire handle described, and FIG. 15D shows the same variation described in FIG. 15D.

FIGS. 16A and 16B show front and side views, respectively, of the pullwire handle just described with reference to FIG. 15D. In this variation, the pullwire 1900 is first fed into the distal end of the pullwire handle which may include a funnel-shape (not shown) that communicates with an opening or internal track through the handle. This variation of a pullwire handle also includes one or more buttons or controls 1902. For example, the handle device 1901 may include one or more controls 1902 that lock or release a pullwire held within the handle, preventing or allowing the handle to slide on the pullwire. Thus, a handle may be inserted onto the distal end of a pullwire and chocked up on the pullwire. In some variations, the device includes an indicator (e.g. a visual indicator or window 1905) showing when the distal end of the pullwire is loaded within the handle. The pullwire handle may also include a loader or feeding control 1911 for advancing or loading the pullwire into the handle. In FIGS. 16A and 16B, the loader control 1911 is configured to hold the distal end of the pullwire (visible in the window 1905) and be pushed or moved along the rounded perimeter of the handle 1922 and draw the pullwire further into and around the handle, as mentioned. This curved or rounded distal end includes a channel or opening (e.g., a split) 1923 from which a portion (e.g., a portion proximal to the captured distal end) may exit the handle as a loop as the handle is choked up on the pullwire. The pullwire handle may also include a flat or marked front face 1904, as mentioned above.

FIG. 17A shows a side perspective view of the pullwire handle 1901, and FIGS. 17B and 17C show side and enlarged front (distal) views as of the same variation.

Another variation of a pullwire handle is shown in FIGS. 18A-18D. In this variation, the pullwire handle includes a proximal end 2104 into which a pullwire 2103 is fed. As mentioned above, this proximal end may be conical, funnel-shaped, or otherwise shaped to easily capture and guide the distal end of the pullwire into the handle. In some variations the proximal end is flared (e.g., trumpet shaped) or includes a flange or rim (not shown in FIGS. 18A-18D), which may help steer the pullwire into the handle and avoid injury from the often sharp end of the pullwire.

This variation also includes a control 2109 (shown as a button 2109 in FIGS. 18A and 18B) that may control the locking/unlocking of the pullwire in the handle. For example, the button may be pushed to unlock the pullwire, allowing it to be advanced into the handle, or withdrawn from the handle. In some variations, the control may be pressed or activated continuously to unlock (e.g., maintaining the hold on the button), while in other variations the control may be engaged to remain either locked or unlocked.

The handle may store the pullwire as it is inserted into the device. For example, the device may include a storage region for holding the pullwire, such as a spool around which the pullwire may be wound. This is illustrated in FIGS. 18C and 18D.

Figure 18A:
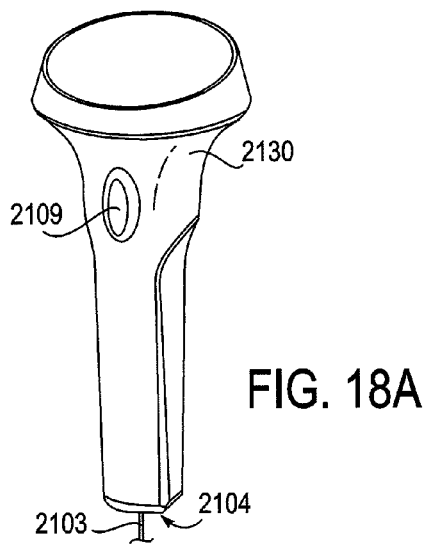
FIGS. 18A-18E show an alternative distal pullwire handle.
Figure 18B:
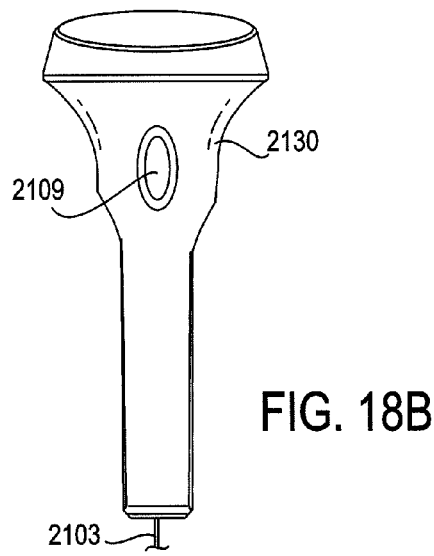
Figure 18C:
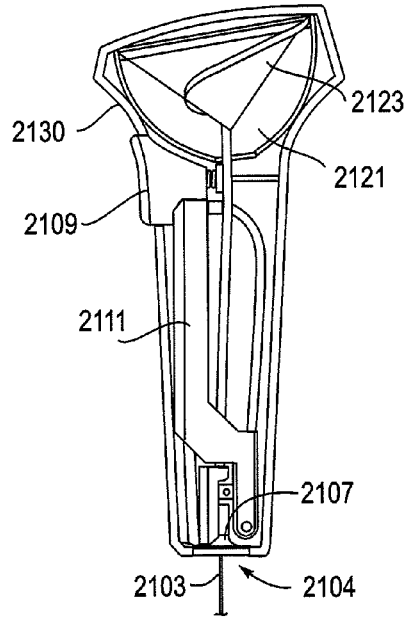
Figure 18D:
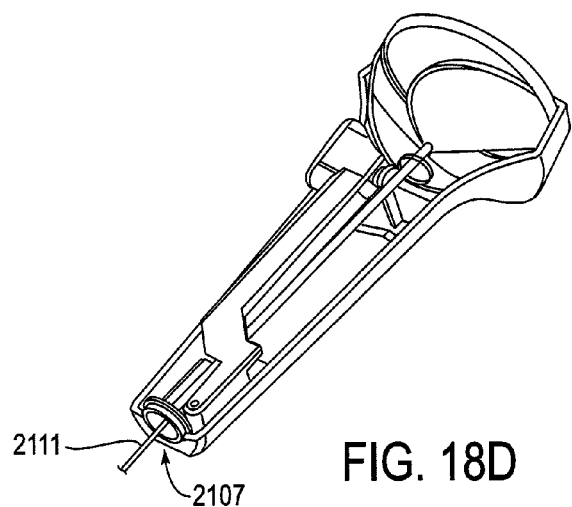

FIG. 18D shows a side view of the device of FIGS. 18A and 18B, made partially transparent to reveal the inner structures. In this variation, the pullwire 2103 may be fed from the proximal end 2104 (having a funnel-shaped feed region 2107). Pressing the button 2109 releases a lock mechanism that includes lever arm 2111 that otherwise restricts the movement of the pullwire out of the handle. In some variations, the handle may allow advancement of the pullwire into the handle even when the device is 'locked,' and only prevents withdrawal of the pullwire from the handle when the device is locked. The distal end of the handle includes a storage region 2121 having a spool 2123 that winds the pullwire around within the storage region. The spool may be fixed or rotating. In some variations the handle may include a control for winding the pullwire within the handle. For example, the handle may include a crank, lever, button, or the like, for rotating the spool and drawing the pullwire into the handle (e.g., into the storage region 2121). In one variation the distal end of the handle (e.g., the flared or bell-shaped distal end 2130) is rotatable.

Figure 18E:
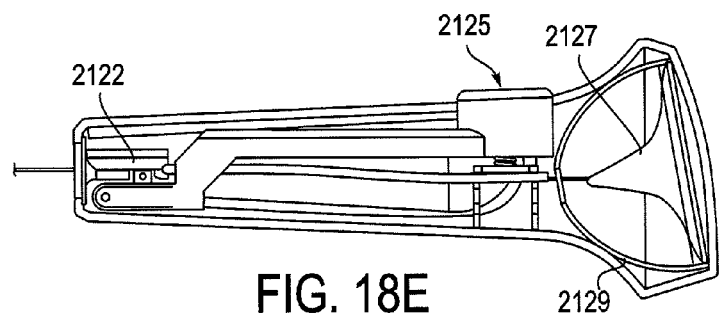

Another view of this variation of a removable pullwire handle is shown in FIG. 18E. As described above, a pullwire may enter the handle from the distal end (which has a concave or funnel-shaped opening), and is fed through the handle in a channel that leads to the storage area that is cup-shaped 2129. This cup region 2129 may enclose a surface that directs the pullwire around the chamber so that it can be wound up and stored therein. In FIG. 18E the surface is an inverted cone 2127 that deflects the pullwire so that as the pullwire is advanced, it is forced against the cup wall. Once the pullwire hits the cup wall, the pullwire buckles and wraps around the smooth interior of the cut. This variation also illustrates a locking clamp 2122 that is positioned at the proximal end and may lock or hold the pullwire within the handle housing. A control (e.g., push button) 2125 on the handle activates/deactivates the clamp or lock. For example, in FIGS. 18A-18E, the control is a push button 2125 that articulates a lever arm inward, which releases the clamp 2122 at the bottom of the handle. This opens the clamp, and releases tension on the pullwire. When the bottom is released, a spring inside the button ("thumb button") forces the lever arm back into position, thereby closing the clamp and increasing the tension on the pullwire.

FIGS. 18A to 19K illustrate a distal handle that may be attached to the distal end of a pullwire, and may be included as part of the systems described herein. The distal handle is configured to hold the distal end pullwire such that a user may pull on the pullwire, and the device that it is attached to, with a large amount of force (e.g., enough force to modify tissue such as bone and cartilage). The distal handle may hold the pullwire with a lock mechanism that is configured to withstand forces within the range of 10 lbs to 60 lbs. For example, the handle may be configured to lock and secure the handle so that it can transmit up to 40 lb of force, up to 50 lb of force, up to 60 lb of force, up to 100 lb of force, etc. without "slipping." Slipping may refer to the release of the lock so that the handle moves relative to the pullwire. Furthermore, the handle may be configured to lock and secure the handle so that it can transmit large forces without kinking or bending the wire. For example, as described in detail below, the locking mechanism in some embodiments may not damage, modify, or non-elastically bend the pullwire while still locking onto the pullwire with a great enough force such that the pullwire/distal handle can transmit a large amount of force to the proximal end of a pullwire and/or device coupled to the pullwire. In general, it may be important to transmit a large amount of force to the pullwire via the pullwire handle in order to pull a proximal end of the pullwire (and/or a device coupled to the proximal end of the pullwire) through a tight or confined space. For example, the pullwire and pullwire handle may be used to pull a tissue modification device coupled to the pullwire through a stenotic spine of a patient.

In manufacturing of the described pullwire handle, the pullwire handle may be designed for a maximum holding strength. Adaptations configured to assist with the locking strength of the handle include the materials chosen, surface finishes of the materials chosen, the shape and dimensions of the interface between the handle and the pullwire, the number of locking mechanisms (e.g., cams, etc.), the surface properties of the locking interface, mechanisms such as springs coupled to the locking mechanisms or gripping surfaces that increase clamping force, and the like. Examples of such features are described in greater detail below. For example, FIGS. 18A and 18D show one variation of a distal handle. In this variation, the pullwire handle includes a proximal end 2104 into which a pullwire 2103 is fed. As shown in FIG. 18D, this proximal end may be conical, funnel-shaped, or otherwise shaped to easily capture and guide the distal end of the pullwire into the handle. FIG. 18D shows a perspective view of the device of FIG. 18A, made partially transparent to reveal the inner structures. In this variation, the pullwire 2103 may be fed from the proximal end 2104 (having a funnel-shaped feed region 2107).

This variation also includes a control 2109 (shown as a button 2109 in FIG. 18A) that may control the locking/unlocking of the pullwire in the handle. For example, the button may be pushed to unlock the pullwire, allowing it to be advanced into the handle, or withdrawn from the handle. In some variations, the control may be pressed or activated continuously to unlock (e.g., maintaining the hold on the button), while in other variations the control may be engaged to remain either locked or unlocked. The handle may store the pullwire as it is inserted into the device. For example, the device may include a storage region 2130 for holding the pullwire, such as a spool around which the pullwire may be wound. In some embodiments, the methods of using the handle described above may include the steps of depressing the button to release the locking mechanism, inserting the distal end of a pullwire into the pullwire handle device, storing a portion of the pullwire within the pullwire handle device, and releasing the button to activate the pullwire lock to lock the pullwire within the handle.

Figure 19A:
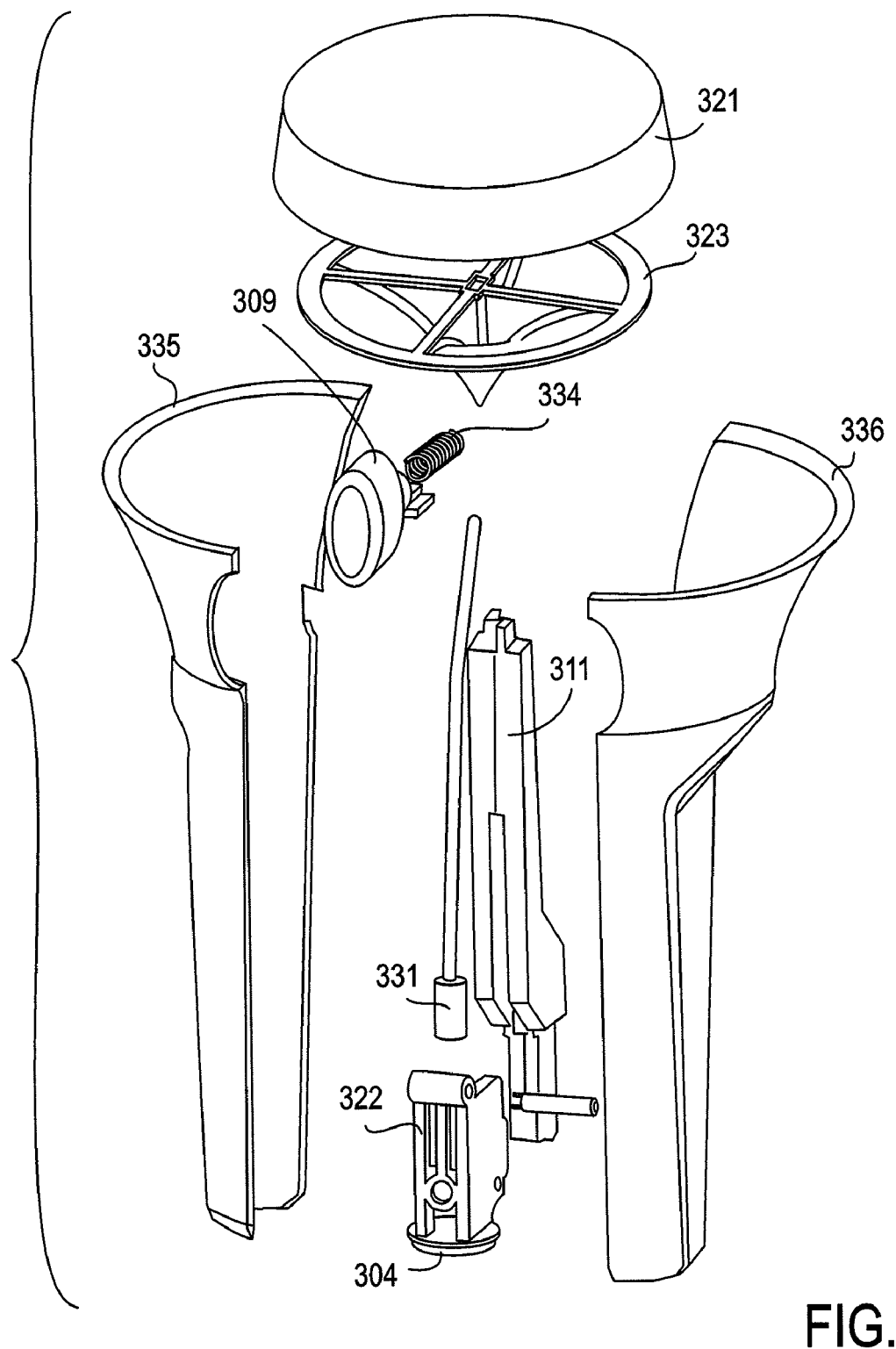
FIGS. 19A-19K show a distal pullwire handle, similar to the variation of FIGS. 21A-21E.

Another variation of a pullwire handle is shown in FIGS. 19A-19E. This variation of the distal pullwire handle is similar to the variation of FIGS. 18A and 18D. FIG. 19A shows an exploded view of this variation. As shown in FIG. 19A, the pullwire handle of this variation includes a first housing portion 335 and second housing portion 336. The housing portions may be coupled together in a clam shell configuration, or may be coupled together in any suitable configuration to form the housing of the handle and enclose the various components of the handle. In some embodiments, the housing portions may make up the handle body of the pullwire handle device. The pullwire handle (and/or handle body) also includes proximal end 304 into which a pullwire is fed. As mentioned above, this proximal end may be conical, funnel-shaped, or otherwise shaped to easily capture and guide the distal end of the pullwire into the handle. This variation also includes a control 309 (shown as a button 309 and spring 334 in FIGS. 19A-19C and 19E) that may control the locking/unlocking of the pullwire in the handle. For example, a lock mechanism of the pullwire handle may be nominally locked (i.e. always locked until unlocked by the control) and the button may be pushed to unlock the pullwire, allowing it to be advanced into the handle, or withdrawn from the handle. In some variations, the control may be pressed or activated continuously to unlock (e.g., maintaining the hold on the button), while in other variations the control may be engaged to remain either locked or unlocked.

In this variation, the handle stores the pullwire as it is inserted into the handle. As shown in FIG. 19A, the device (and/or handle body) includes a storage region 321 for holding the pullwire and a cone 323 that guides the pullwire against the inner diameter of the storage region 321. In this variation, the pullwire may be fed from the proximal end 304 (having a funnel-shaped feed region 307, as shown in FIG. 19F). Pressing the button 309 releases a lock mechanism that includes lever arm 311 that otherwise restricts the movement of the pullwire out of the handle. As the pullwire is fed from the proximal end 304, it runs through the pullwire guide tube (or internal track) 331. The pullwire exits the distal end of the pullwire guide tube such that it contacts the cone 323. As the pullwire exits the tube and contacts the cone, the geometry of the cone guides the tip of the pullwire toward the inner diameter of the storage region 321.

Figure 19B:
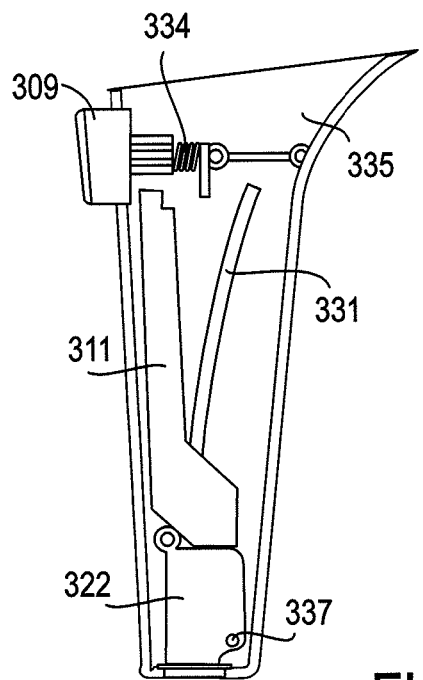
Figure 19C:
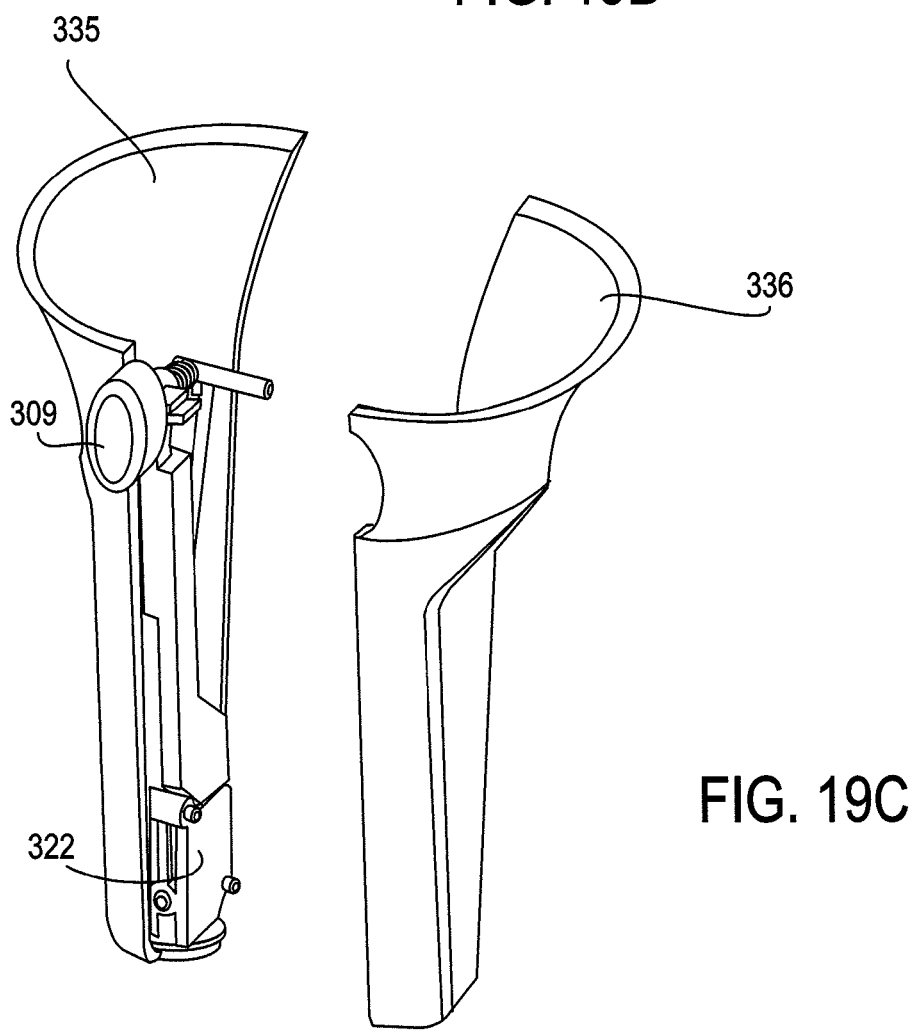
Figure 19D:
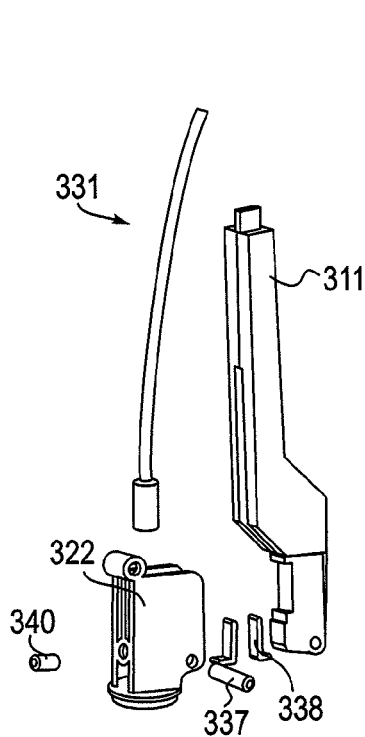
Figure 19E:
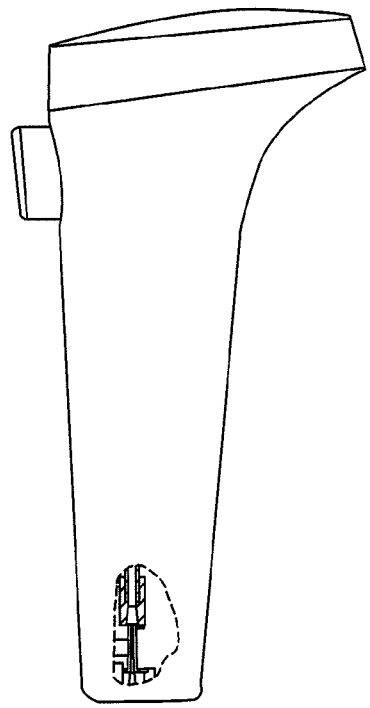
Figure 19F:
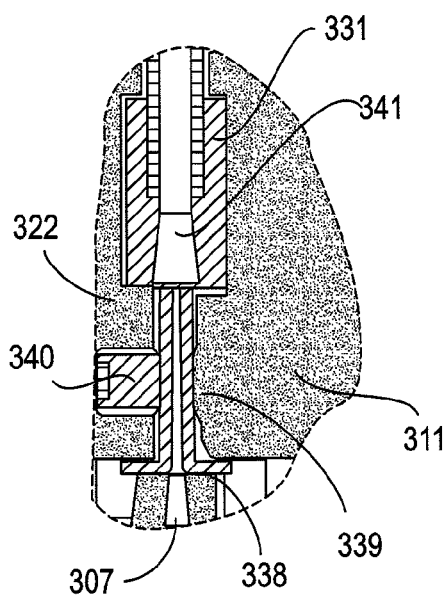
Figures 19G, 19H:
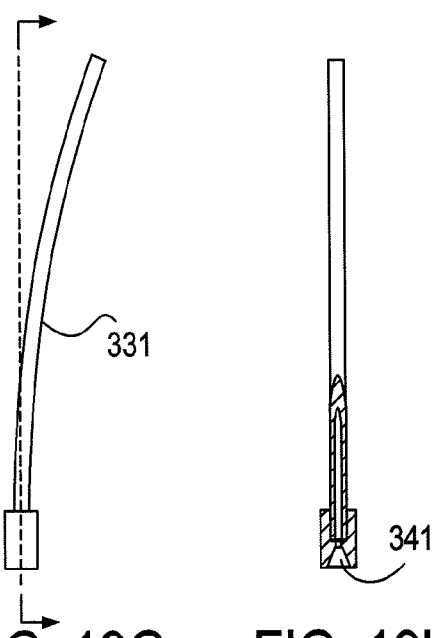
Figure 19I:
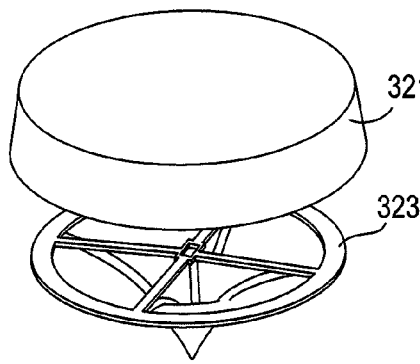
Figure 19J:
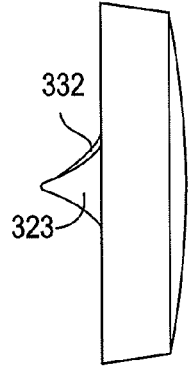
Figure 19K:
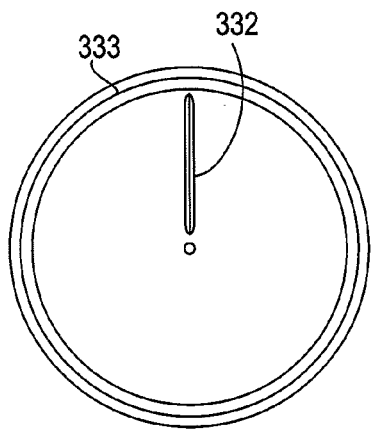

As shown in FIGS. 19I-19K, the cone 323 includes a surface that directs the pullwire around the chamber of the storage region 321 so that it can be wound up and stored therein. The surface deflects the pullwire so that, as the pullwire is advanced, it is forced against the inner wall of the chamber. Once the pullwire tip hits the chamber wall, the pullwire buckles and wraps around the inner diameter of the storage region chamber. In some variations, the surface deflects the pullwire so that as the pullwire is advanced, it is forced against a ridge 332 on the cone. Once the end of the pullwire hits the ridge 332, the pullwire buckles and wraps around the inner diameter of the storage region chamber. Alternatively (or additionally), the ridge 332 may function to guide the pullwire, particularly after it has begun to buckle, away from the cone 323 and to continue to wrap within the chamber 321. The ridge 332 may therefore function to prevent the pullwire from hitting the chamber wall and buckling back onto cone 323 and jamming against the cone. Alternatively, the surface deflects the pullwire so that as the pullwire is advanced, it is forced against a ridge or pin 333 on the inner diameter of the chamber of the storage region. Once the end of the pullwire hits the ridge or pin 333, the pullwire buckles and wraps around the inner diameter of the storage region chamber.

FIG. 19B shows a partial cross sectional view and FIG. 19C shows a partially exploded view of this variation. This variation also illustrates a clamp housing 322 that is positioned at the proximal end and encloses the clamp 338 (as shown in FIGS. 19D-19F) that may lock or hold the pullwire within the handle housing. A control (e.g., push button 309 coupled to spring 334) on the handle activates/deactivates the clamp or lock. The push button 309 articulates a lever arm 311 outward and/or clockwise about a pin 337, which releases the clamp at the bottom of the handle. This opens the clamp, and releases tension on the pullwire. When the button is released, the spring 334 forces the lever arm 311 back into position, thereby closing the clamp and increasing the tension on the pullwire.

FIG. 19D shows an exploded view of the lock mechanism of the pullwire handle. FIG. 19E shows a partial cross-section through the handle and FIG. 19F shows a detail view of the section of FIG. 19E. As shown, this variation of the lock mechanism includes a clamp housing 322. The clamp housing, as shown in FIGS. 19D-19F includes a funnel-shaped feed region 307 at the proximal end of the handle into which the pullwire is fed. The clamp housing 322 also houses the clamp 338 and clamp adjustment set screw 340. The clamp functions to provide an increased surface area with which to grip and lock the pullwire into place. The increased surface area may also help to prevent damage, kinking, or bending of the pullwire as described above. In some embodiments, the clamp is designed to "float" within the clamp housing. As the tension of the pullwire increases (i.e. a user is pulling on the pullwire handle with increased force applied to the pullwire or the user simply pulls the pullwire handle in a distal direction to place the pullwire in tension), the clamp slides towards the proximal end of the handle thereby, allowing the cam to further rotate towards the pullwire; thereby, increasing the holding and locking strength on the pullwire.

Alternatively, rather than including a clamp, the cam surface 339 (as described below) could directly contact the pullwire, or a shim or other suitable strip of material may be used to increase the surface area upon which the cam surface may apply a force to the pullwire to hold the pullwire in place. The clamp adjustment set screw 340 may be threaded (or otherwise coupled to) the clamp housing 322 and may function to tighten or loosen the arms of the clamp 338. The clamp housing is coupled to the lever arm 311 with pin 337 about which the lever arm rotates.

As shown, this variation of the lock mechanism also includes a lever arm 311. At the distal end of the lever arm, the lever arm is coupled to button 309. At the proximal end of the lever arm, the lever arm includes cam surface 339 and, as mentioned above, is coupled to the clamp housing 322 via pin 337. As mentioned above, the push button 309 articulates the lever arm 311 outward and/or clockwise about a pin 337. This rotates the cam surface 339 away from the clamp 338 which releases the clamp and allows the clamp to open up and release tension on the pullwire. When the bottom is released, the spring 334 forces the lever arm 311 back into position, thereby rotating the cam surface 339 against the clamp, effectively closing the clamp and increasing the tension on the pullwire.

In any of the variations described herein, the locking mechanism in the handle that holds the pullwire may be a clamping mechanism that includes a gripping surface. This gripping surface may be sized so that it provides significant surface contact with the pullwire from two or more sides. For example, the gripping surface may include a shim surface that is substantially parallel to another (e.g., a fixed or a similar clamp) surface, between which the pullwire passes and is gripped when the lock/clamp is activated. This surface may be a separate element (e.g., a shim element) or it may be a portion of the locking arm or cam, as described and exemplified below. In some variations the clamp/lock mechanism includes a tubular surface or sleeve into which the pullwire passes and is gripped, for example, by compressing or inflating the sleeve/surface. The surface(s) that are locked against the pullwire may be textured to aid in gripping the pullwire. For example, the surface may be rough or may include channels (e.g., transverse channels). The surface(s) may be treated, coated, or formed of a grip-enhancing material having a relatively higher surface friction when engaging the pullwire. For example, the surface may be formed of a tacky or sticky material. As will be described below, a gripping/clamping surface may also be configured to prevent "kinking" of the pullwire in the lock.

The gripping/clamping surface may be any appropriate length. The length may depend upon the locking mechanism. For example, when multiple locking mechanisms are used, the surface may be longer. In some variations the surface(s) is between about 1 mm (or 2 mm, 3 mm, 5 mm, 10 mm, 15 mm, 20 mm, 50 mm, etc.) and about 2 mm (or about 3 mm, 5 mm, 10 mm, 15 mm, 20 mm, 50 mm and 100 mm).

Figure 20:
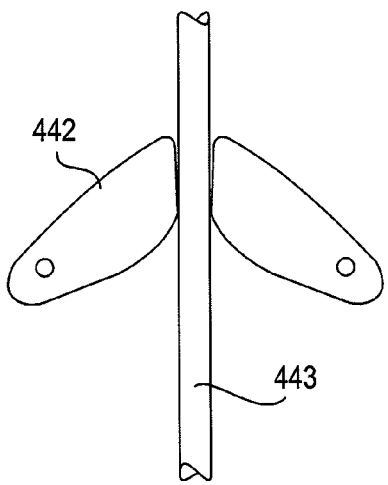
FIGS. 20-24C show various alternative lock mechanisms of a distal pullwire handle.

FIGS. 19G and 19H show a side and cross sectional view respectively, of a pullwire guide tube (or internal track) 331. As shown in cross section in FIG. 19H, the pullwire guide tube of this variation includes a proximal end 341 into which a pullwire is fed as it exits the clamp and clamp housing as described above. Proximal end 341 is configured to capture and align the tip of the pullwire as the pullwire passes over the clamp blocks 338. As shown, this proximal end 341 may be conical, funnel-shaped, or otherwise shaped to easily capture and guide the distal end of the pullwire into the pullwire guide tube 331 and up to the storage region. FIG. 20 shows an alternative embodiment of a lock mechanism including more than a single cam surface. This embodiment includes two opposing cams 342 that rotate toward one another (curved arrows) to grip and hold a pullwire 343. In this embodiment, the lock mechanism may not include a lever arm and/or control button. Alternatively, the lock mechanism may be a passive lock mechanism such that as the pullwire moves in the proximal direction (i.e. out of the handle) the pullwire pulls and rotates the opposing cams distally, or downward (as shown by the down arrow in FIG. 20). The cams in this embodiment are configured such that as they are rotated downward, they apply more and more force onto the pullwire 343, thereby locking the pullwire into place. If the pullwire is pushed up (or distally) however, the cams will rotate in the opposite direction, and will allow the pullwire to be moved in that direction (i.e. into the handle). In some embodiments, the mechanism may include a plurality of opposing cam pairs.

Figure 21:
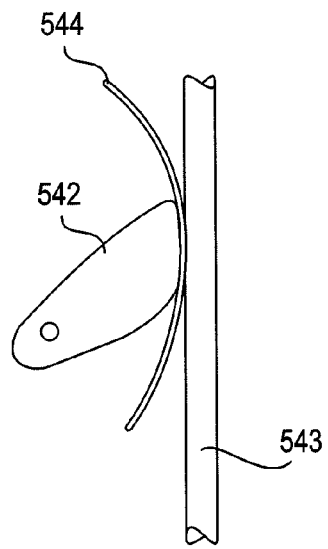

FIG. 21 shows an alternative embodiment of a lock mechanism including a shim element 544. As mentioned above, the shim element 544 functions to distribute the force from the cam 542 along a larger surface area of the pullwire 543. A shim element 544 (or other elongate locking/contacting surface) may also prevent the pullwire 543 from kinking under the applied within the lock mechanism. In some variations the length (along the long axis that the pullwire extends) and the width (perpendicular the long axis) may be selected to prevent kinking In variations in which a separate shim element (e.g., clamping surface/element) is not used, the cam or locking mechanism may be configured to contact the pullwire directly and may be configured to have an integral pullwire contacting surface, as described above. In such variations the increasing the diameter of the contacting surface of the cam mechanism may also function to prevent the pullwire 543 from kinking under the applied force within the lock mechanism. In some embodiments, the shim element 544 may be made from a stainless steel or other suitable metal material, while the cam 542 may be made from a plastic or other suitable molded material. This may reduce cost and/or increase reliability of the lock mechanism.

Figure 22A:
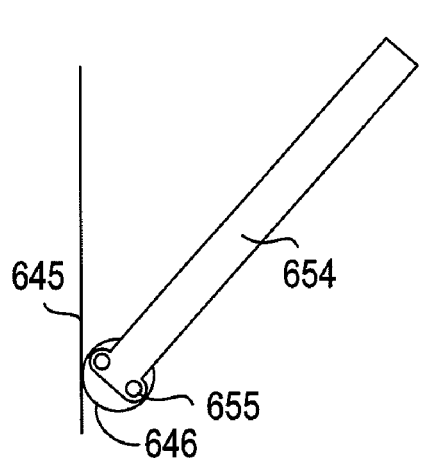
Figure 22B:
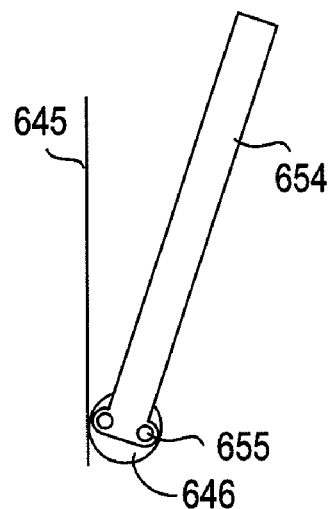

FIGS. 22A and 22B show an alternative embodiment of a lock mechanism including a cam mechanism. As shown in FIG. 22A, the cam mechanism includes a fixed surface 645 and a cam surface 646. In FIG. 22A, the cam mechanism is in an open position, wherein the pullwire may pass through the mechanism between the fixed surface 645 and a cam surface 646 up into the pullwire handle. A lever arm 654 is coupled to the cam surface 646 such that, as shown in FIG. 22B, as the lever arm rotates inward and/or counter-clockwise, this rotates the cam surface 646, about pin 655, toward the fixed surface 645 and applies a force on the pullwire, for example, locking it in place. Additionally, in this configuration, as the wire is pulled out of the distal handle and/or the distal handle is pulled off of the pullwire the cam mechanism is configured to tighten on the pullwire as it is pulled down and/or out of the distal handle. As mentioned above, any of these variations may also include a shim or other contact/gripping element and/or surface.

Figure 23A:
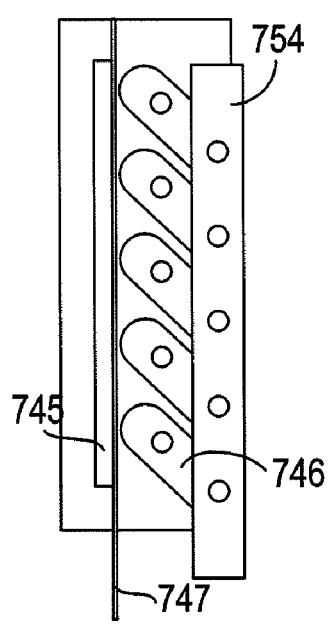
Figure 23B:
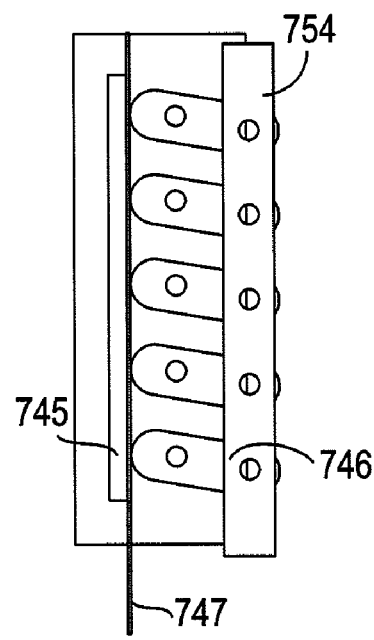

In alternative variations, the locking mechanism may include multiple cam surfaces and/or multiple lever arms to increase the locking force applied to the pullwire. The pullwire in this variation is locked by series of cam surfaces which provide redundancy in holding wire. An initial clamp force may be provided by a spring or button (as described above) coupled to a lever arm for example, forcing the cams against the wire. A secondary clamping force may be provided as the wire is pulled out of the distal handle and/or the distal handle is pulled off of the pullwire, wherein the wire is effectively pulling down on clamp mechanism. The harder the wire is pulled the more force the clamp applies. As shown in FIG. 23A, the lock mechanism includes multiple cams 746 coupled to a single arm 754. The cams may function to grip a pullwire 747 against surface 746. In FIG. 23A, the cam mechanism is in an open position, wherein the pullwire 747 may pass through the mechanism between the fixed surface 745 and a cam surface 746 up into the pullwire handle. Arm 754 is coupled to the cam surfaces 746 such that, as shown in FIG. 23A, as the arm moves upward, the cam surfaces rotate counter-clockwise and/or toward the fixed surface 745 locking pullwire 747 into place. Once locked into place, as shown in FIG. 23B, the arm 754 may be moved down such that the cam surfaces rotate clockwise and/or away from the fixed surface 745 releasing the pullwire 747. In some embodiments, the cams 746 may all be directly coupled to arm 754 such that the cams move in unison. Alternatively, the cams coupled to arm 754 such that they have the ability to "float" as described above. In other words, as the tension of the pullwire increases (i.e. a user is pulling on the pullwire handle with increased force applied to the pullwire), the "floating" cams further rotate; thereby, increasing the holding and locking strength on the pullwire. The "floating" cams may be coupled to arm 754 such that when the cams are moved to the open, or disengaged position, they all open in unison or at about the same time.

Any of the handle variations described herein, including that shown in FIGS. 21-23B, may include a disengaging/engaging control configured to release the lock. For example, in FIG. 23B, a disengaging/engaging control may be configured to move the locks (e.g., cams) towards or away from the fixed surface 745.

Figure 24A:
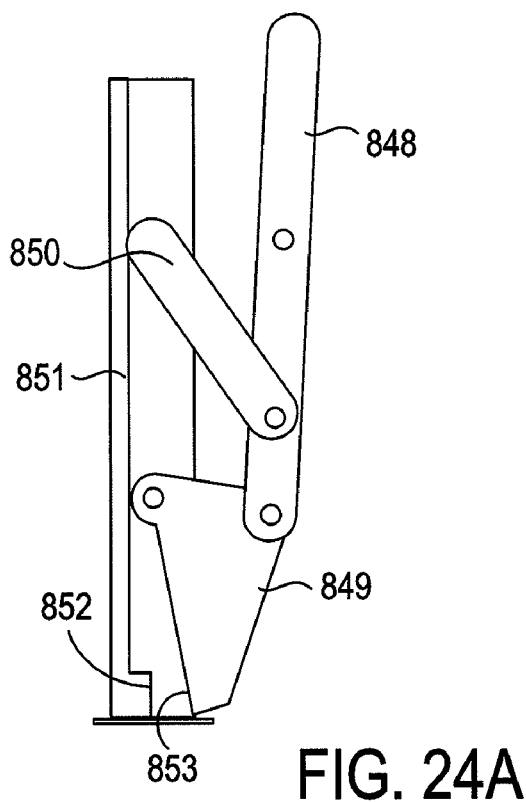
Figure 24B:
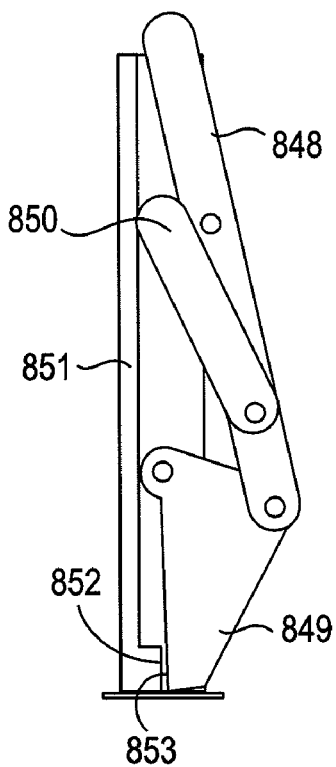
Figure 24C:
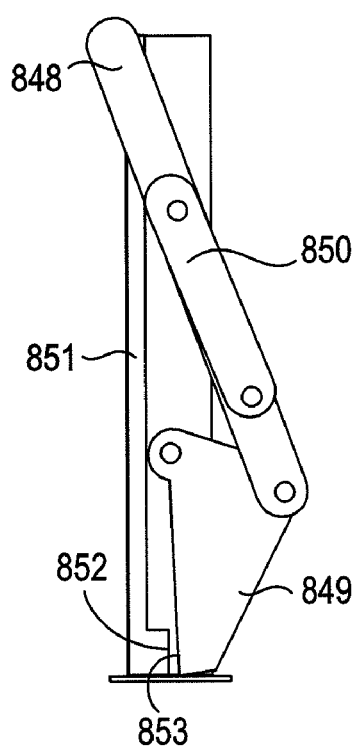

In alternative variations, as shown in FIGS. 24A-24C, the locking mechanism comprises a four bar linkage, such as an over-center four bar linkage. In this variation, the four bar linkage mimics a Vise-grips or locking pliers. The four bar linkage includes bars 848, 850, 849, and 851. Bars 849 and 851 include gripping surfaces 853 and 852, respectively. Similar to Vise-Grips, the lock mechanism can lock the pullwire into position using an overcenter action. Bar 848 functions as a lever. As shown in FIG. 24A, bar 848 is in an open position. As bar 848 is pushed toward bar 851, as shown in FIGS. 24B and 24C, the linkage forces the gripping surfaces toward one another with a large amount of force. As shown in FIG. 24B, bar 848 is moved such that it is moved over its center point (i.e. overcenter) and the linkage locks the jaw (bars 849 and 851) of the pliers onto the gripped object. The bars may alternatively be arranged in any other suitable configuration to provide a large gripping or locking force between at least one gripping surface and the pullwire.

Figure 25A:
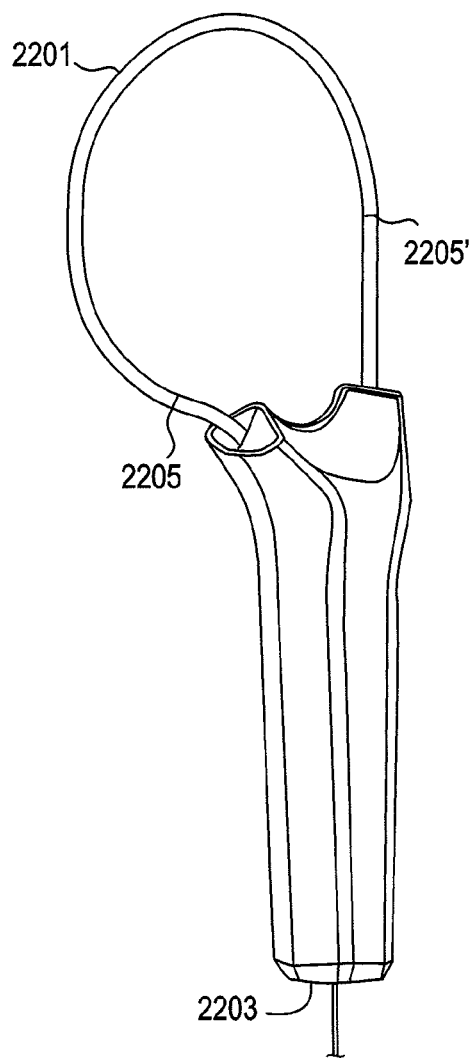
FIGS. 25A-25B show perspective views of another variation of a handle for the distal end of a pullwire. This variation includes a passive loop configuration for managing the distal end of the pullwire.
Figure 25B:
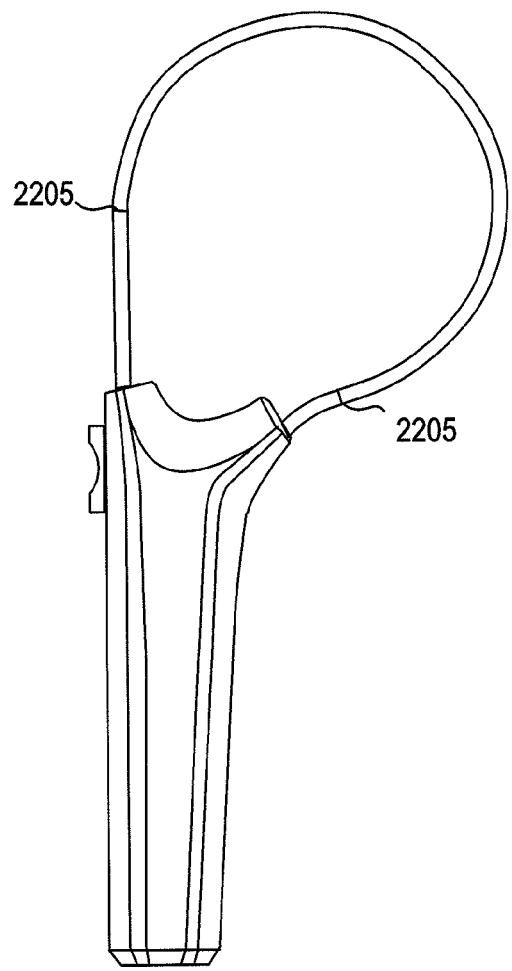

FIGS. 25A and 25B illustrate another variation of a removable/adjustable handle for the distal end of a pullwire. In this variation the distal end includes a guide channel 2201 through which the pullwire may be fed. Once the pullwire is passed from the funnel-like opening in the proximal end 2203 of the handle (not visible), it may pass through the body of the handle, and into and around this loop region. The user is protected from the sharp distal tip, because it is within the body of the handle (and this distal loop). As the distal end of the pullwire passes out of the loop and back into the solid region of the handle, it may be held (releasably) in the handle. However, if the handle is further "choked-up" on the pullwire such that more pullwire is fed into the handle, the distal tip of the pullwire will remain within the handle, however the loop 2201 may 'break away' from the body of the handle, as shown in FIGS. 23C-23E, allowing more and more pullwire 2310 to be threaded distally into the handle. This progression can be seen in FIGS. 23B, 23C, 23D, and then 23E. The break-away lock may therefore allow the loop of pullwire to continue to be taken up, while controlling the sharp tip. Thus, in some variations, this loop may be frangibly connected to the body of the device, or it may include a breakable region 2205, 2205', so that pressure from the pullwire within may allow it to separate after guiding the tip of the wire into the handle and forming a loop that can then expand further.

Figure 26A:
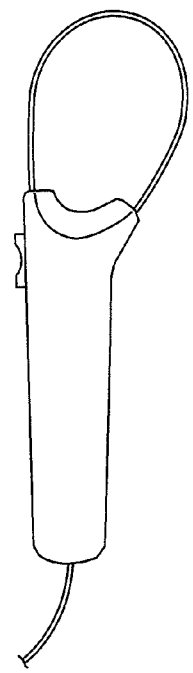
FIG. 26A shows another variation of a pullwire handle similar to that shown in FIGS. 25A and 25B.
Figure 26B:
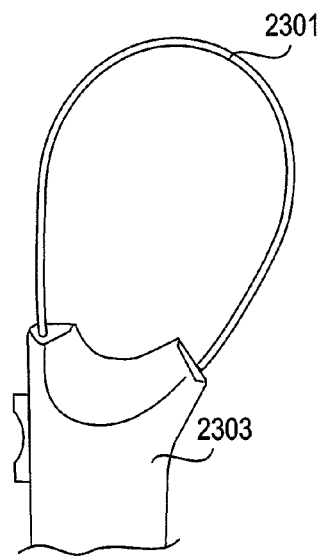
FIGS. 26B-26G illustrate the operation of the distal handle shown in FIG. 26A.
Figure 26C:
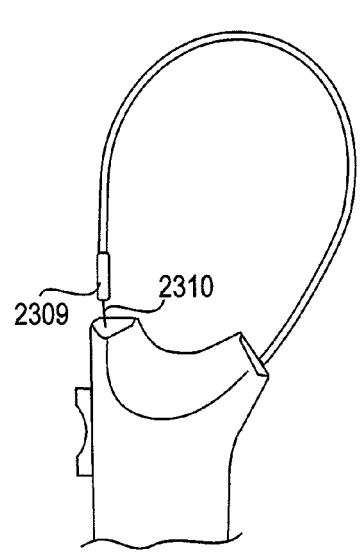
Figure 26D:
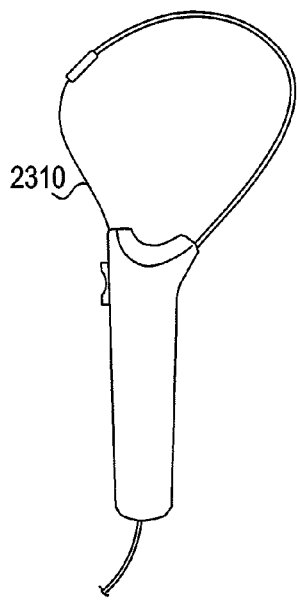
Figure 26E:
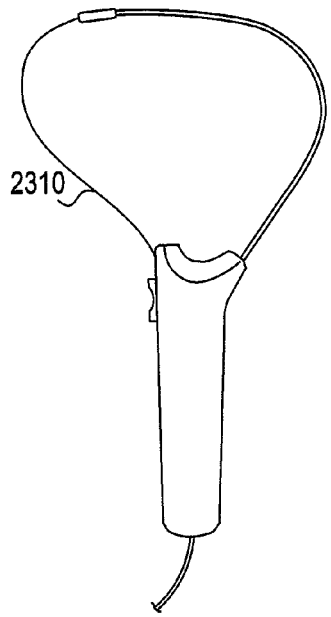
Figure 26F:
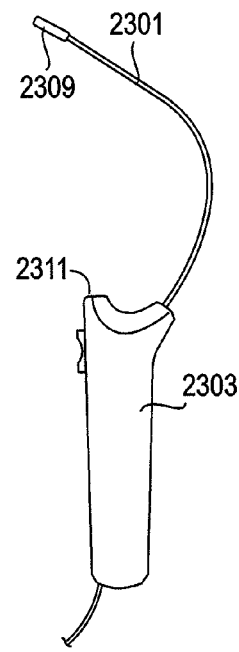
Figure 26G:
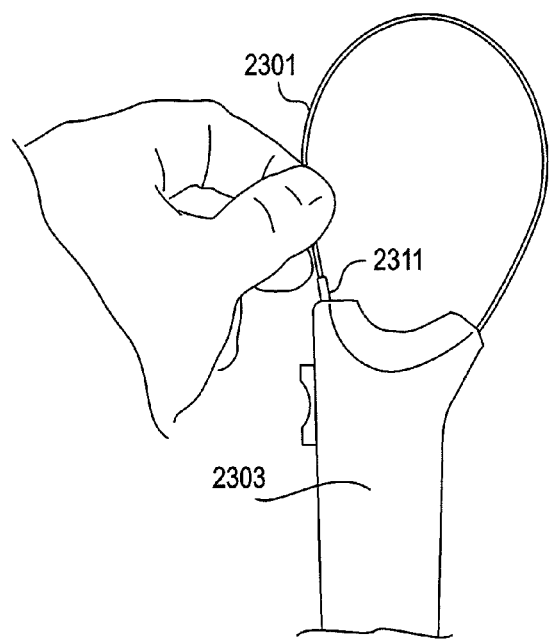

Another variation of a pullwire handle having a distal pullwire handle that is removable and reusable (similar to the one described above in FIGS. 25A and 25B) is shown in FIGS. 26A-26G. For example, FIG. 26A shows a pullwire handle having a separable guide region 2301 for a pullwire. FIGS. 26B-26G illustrate operation of this variation. For example, in FIG. 26B shows the pullwire handle in a "set" state, in which the guide portion (capture tube 2301) is attached at both ends to the base of the handle 2303. The pullwire 2310 may be inserted from the proximal end of the handle (not shown), threaded through the handle body or base, and into the capture tube, where it passes around and through the capture tube. In FIG. 26C, the distal end of the pullwire reaches a stop or fixing point in the handle, where further advancement of the distal end is prevented. The distal end of the pullwire may be secured in the handle. For example, the distal end may be secured by a gel, adhesive, clamp, or the like, that holds it in place (through it may be withdrawn by the application of appropriate force). As a result of bottoming out at the stop, the force applied to advance the pullwire in the handle may cause the detachable portion of the capture tube 2309 to release from the handle as shown. Further advancement of the pullwire is shown in FIG. 26D; the pullwire 2310 continues to loop out of the handle. The handle may include a lock and a control to release/close the lock to secure the more proximal end of the pullwire in the handle. The pullwire can be removed from the handle by pulling it proximally, until the distal end is withdrawn from the stop and then out of the handle completely, as shown in FIG. 26F. The handle may be re-used by resetting the capture tube. The capture tube can be reset by inserting the end of the capture tube 2309 into the detachable lock in a recess in the handle 2311, as illustrate in FIG. 26G.

The end of the capture tube 2309 may be removably secured in any appropriate manner. For example, the capture tube 2309 may be secured by a friction fit (e.g., a snap fit, etc.), a magnetic connector, or the like. In some variations, the detachable region of the capture tube includes a magnet or a ferrous region that mates with another magnetic (or ferrous region) on the handle body that receives the detachable region.

Figure 27A:
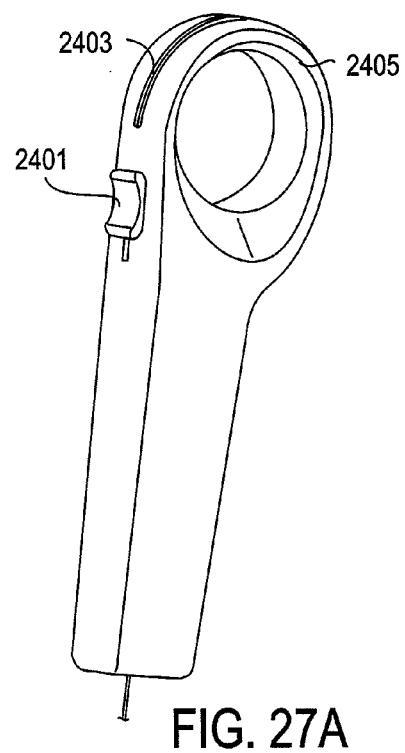
FIG. 27A shows a perspective view of another variation of a pullwire handle.

FIG. 27A shows another variation of a distal handle including a window or slot 2403 through which the pullwire may pass after it has been fed into the handle and the distal end of the pullwire has been secured. As the pullwire is fed into the handle, a loop of pullwire may pass out of the window or slot. A control (e.g., slider or button) 2401 may be used to control the opening and closing of the window, and may be used to secure the distal end of the pullwire in the handle, as well as a more proximal end of the pullwire. This is illustrated in FIGS. 27B-27D and again in FIGS. 27E-27H.

Figure 27B:
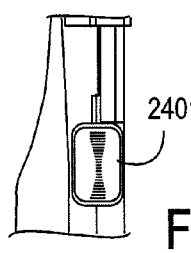
FIGS. 27B-27D illustrate operation of the controller for the pullwire handle.
Figure 27C:
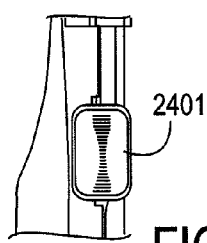
Figure 27D:
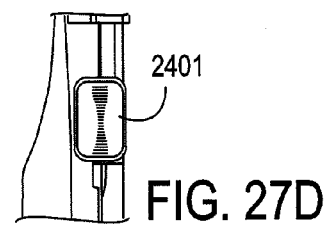
Figure 27E:
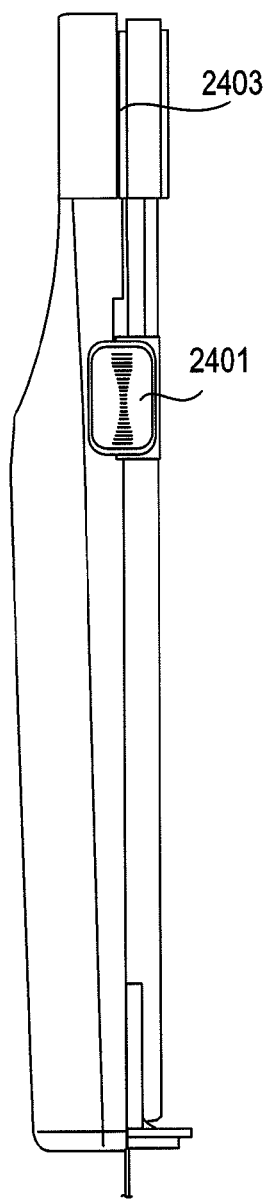
FIGS. 27E and 27F show side and cross-sectional views, respectively, of the handle of FIG. 27A during a first operational state.
Figure 27F:
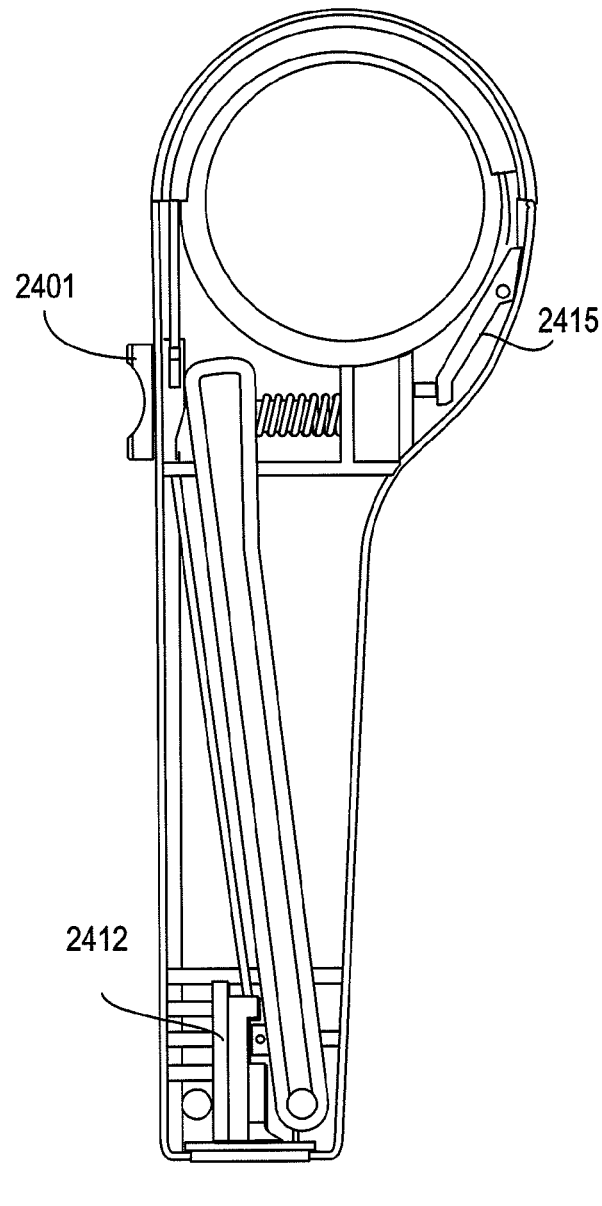

For example, in FIGS. 27B-27D, the different positions of the control 2401 are illustrated in this variation. In FIG. 27B the control (slider 2401) is in a first position, a bottom position, corresponding to the closing of the window and setting up of the handle to accept and lock the distal end of the pullwire when it is fed into the handle initially. As before, the pullwire may be passed into the body of the handle, around the closed window region 2405 to a stop on the other side of the looped window region. Once the pullwire reaches the stop, the control may be changed to a second position as illustrated in FIG. 27C. In some variation the handle may detect the pullwire tip at the stop. As before, the pullwire tip may be maintained at the stop by a clamp, adhesive, gel, or the like. When the control is in the second position, the window 2403 opens to allow the wire to bow out of the window so that the loop of wire can expand outwards (similar to the variation shown in FIG. 26E, though without a capture tube. When the control is in position two, the wire may be freely slid within the distal handle. Once the wire is fed into the handle a desired amount, the control may be moved to a third position, locking the proximal end of the wire within the handle body so that tension may be applied to the pullwire by the handle (e.g., when it is used for a decompression, as referred to above). In FIGS. 27B-27D the control is a button or slider, however any appropriate control may be used, including dials, switches, or the like. Also, in some variations the control may integrate the functions described at some of the three positions mentioned above, so that only two positions are necessary (e.g., one for locking/unlocking the distal end and one for locking/unlocking the proximal end.

Figure 27G:
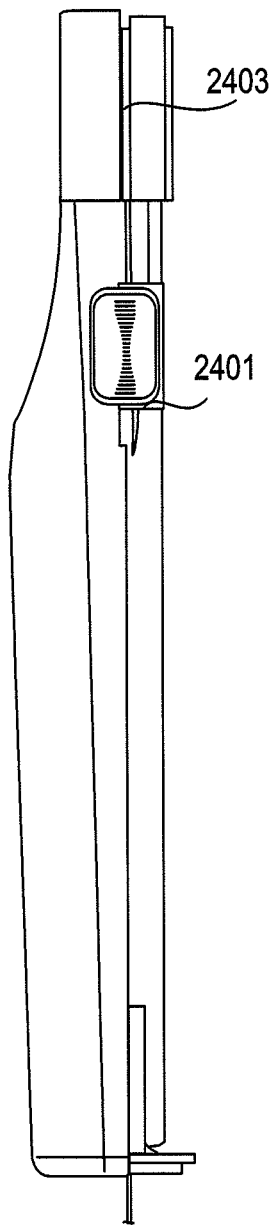
FIGS. 27G and 27H show side and cross-sectional views, respectively, of the handle of FIG. 27A during a third operational state.
Figure 27H:
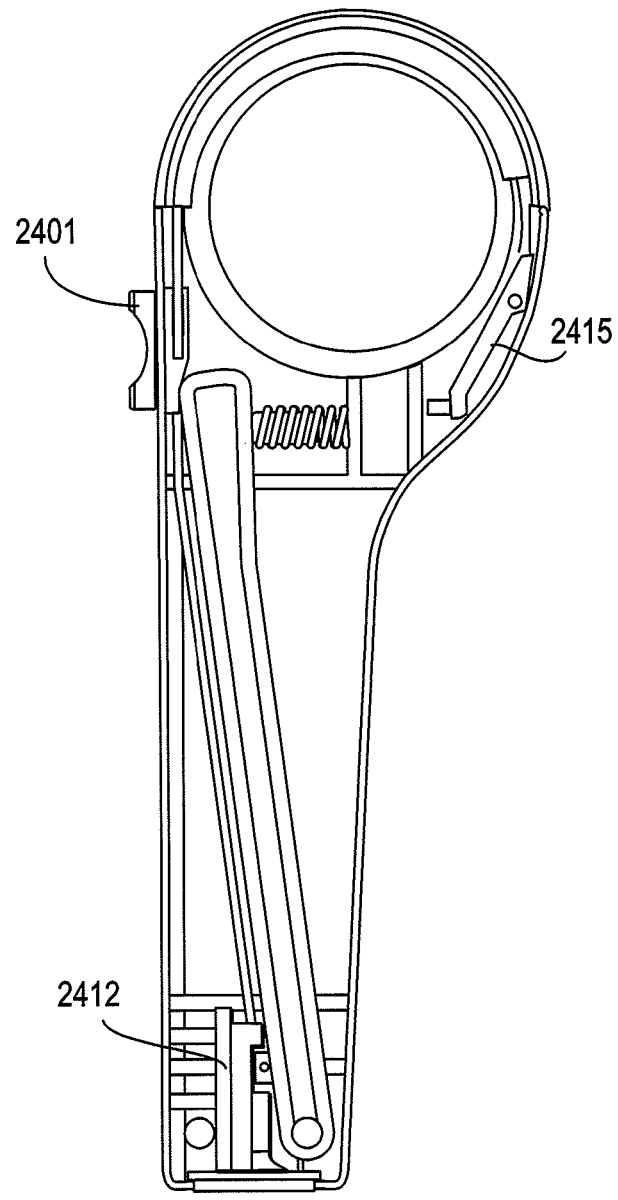
Figure 28A:
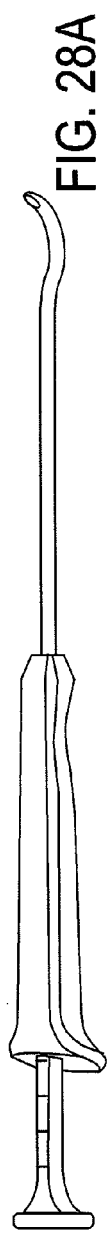
FIGS. 28A-28F illustrate another variation of a system with tools for treating spinal stenosis including two variations of a pullwire positioning probe tool (28A and 28B), a flexible neural localization tool (28C), a tissue modification tool (28D), a removable pullwire handle (28E), and a pullwire (28F).
Figure 28B:
Figure 28C:
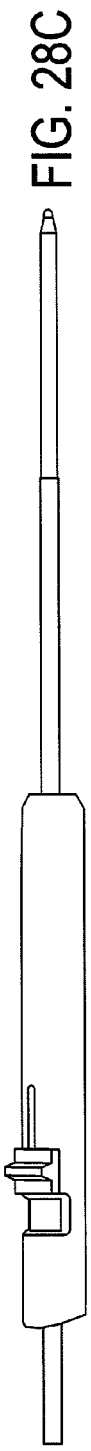
Figure 28D:
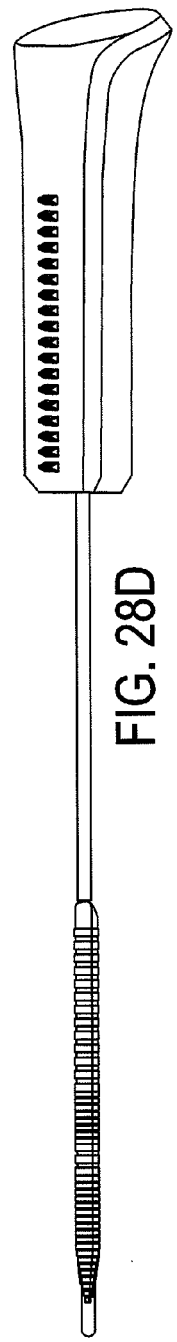
Figure 28E:
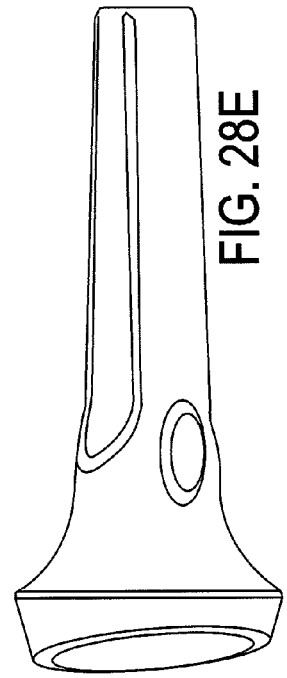
Figure 28F:
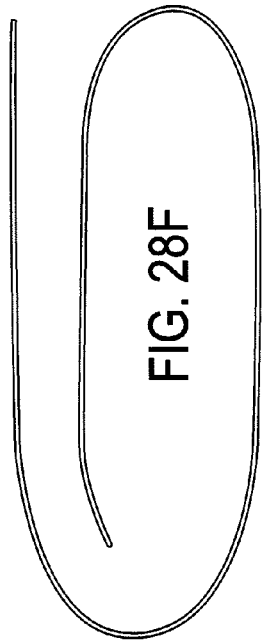

FIGS. 27E to 27H show cross-sectional views through the variation shown in FIG. 27A during two of the three steps mentioned above for FIGS. 27B-27D. For example, in FIGS. 27E and 27F, the window or slot 2403 is closed, and the button 2401 is in the bottom (first) position. The pullwire may be fed through the device and around the curved window region to engage with the distal lock 2415; a proximal lock 2412 is opened completely so that the pullwire may slide through the proximal portion of the handle. When the slider 2401 is in the second (middle) position (not shown) and the window is opened to allow the wire to bow out of the handle while the distal end of the pullwire is held by the stop (clamp) 2415. The proximal clamp 2412 remains open so that more pullwire can be drawn or pushed into the handle. In FIGS. 27G and 27H, the slider 2401 is in the third (top) position, and the window 2403 is still opened, and a loop of pullwire may be passing out of the window. However, in this position the lower clamp or lock 2412 at the proximal end of the handle is engaged so that the proximal portion of the pullwire in the handle is locked in position.

FIGS. 28A-F illustrate a system including various embodiments of the devices described above. Any of the devices (and embodiments of these devices) described herein may be included in a system for treating spinal stenosis. In some variations, more than one type of tool or handle may be included. For example, in the system shown in FIGS. 28A-28F, two variations of probes (28A and 28B) are illustrated.

Another variation of a probe is illustrated in FIG. 29A. In this variation, the probe includes an outer cannula 2601 that is connected to a handle including a proximal grip region 2607. The outer cannula is typically stiff, and may be formed of a metal (e.g., stainless steel, Nitinol, etc.), and is curved slightly at the distal end, as mentioned above. An inner member 2603 is slideably disposed within the outer cannula, and is coupled to a plunger or other control 2605 at the proximal end, so that it can be extended and retracted from the distal end of the outer cannula. The inner member 2603 is typically curved so that when extended from the distal end of the outer cannula 2601, it curves, as shown in FIG. 29A. In some variations the inner member of the probe is configured so that a distal tip region 2609 is always outside of the outer cannula 2601; in other variations, the inner member is configured to be completely retracted within the outer cannula. The inner member may also be referred to as an inner cannula, since it typically includes a central pullwire lumen 2614, through which a pullwire may be extended distally after the probe has been positioned. The inner member may therefore guide the pullwire through the curved distal end and steer placement of the pullwire.

The inner member (or cannula) shown in FIG. 29A and in cross-section in FIG. 29B is a flattened elongate body including a central pullwire lumen 2614. In general, the pullwire lumen extends all the way from the proximal end of the device (e.g., through the plunger 2605) and out of the distal tip 2609 of the inner member 2603. In this variation, the inner member includes one or more (two support members 2612, 2612' are shown in FIGS. 29A and 29B) support members that extend along the length of the inner member. The support members are typically solid members, such as wires, rods, or the like. The support members are also typically curved, so that the inner member curves as it is extended distally out of the outer cannula, as shown in FIG. 29A. The support members may be, for example, a wire formed of metal such as stainless steel or a shape memory alloy such as Nitinol. The support member may be positioned within a lumen through the flattened elongate body, as shown in FIG. 29B. In this variation, two support members (though they may be formed using a single wire that extends the length of the device and doubles back around one end to extend back along the length of the device) extend along the longitudinal length of the device. The support members shown in FIGS. 29A and 29B are Nitinol wires that are pre-biased to have a curved shape. The support members extend to either side of the (central) pullwire lumen. In other variations, the support member(s) may extend centrally, and the pullwire lumen may be located to one side.

In some variations the body of the inner member may be formed of a flexible material, such as a polymer, rubber, or the like, that is formed or extruded to have a pullwire lumen, and lumen for the support member(s). For example, the three lumen may be formed in a flat/oval extrusion to form the body of the inner member. In FIG. 29B, the outermost lumen house two Nitinol wires that run down these lumen to either side of the central lumen.

Figure 30A:
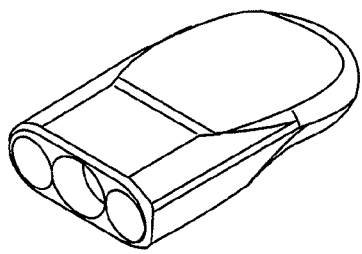
FIGS. 30A-I illustrate alternative views of one variation of the distal end of a probe such as the probe shown in FIG. 29A.
Figure 30B:
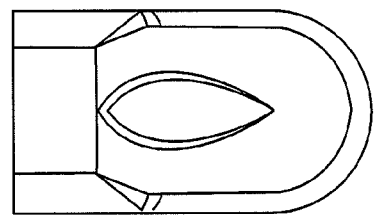
Figure 30C:
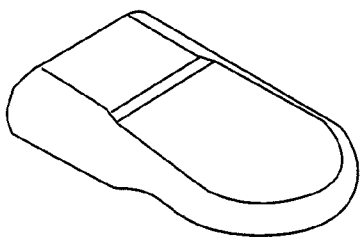
Figure 30D:
Figure 30E:
Figure 30F:
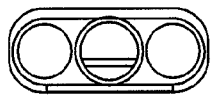
Figure 30G:
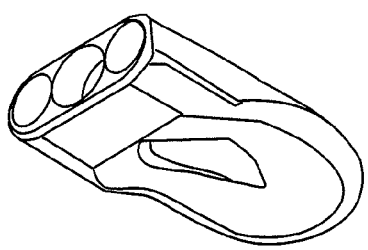
Figure 30H:
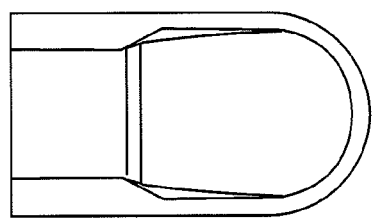
Figure 30I:
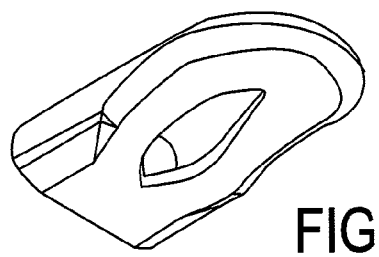
Figure 31A:
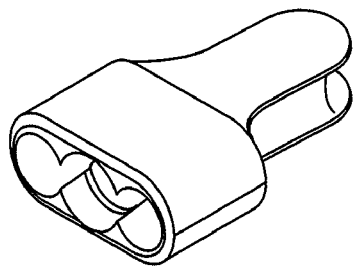
FIGS. 31A-I illustrate alternative views of another variation of the distal end of a probe such as the probe shown in FIG. 29A.
Figure 31B:
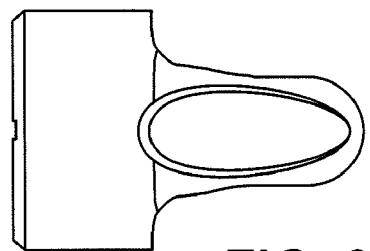
Figure 31C:
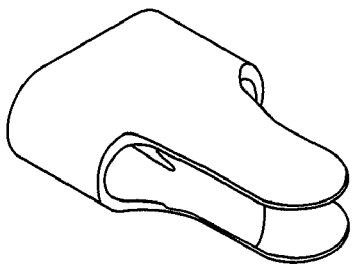
Figure 31D:
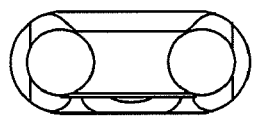
Figure 31E:
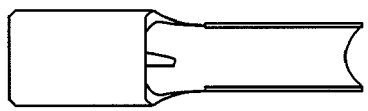
Figure 31F:
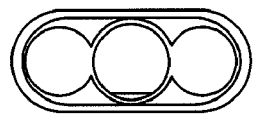
Figure 31G:
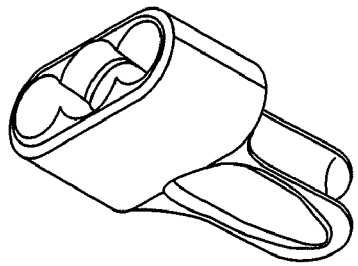
Figure 31H:
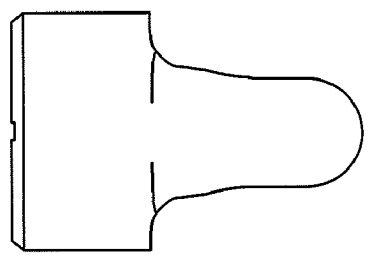
Figure 31I:
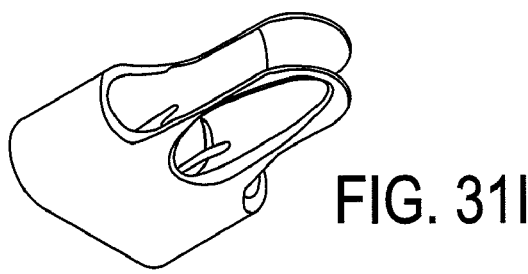
Figure 32A:
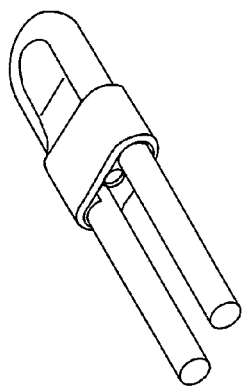
FIGS. 32A-I show the alternative distal end views shown in FIGS. 31A-I including the support wire.
Figure 32B:
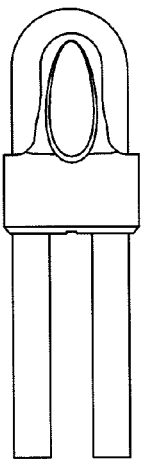
Figure 32C:
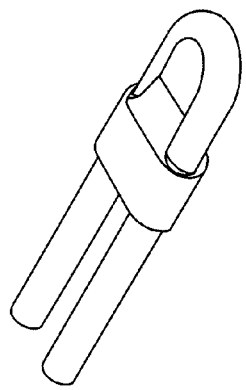
Figure 32D:
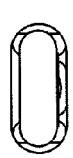
Figure 32E:
Figure 32F:
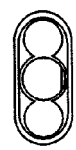
Figure 32G:
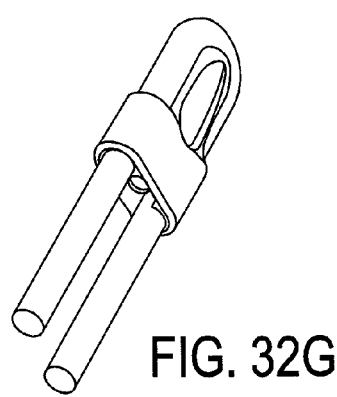
Figure 32H:
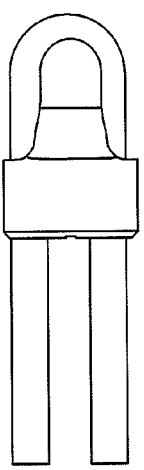
Figure 32I:
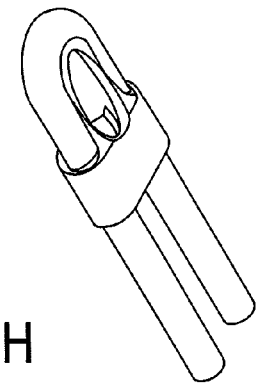

The support wires maybe coupled to the distal tip of the inner member. In general a distal tip may be an atraumatic tip. The distal tip may be flattened and rounded, as indicated in the variation shown in FIGS. 30A-I. In this variation, the distal tip is secured to the distal ends of the two support members (wires 2612, 2612'). For example, the support members may be crimped, clamped, fused, soldered, etc. within the distal tip shown. FIGS. 30A-I illustrate different top perspective views (FIGS. 30A, H, C), front (FIG. 30D), side (FIG. 30E), and back (FIG. 30F) views, and bottom perspective views (FIGS. 30G, B, I).

FIGS. 31A-32I illustrate another variation of a distal tip for the inner member of a probe. In this variation, the support member(s) loop or wrap around the front of the tip. Thus, the tip may be slightly narrower than the variation shown in FIGS. 30A-I. For example, FIGS. 31A-I illustrate different top perspective views (FIGS. 31A, H, C), front (FIG. 31D), side (FIG. 31E) and back (31F) views, and bottom perspective views (FIGS. 31G, B, I) of this variation. FIGS. 32A-I show the same variation of FIGS. 31A-I with the support member (cable, wire, rod, etc.) indicated.

The examples and illustrations included herein show, by way of illustration and not of limitation, specific embodiments in which the subject matter may be practiced. Other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of capturing a pullwire using a pullwire handle device configured to secure to a distal end of a pullwire, the method comprising:
    inserting the distal end of a pullwire into the pullwire handle device;
    advancing the pullwire further into the pullwire handle device while the distal end of the pullwire is contained within the pullwire handle device;
    locking the pullwire within the pullwire handle device;
    coupling a device to a proximal region of the pullwire; and
    pulling on the pullwire handle device to advance the device through a spinal foramen.

2. The method of claim 1, the advancing step comprising advancing the pullwire into a storage chamber of the pullwire handle device.

3. The method of claim 2, the advancing step further comprising advancing the pullwire against a surface within the storage chamber such that the pullwire buckles and is stored within the storage chamber.

4. The method of claim 1, the locking step comprising releasing a button coupled to a locking mechanism to lock the locking mechanism and secure the distal portion of the pullwire within the pullwire handle device.

5. The method of claim 1, the locking step comprising moving the pullwire and pullwire handle device with respect to one another to lock the distal portion of the pullwire within the pullwire handle device.

6. The method of claim 5, wherein moving the pullwire and pullwire handle device with respect to one another comprises moving the pullwire and pullwire handle device with respect to one another such that a portion of the pullwire moves out of the pullwire handle.

7. The method of claim 1, further comprising the step of pulling on the pullwire handle device to manipulate the pullwire relative to a patient through which the pullwire passes.

8. The method of claim 7, the pulling step comprising pulling on the pullwire handle device to advance a proximal portion of the pullwire in a distal direction through a spinal foramen.

9. The method of claim 7, the pulling step comprising pulling on the pullwire handle device to transmit a force to a proximal portion of the pullwire, wherein the force is greater than 10 pounds.

10. The method of claim 7, the pulling step comprising pulling on the pullwire handle device to transmit a force to a proximal portion of the pullwire, wherein the force is greater than 35 pounds.

11. A method of capturing a pullwire using a pullwire handle device configured to secure to the distal end of a pullwire, the method comprising:
    inserting the distal end of the pullwire into the pullwire handle device;
    moving a cam surface of a locking mechanism of the pullwire handle device such that the cam surface applies a force to a clamp plate and the clamp plate applies a force to the pullwire, wherein moving the cam surface comprises rotating the cam surface against the clamp plate and moves the clamp plate toward the pullwire; and
    moving the clamp plate within the pullwire handle device such that the cam surface applies an increased force to the clamp plate and the clamp plate secures the pullwire.

12. The method of claim 11, the moving the cam surface step comprising moving the clamp plate within the pullwire handle device such that the cam surface further rotates against the clamp plate and further moves the clamp plate toward the pullwire.

13. The method of claim 11, the moving a cam surface step comprising releasing a pressed button coupled to a first end of a lever arm, wherein a second end of the lever arm is coupled to the cam surface.

14. The method of claim 13, wherein as the button is released, the lever arm rotates, thereby rotating the cam surface against the clamp plate.

15. The method of claim 11, the moving the clamp plate step comprising moving the pullwire and pullwire handle device with respect to one another such that the clamp plate moves within the pullwire handle device.

16. The method of claim 15, wherein moving the pullwire and pullwire handle device with respect to one another comprises moving the pullwire and pullwire handle device with respect to one another such that a portion of the pullwire moves out of the pullwire handle and the clamp plate moves toward the proximal end of the pullwire handle device.

* * * * *